United States Patent
Planelles et al.

(10) Patent No.: US 9,730,928 B2
(45) Date of Patent: Aug. 15, 2017

(54) TRIZOL-1-OL ANALOGS ANTI-RETROVIRAL LATENCY DRUGS

(71) Applicant: University of Utah Research Foundation, Salt Lake City, UT (US)

(72) Inventors: Vincente Planelles, Salt Lake City, UT (US); Alberto Bosque-Pardos, Salt Lake City, UT (US); Chris M. Ireland, Salt Lake City, UT (US); Ryan Van Wagoner, Salt Lake City, UT (US); Mary Kay Harper-Ireland, Salt Lake City, UT (US); John Alan Maschek, Salt Lake City, UT (US)

(73) Assignee: Univeristy of Utah Research Foundation, Salt Lake City, UM (US)

( * ) Notice: Subject to any disclaimer, the term of this patent is extended or adjusted under 35 U.S.C. 154(b) by 0 days.

(21) Appl. No.: 14/896,906

(22) PCT Filed: Jun. 13, 2014

(86) PCT No.: PCT/US2014/042418
§ 371 (c)(1),
(2) Date: Dec. 8, 2015

(87) PCT Pub. No.: WO2014/201426
PCT Pub. Date: Dec. 18, 2014

(65) Prior Publication Data
US 2016/0151365 A1    Jun. 2, 2016

Related U.S. Application Data

(60) Provisional application No. 61/835,297, filed on Jun. 14, 2013.

(51) Int. Cl.
*A61K 31/501* (2006.01)
*A61K 31/416* (2006.01)
(Continued)

(52) U.S. Cl.
CPC .......... *A61K 31/501* (2013.01); *A61K 31/416* (2013.01); *A61K 31/4192* (2013.01);
(Continued)

(58) Field of Classification Search
CPC ............ A61K 2300/00; A61K 31/4192; A61K 31/437; A61K 31/53; A61K 31/416;
(Continued)

(56) References Cited

U.S. PATENT DOCUMENTS 6,790,657 B1    9/2004    Arya
6,962,810 B2    11/2005    Fraser et al.
(Continued)

FOREIGN PATENT DOCUMENTS

EP    14811218.8    6/2014
EP    3008043 A2    4/2016
(Continued)

OTHER PUBLICATIONS

Fu et al (Bioorganic and Medicinal Chemistry, 18 (2010) pp. 8457-8462).*
(Continued)

*Primary Examiner* — Savitha Rao
(74) *Attorney, Agent, or Firm* — Ballard Spahr LLP

(57) ABSTRACT

In one aspect, the invention relates to triazol-1-ol compounds, analogs thereof, compositions comprising same, and methods of using same, alone or in combination with other agents, to reactivate latent retroviruses, and more particularly to reactivate latent HIV-1. Such compounds, compositions, and methods can be used, for example, in connection with diagnosing and/or treating a retrovirus, and more specifically HIV-1. This abstract is intended as a scanning tool for purposes of searching in the particular art and is not intended to be limiting of the present invention.

20 Claims, 40 Drawing Sheets

(51) Int. Cl.
*A61K 31/53* (2006.01)
*A61K 45/06* (2006.01)
*C07D 231/54* (2006.01)
*C07D 249/04* (2006.01)
*A61K 31/4192* (2006.01)
*A61K 31/437* (2006.01)
*C07D 249/18* (2006.01)
*C07D 253/08* (2006.01)
*C07D 403/04* (2006.01)
*C07D 471/04* (2006.01)

(52) U.S. Cl.
CPC ............ *A61K 31/437* (2013.01); *A61K 31/53* (2013.01); *A61K 45/06* (2013.01); *C07D 231/54* (2013.01); *C07D 249/04* (2013.01); *C07D 249/18* (2013.01); *C07D 253/08* (2013.01); *C07D 403/04* (2013.01); *C07D 471/04* (2013.01)

(58) Field of Classification Search
CPC .... A61K 31/501; A61K 45/06; C07D 231/54; C07D 249/04; C07D 249/18; C07D 253/08; C07D 403/04; C07D 471/04
See application file for complete search history.

(56) References Cited

U.S. PATENT DOCUMENTS

| | | |
|---|---|---|
| 7,226,780 B2 | 6/2007 | Arya |
| 2010/0291067 A1 | 11/2010 | Planelles et al. |
| 2011/0305774 A1* | 12/2011 | Savarino .............. A61K 31/555 424/623 |

FOREIGN PATENT DOCUMENTS

| | | |
|---|---|---|
| WO | WO-93/25234 A1 | 12/1993 |
| WO | WO-94/06920 A1 | 3/1994 |
| WO | PCT/US2014/042418 | 6/2014 |
| WO | WO-2014/201426 A2 | 12/2014 |

OTHER PUBLICATIONS

Nakamura, I. et al. Transition-Metal-Catalyzed Reactions in Heterocyclic Synthesis. Chem. Rev. 2004, vol. 104, p. 2127.*
Schafer et al. Drug Discovery Today 2008, 13 (21/22), 913-916.*
Horig et al. Journal of Translational Medicine 2004, 2(44).*
Abraham RT, et al. (2004) Jurkat T cells and development of the T-cell receptor signalling paradigm. Nat Rev Immunol. 4(4):301-308.
Akkina RK, et al. (1996) High-efficiency gene transfer into CD34+ cells with a human immunodeficiency virus type 1-based retroviral vector pseudotyped with vesicular stomatitis virus envelope glycoprotein G. J Virol. 70(4):2581-2585.
Andersen JL, et al. (2006) HIV-1 VPR-induced apoptosis is cell cycle dependent and requires Bax but not ANT. PLoS Pathog. 2(12):e127.
Andrea, (2012) Basic markers of T cell populations in human PBMC, PBMC Basic, pp. 1-2.
Antoni B, et al (1994) NF-κB-dependent and -independent pathways of HIV activation in a chronically infected T cell line. Virology 202:684-694.
Archin et al, (2009) Expression of latent human immunodeficiency type 1 is induced by novel and selective histone deacetylase inhibitors, AIDS, vol. 23 (14), pp. 1-16.
Bauer B, et al. (2000) T cell expressed PKCΘ demonstrates cell-type selective function. Eur J Immunol. 30(12):3645-3654.
Bosque A, et al (2009) Induction of HIV-1 latency and reactivation in primary memory CD4+ T cells. Blood 113:58-65.
Bosque A, et al (2010) Studies of HIV-1 latency in an ex vivo model that uses primary central memory T cells. Methods.

Bosque A, et al (2011) Homeostatic Proliferation Fails to Efficiently Reactivate HIV-1 Latently Infected Central Memory CD4+ T Cells. PLOS Pathog. 7(10).
Brenchley et al. (2002) Expansion of activated human naive T-cells precedes effector Function, Clinical & Experimental Immunology, 202, vol. 130 (3), pp. 431-440.
Brenchley JM, et al. (2004) T-cell subsets that harbor human immunodeficiency virus (HIV) in vivo: implications for HIV pathogenesis. J Virol. 78(3):1160-1168.
Brooks DG, et al. (2001) Generation of HIV latency during thymopoiesis. Nat Med. 7(4):459-464.
Brooks DG, et al. (2003) Molecular characterization, reactivation, and depletion of latent HIV. Immunity. 19(3):413-423.
Butera ST, et al. (1994) Human immunodeficiency virus type 1 RNA expression by four chronically infected cell lines indicates multiple mechanisms of latency. J Virol. 68(4):2726-2730.
Butler SL, et al. (2001) A quantitative assay for HIV DNA integration in vivo. Nat Med. 7(5):631- 634.
Böhnlein E, et al. (1988) The same inducible nuclear proteins regulates mitogen activation of both the interleukin-2 receptor-alpha gene and type 1 HIV. Cell. 53(5):827-836.
Cannon P, et al. (1994) Analysis of Tat function in human immunodeficiency virus type 1-infected low-level-expression cell lines U1 and ACH-2. J Virol. 68(3):1993-1997.
Caux et al. (1997) CD34+ Hematopoetic Progenitors From Human Cord Blood Differentiate Along Two Independent Dendritic Cell Pathways in Response to Granulocyte-Macrophage Colony-Simulating Factor Plus Tumor Necrosis Factor, Blood 1997, vol. 90, No. 4, pp. 1458-1470.
Challita-Eid PM, et al. (1998) Inhibition of HIV type 1 infection with a RANTES-IgG3 fusion protein. AIDS Res Hum Retroviruses. 14(18):1617-1624.
Chen BK, et al. (1994) Distinct modes of human immunodeficiency virus type 1 proviral latency revealed by superinfection of nonproductively infected cell lines with recombinant luciferase-encoding viruses. J Virol. 68(2):654-660.
Chun TW, et al (1997) Quantification of latent tissue reservoirs and total body viral load in HIV-1 infection. Nature 387:183-188.
Costello et al. (2000) Gene Transfer to stimulated and unstimulated T Lymphocytes by HIV-1 derived lentiviral vectors, Gene Therapy, vol. 7, No. 7, pp. 596-604.
Cruse et al, (2003) Illustrated Dictionary of Immunology, second edition, CRC Press, pp. 160 and 345.
D'Adda di Fagagna F, et al. (1995) Molecular and functional interactions of transcription factor USF with the long terminal repeat of human immunodeficiency virus type 1. J Virol. 69(5):2765-2775.
Dardalhon et al. (2000) Highly efficient gene transfer in native human T cells with a murine leukemia virus-based vector, Gene Therapy, vol. 96, Nu. 3, pp. 885-893.
Davis et al. (2004) ABC transporter inhibitors that are substrates enhance lentiviral vector transduction into primitive hematopoietic progenitor cells, Blood journal, vol. 104 (2) pp. 363-373.
DeHart JL, et al. (2005) The ataxia telangiectasia-mutated and Rad3-related protein is dispensable for retroviral integration. J Virol. 79(3):1389-1396.
Dienz O, et al. (2007) Accumulation of NFAT mediates IL-2 expression in memory, but not naïve, CD4+ T cells. Proc Natl Acad Sci U S A. 104(17):7175-7180.
Douek DC, et al. (2003) T cell dynamics in HIV-1 infection. Annu Rev Immunol. 21:265-304.
Douglas JL, et al. (2001) Efficient human immunodeficiency virus-based vector transduction of unstimulated human mobilized peripheral blood CD34+ cells in the SCID-hu Thy/Liv model of human T cell lymphopoiesis. Hum Gene Ther. 12(4):401-413.
Duh EJ, et al. (1989) Tumor necrosis factor alpha activates human immunodeficiency virus type 1 through induction of nuclear factor binding to the NF-κB sites in the long terminal repeat. Proc Natl Acad Sci U S A. 86(15):5974-5978.
Etienne-Julan M, et al. (1992) The efficiency of cell targeting by recombinant retroviruses depends on the nature of the receptor and the composition of the artificial cell-virus linker. J Gen Virol. 73 (Pt 12):3251-3255.

(56) References Cited

OTHER PUBLICATIONS

Finzi D, et al (1997) Identification of a reservoir for HIV-1 in patients on highly active antiretroviral therapy. Science 278:1295-1300.
Folks TM, et al (1987) Cytokine-induced expression of HIV-1 in a chronically infected promonocyte cell line. Science 238: 800-802.
Folks TM, et al. (1989) Tumor necrosis factor alpha induces expression of human immunodeficiency virus in a chronically infected T-cell clone. Proc Natl Acad Sci U S A. 86(7):2365-2368.
Franke TF, et al. (1995) The protein kinase encoded by the Akt proto-oncogene is a target of the PDGF-activated phosphatidylinositol 3-kinase. Cell. 81(5):727-736.
Fu et al, (2010) Discovery of 1 H-benzo[d][1,2,3] triazol-1-yl 3,4,5-trimethoxybenzoate as a potential antiproliferative agent inhibiting histone deacetylase, Bioorganic & Medicinal Chemistry, vol. 18, pp. 8457-8462.
Giffin MJ, et al. (2003) Structure of NFAT1 bound as a dimer to the HIV-1 LTR κB element. Nat Struct Biol. 10(10):800-806.
Goud B, et al. (1988) Antibody-mediated binding of a murine ecotropic Moloney retroviral vector to human cells allows internalization but not the establishment of the proviral state. Virology. 163(1):251-254.
Gomez-Benito M, et al. (2005) Apo2L/TRAIL is an indirect mediator of apoptosis induced by interferon-α in human myeloma cells. FEBS Lett. 579(27):6217-6222.
Hintzen, R. et al. (1993) Regulation of CD 27 Expression on Subset of Mature T-Lymphocytes, J. Immunol., vol. 151, No. 5, pp. 2426-2435.
Humearu et al. (2004) Efficient Lentiviral Vector-Mediated Control of HIV-1 Replication in CD4 Lymphocytes from Diverse HIV+ Infected Patients Grouped According to CD4 Count and Viral Load, Molecular Therapy, vol. 9 pp. 902-913.
Isakov N, et al. (1987) T-lymphocyte activation: the role of protein kinase C and the bifurcating inositol phospholipid signal transduction pathway. Immunol Rev. 95:89-111.
Jones KA, et al. (1986) Activation of the AIDS retrovirus promoter by the cellular transcription factor, Sp1. Science. 232(4751):755-759.
Jordan A, et al (2003) HIV reproducibly establishes a latent infection after acute infection of T cells in vitro. Embo J 22:1868-1877.
Kane LP, et al. (2000) Signal transduction by the TCR for antigen. Curr Opin Immunol. 12(3):242- 249.
Kim YK, et al. (2006) Recruitment of TFIIH to the HIV LTR is a rate-limiting step in the emergence of HIV from latency. EMBO J. 25(15):3596-3604.
Lacroix I, et al. (2002) Sp1 transcriptional activity is up-regulated by phosphatase 2A in dividing T lymphocytes. J Biol Chem. 277(11):9598-9605.
Lahm HW, et al. (1985) Characterization of recombinant human interleukin-2 with micromethods. J Chromatogr. 326:357-3561.
Lehrman G, et al. (2005) Depletion of latent HIV-1 infection in vivo: a proof-of-concept study. Lancet. 366(9485):549-555.
Lin J, et al. (2001) T cell receptor signalling. J Cell Sci. 114(Pt 2):243-244.
Lu et al. (2004) Safe two-plasmid production for the first clinical lentivirus vector that achieves > 99% transduction in primary cells using a once-step protoc, J. Gene. Med., vol. 6, pp. 963-973.
Luther-Wyrsch A, et al. (2001) Stable transduction with lentiviral vectors and amplification of immature hematopoietic progenitors from cord blood of preterm human fetuses. Human Gene Therapy. 12(4):377-389.
Messi M, et al. (2003) Memory and flexibility of cytokine gene expression as separable properties of human T(H)1 and T(H)2 lymphocytes. Nat Immunol. 4(1):78-86.
Muhlebach et al. (2005) Stable Transduction of Primary Human Monocytes by Simian Lentiviral Vector PBj, Molecular Therapy, vol. 12, pp. 1206-1216.
Neda H, et al. (1991) Chemical modification of an ecotropic murine leukemia virus results in redirection of its target cell specificity. J Biol Chem. 266(22):14143-14146.

Newcomb et al. (2009) Chapter 9, Umbilical Cord Blood cells in Methods in Molecular Biology, Neura cell Transplantation, vol. 549, Humana Press, a part of Springer Science + Business Media, LLC, pp. 119-136.
Nordheim A. (1994) Transcription factors. CREB takes CBP to tango. Nature. 370(6486):177-178.
Osborn L, et al. (1989) Tumor necrosis factor alpha and interleukin 1 stimulate the human immunodeficiency virus enhancer by activation of the nuclear factor κB. Proc Natl Acad Sci U S A. 86(7):2336-2340.
Perkins ND, et al. (1994) Transcription factor AP-2 regulates human immunodeficiency virus type 1 gene expression. J Virol. 68(10):6820-6823.
Persaud D, et al. (2003) Latency in human immunodeficiency virus type 1 infection: no easy answers. J Virol. 77(3):1659-1665.
Poeschla E, et al. (1996) Development of HIV vectors for anti-HIV gene therapy. Proc Natl Acad Sci USA. 93(21):11395-11399.
Qui et al. (2000) Analysis of Surface markers of expanded human umbilical cord blood cells in vitro,vol. 21, (8), pp. 409-411, Abstract only.
Rivino L, et al. (2004) Chemokine receptor expression identifies Pre-T helper (Th)1, Pre-Th2, and nonpolarized cells among human CD4+ central memory T cells. J Exp Med. 200(6):725-735.
Round JL, et al. (2007) Scaffold protein DIgh1 coordinates alternative p38 kinase activation, directing T cell receptor signals toward NFAT but not NF-KκB transcription factors. Nat Immunol. 8(2):154-161.
Roux P, et al. (1989) A versatile and potentially general approach to the targeting of specific cell types by retroviruses: application to the infection of human cells by means of major histocompatibility complex class I and class II antigens by mouse ecotropic murine leukemia virus-derived viruses. Proc Natl Acad Sci U S A. 86(23):9079-9083.
Ruocco MR, et al. (1996) Regulation of HIV-1 long terminal repeats by interaction of C/EBP(NF-IL6) and NF-κB/Rel transcription factors. J Biol Chem. 271(37):22479-22486.
Sheridan PL, et al. (1995) Activation of the HIV-1 enhancer by the LEF-1 HMG protein on nucleosome-assembled DNA in vitro. Genes Dev. 9(17):2090-2104.
Simm M, et al. (1995) Aberrant Gag protein composition of a human immunodeficiency virus type 1 vif mutant produced in primary lymphocytes. J Virol. 69(7):4582-4586.
Simon G, et al. (1994) Valpoic acid reduces the intracellular level of glutathione and stimulates human immunodeficiency virus. Chem Biol Interact. 91(2-3):111-121.
Svarovskaia ES, et al. (2004) Azido-containing diketo acid derivatives inhibit human immunodeficiency virus type 1 integrase in vivo and influence the frequency of deletions at two-long-terminal-repeat-circle junctions. J Virol. 78(7):3210-3222.
Swaroop N, et al. (2001) Inhibition of nuclear transcription factor-κB by specific IκB kinase peptide inhibitor. Pharm Res. 18(11):1631-1633.
Tesmer VM, et al. (1993) NF-IL6-mediated transcriptional activation of the long terminal repeat of the human immunodeficiency virus type 1. Proc Natl Acad Sci U S A. 90(15):7298-7302.
Vandegraaff N, et al. (2001) Specific inhibition of human immunodeficiency virus type 1(HIV-1) integration in cell culture: putative inhibitors of HIV-1 integrase. Antimicrobial Agents Chemotherapy 45(9):2510-2516.
Vicart A, et al. (2006) Increased chromatin association of Sp1 in interphase cells by PP2A-mediated dephosphorylations. J Mol Biol. 364(5):897-908.
Ylisastigui L, et al. (2004) Coaxing HIV-1 from resting CD4 T cells: histone deacetylase inhibition allows latent viral expression. AIDS. 18(8):1101-1108.
Zhu Y, et al. (2001) Comparison of cell cycle arrest, transactivation, and apoptosis induced by the simian immunodeficiency virus SIVagm and human immunodeficiency virus type 1 vpr genes. J Virol. 75(8):3791-3801.
International Search Report and Written Opinion were mailed on Dec. 24, 2014 for Application No. PCT/US14/42418, which was

(56) References Cited

OTHER PUBLICATIONS filed on Jun. 13, 2014 and published as WO 2014/201426 on Dec. 18, 2014 (Applicant—University of Utah Research Foundation) (9 pages).
Requirement for Restriction/Election was issued on Oct. 27, 2011 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (15 pages).
Response to Requirement for Restriction/Election was mailed on Dec. 27, 2011 to the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (5 pages).
Non Final Rejection was issued on Jan. 20, 2012 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (6 pages).
Response to Non Final Rejection was mailed on May 21, 2012 to the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (12 pages).
Final Rejection was issued on Apr. 3, 2013 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (6 pages).
Response to Final Rejection was mailed on Jul. 3, 2013 to the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (11 pages).
Non Final Rejection was issued on Sep. 9, 2013 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (6 pages).
Response to Non Final Rejection was mailed on Feb. 28, 2014 to the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (12 pages).
Final Rejection was issued on Apr. 30, 2014 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (9 pages).
Response to Final Rejection was mailed on Jul. 30, 2014 to the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (11 pages).
Response to Final Rejection was mailed on Oct. 16, 2014 to the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (11 pages).
Non Final Rejection was issued on Nov. 21, 2014 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (9 pages).
Response to Non Final Rejection was mailed on May 21, 2015 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (12 pages).
Final Rejection was issued on Jun. 17, 2015 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (11 pages).
Response to Final Rejection was mailed on Sep. 17, 2015 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (16 pages).
Final Rejection was issued on Oct. 1, 2015 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (12 pages).
Response to Final Rejection was mailed on Apr. 1, 2016 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (11 pages).
Non Final Rejection was issued on Sep. 26, 2016 by the U.S. Patent and Trademark Office for U.S. Appl. No. 12/695,075, filed Jan. 27, 2010 and published as US-2010-0291067-A1 on Nov. 18, 2010 (Inventor—Vicente Planelles et al) (11 pages).
U.S. Appl. No. 61/835,297, filed Jun. 14, 2013, Vincente Planelles et al.
U.S. Appl. No. 61/147,649, filed Jan. 27, 2009, Vincente Planelles et al.

* cited by examiner

TRIZOL-1-OL ANALOGS ANTI-RETROVIRAL LATENCY DRUGS

CROSS-REFERENCE TO RELATED APPLICATIONS

This Application claims benefit of priority under 35 U.S.C. §371 of International Application No. PCT/US2014/042418, filed Jun. 13, 2014, which claims the benefit of U.S. Provisional Patent Application No. 61/835,297, filed Jun. 14, 2013, which are incorporated herein by reference in their entireties.

STATEMENT REGARDING FEDERALLY SPONSORED RESEARCH

This invention was made with government support under Grant Number AI087508 awarded by the National Institutes of Health. The government has certain rights in the invention.

BACKGROUND

The advent of highly active anti-retroviral therapy (HAART), which involves the use of three or more antiretroviral drugs, has led to a significant improvement in the care and survival of patients infect with HIV-1. In patients not infected with resistant strains of the virus. HAART typically results in a dramatic decrease in viral load often from levels of 10,000-100,000 RNA copies/mL of plasma to less than 50 copies/mL.

Given the dramatic effects of HAART, it was proposed that complete elimination of the virus might be possible within 2 to 3 years. However, even after long-term suppression of viral replication with HAART, the virus rapidly rebounds after therapy is discontinued. A key contributor to viral rebound appears to be a reservoir of latently infected cells, including CD4 memory T cells. The half-life of the latently infected population is quite long, and it is estimated that it would take over 60 years of HAART to eliminate this population. Therefore, life-long HAART would be required to control infection in patients Retroviruses, including HIV-1, are RNA viruses that replicate through a DNA intermediate and integrate very efficiently into the genome of an infected cell, forming a provirus. Once the provirus is formed, it is maintained in the genome of the infected cell and transferred to daughter cells in the same fashion as any other genetic element within the cellular genome. Thus, the virus has the potential to persist if it infects long-lived cells such as memory T cells. It has been known since 1986 that HIV-1 can establish a latent infection in culture. It was found that a human T cell line infected with replication-competent virus could develop a latent infection in which the provirus was dormant but could be reactivated upon stimulation. Since then it has been established that a number of cytokines can reactivate latent proviruses.

The role that latency is playing in preventing clearance of the virus infection has become evident in recent years. Patients that had been successfully treated with HAART in which viral RNA was maintained at levels below 50 copies/mL in the plasma for years, experienced rapid virus rebound upon withdrawal of therapy. Moreover, it was found that after T cell activation, virus could be isolated from CD4 T cells taken from these patients making it clear that to eradicate the virus it will be necessary to eliminate the latently infected cells.

There have been attempts to flush the latent virus from infected individuals by nonspecific activation of T cells to "turn on" latent proviruses. As part of this approach, the patients remain on HAART to prevent new infections, and the infected cells from which the latent proviruses are activated should die due to cytotoxic effects of viral expression and/or because of targeting by the immune system which can recognize the cells once they begin to express the viral proteins. Agents that can dissociate latent virus activation from global T cell activation, however, are extremely rare. Thus, there remains a need for new drugs capable of selectively activating latent viruses.

SUMMARY

In accordance with the purpose(s) of the invention, as embodied and broadly described herein, the invention, in one aspect, relates to methods of activating a latent retrovirus in a subject, the method comprising the step of administering to the subject an effective amount of a compound represented by a formula:

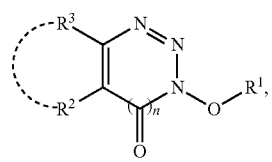

wherein n is 0 or 1; wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein $R^2$ is selected from H and C1-C4 alkyl; and wherein $R^3$ is selected from H and C1-C4 alkyl, or $R^2$ and $R^3$ are covalently bonded and, together with the intermediate atoms, comprise an optionally substituted fused six-membered aryl or heteroaryl ring.

Also disclosed are methods for the manufacture of a medicament for treatment of a retrovirus in a subject, the method comprising the step of combining an effective amount of a compound represented by a formula:

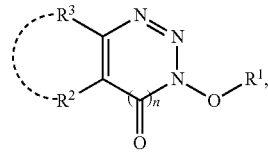

wherein n is 0 or 1, wherein $R^1$ is selected from H, C1-C4 alkyl, C1-C6 aryl, C(O)Ar, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), or 1-(piperidin-1-ylmethylene)piperidin-1-ium hexafluorophosphate (V); wherein $R^2$ is selected from H and C1-C4 alkyl; wherein $R^3$ is selected from H and C1-C4 alkyl, or $R^2$ and $R^3$ are covalently bonded and, together with the intermediate atoms, comprise an optionally substituted fused six-membered aryl or heteroaryl ring; with a pharmaceutically acceptable carrier or diluent.

Also disclosed are kits comprising at least one compound represented by a formula:

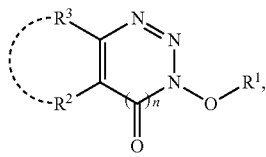

wherein n is 0 or 1; wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein $R^2$ is selected from H and C1-C4 alkyl; and wherein $R^3$ is selected from H and C1-C4 alkyl, or $R^2$ and $R^3$ are covalently bonded and, together with the intermediate atoms, comprise an optionally substituted fused six-membered aryl or heteroaryl ring; and one or more of:
  a) at least one agent known to treat a retrovirus;
  b) instructions for detecting a retrovirus; and
  c) instructions for treating a retrovirus.

Also disclosed are pharmaceutical compositions comprising a compound represented by a formula:

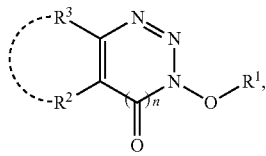

wherein n is 0 or 1; wherein $R^1$ is selected from H, C1-C4 alkyl, C1-C6 aryl, C(O)Ar, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein $R^2$ is selected from H and C1-C4 alkyl; wherein $R^3$ is selected from H and C1-C4 alkyl, or $R^2$ and $R^3$ are covalently bonded and, together with the intermediate atoms, comprise an optionally substituted fused six-membered aryl or heteroaryl ring; and a pharmaceutically acceptable carrier or diluent.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1A:
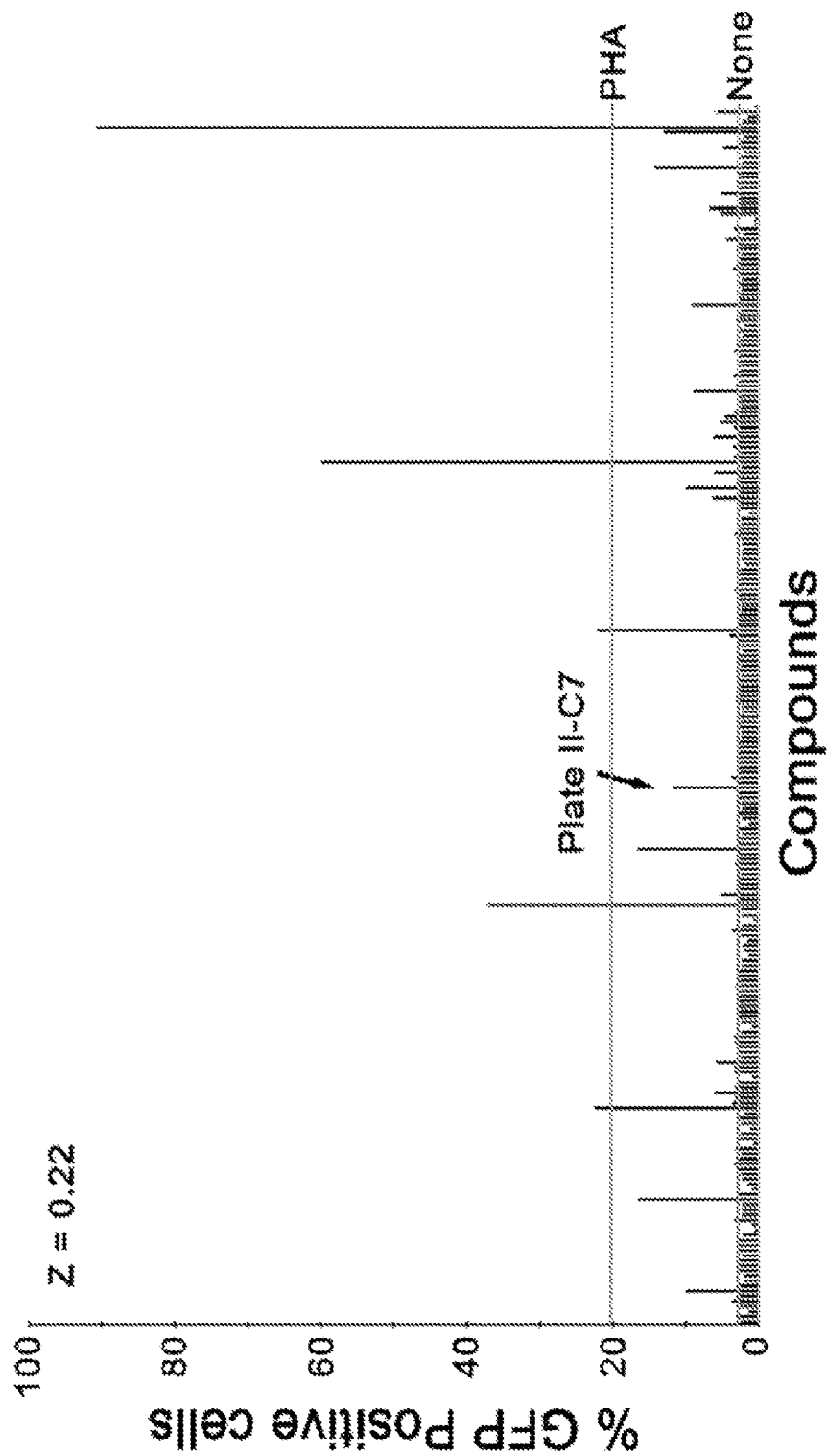
FIG. 1A shows the results of a screen of the Ireland Natural Product Collection, a set of natural products isolated from marine invertebrate animals and microorganisms. Plate II well C07 was identified as a positive result and was taken on for further analysis.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples and Figures included herein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a clinical interview and/or a physical examination by a person of skill, for example, a physician, and found to have a condition that can be diagnosed or treated by the compounds, compositions, or methods disclosed herein. For example, "diagnosed with a depression disorder" means having been subjected to a clinical interview and/or physical examination by a person of skill, for example, a physician, and found to have a condition that can be diagnosed or treated by a compound or composition that can cure, alleviate, prevent, or otherwise treat a depression disorder.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "stable," as used herein, refers to compounds that are not substantially altered when subjected to conditions to allow for their production, detection, and, in certain aspects, their recovery, purification, and use for one or more of the purposes disclosed herein.

By "virion," "viral particle," or "retroviral particle" is meant a single virus minimally composed of an RNA or DNA genome, Pol protein (for reverse transcription of the RNA genome following infection), Gag protein (structural protein present in the nucleocapsid), and an envelope protein. As used herein, the RNA genome of the retroviral particle is usually a recombinant RNA genome, e.g., contains an RNA sequence exogenous to the native retroviral genome and/or is defective in an andogenous retroviral sequence (e.g., is defective in pol, gag, and/or env, and, as used herein, is normally defective in all three genes).

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, such as $^2$H, $^3$H, $^{13}$C, $^{14}$C, $^{15}$N, $^{18}$O, $^{17}$O, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent o a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through noncovalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions and it is understood that there are a variety of structures that can perform the same function that are related to the disclosed structures, and that these structures will typically achieve the same result.

B. Pharmaceutical Compositions

In one aspect, the invention relates to pharmaceutical compositions comprising a compound represented by a formula:

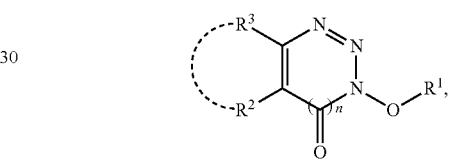

wherein n is 0 or 1; wherein $R^1$ is selected from H, C1-C4 alkyl, C1-C6 aryl, C(O)Ar, $SO_2N(CH_3)_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene) piperidin-1-ium hexafluorophosphate (V); wherein $R^2$ is selected from H and C1-C4 alkyl; wherein $R^3$ is selected from H and C1-C4 alkyl, or $R^2$ and $R^3$ are covalently bonded and, together with the intermediate atoms, comprise an optionally substituted fused six-membered aryl or heteroaryl ring, and a pharmaceutically acceptable carrier or diluent.

In certain aspects, the disclosed pharmaceutical compositions comprise the disclosed compounds and pharmaceutically acceptable salt(s) thereof as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable earlier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the disclosed compositions can be prepared from the disclosed compounds. It is also understood that the disclosed compositions can be employed in the disclosed methods of using.

In a further aspect, the disclosed compositions are for oral administration,

In a further aspect, the disclosed compositions further comprise a therapeutic agent that can be used to treat a retrovirus. In a still further aspect, the therapeutic agent can be used to treat a retrovirus selected from the group comprising HIV-1, HIV-2, SIV, XMRV, HTLV-1, HTLV-2, HTLV-3, or HTLV-4. In yet a further aspect, the therapeutic agent can be used to treat HIV-1. In an even further aspect, the therapeutic agent is selected from entry inhibitors, nucleoside reverse transcriptase inhibitors (NRTIs), nucleotide reverse transcriptase inhibitors (NtRTIs), non-nucleoside reverse transcriptase inhibitors (NNRTIs), protease inhibitors, integrase inhibitors, or maturation inhibitors, or a mixture thereof. In a still further aspect, the therapeutic agent is selected from nucleoside reverse transcriptase inhibitors (NRTIs), nucleotide reverse transcriptase inhibitors (NtRTIs), non-nucleoside reverse transcriptase inhibitors (NNRTIs), protease inhibitors, or integrase inhibitors, or a mixture thereof.

C. Methods Of Using The Compounds And Compositions

The compounds disclosed herein are useful for treating or detecting a retrovirus, and more particularly for treating or detecting HIV-1. Thus, provided is a method of treating or detecting a retrovirus in a subject comprising the step of administering to the subject at least one compound represented by a formula:

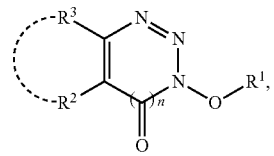

wherein n is 0 or 1; wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein $R^2$ is selected from H and C1-C4 alkyl; and wherein $R^3$ is selected from H and C1-C4 alkyl, or $R^2$ and $R^3$ are covalently bonded and, together with the intermediate atoms, comprise an optionally substituted fused six-membered aryl or heteroaryl ring; and/or at least one disclosed pharmaceutical composition in an effective dosage and amount.

The pharmaceutical compositions and methods of the present invention can further comprise other therapeutically active compounds as noted herein which are usually applied in the treatment of retroviruses, for example HIV-1, HIV-2, SIV, XMRV, HTLV-2, HTLV-3, or HTLV-4.

In various aspects, the disclosed treatment methods can be applied to a subject, for example, a patient. In further aspects, the subject is a mammal, for example, a human.

1. Treatment Methods

In one aspect, the invention relates to methods for the treatment of a patient diagnosed with a retrovirus, the method comprising the step of administering to the patient, together in an effective amount, a compound represented by a formula:

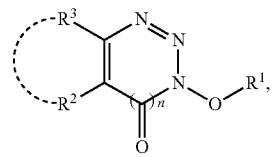

wherein n is 0 or 1; wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V);

wherein R² is selected from H and C1-C4 alkyl; and wherein R³ is selected from H and C1-C4 alkyl, or R² and R³ are covalently bonded and, together with the intermediate atoms, comprise an optionally substituted fused six-membered aryl or heteroaryl ring, and at least one agent known to treat a retrovirus, A. Activation of a Latent Retrovirus In one aspect, the invention relates to methods of activating a latent retrovirus, and more specifically HIV-1, in a subject, the method comprising the step of administering to the subject an effective amount of a compound represented by a formula:

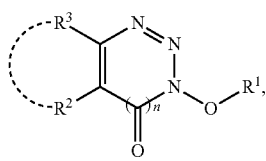

wherein n is 0 or 1; wherein R¹ is selected from H, C1-C4 alkyl, C1-C6 aryl, C(O)Ar, C(O)N(CH₃)₂, SO₂N(CH₃)₂, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein R² is selected from H and C1-C4 alkyl; and wherein R³ is selected from H and C1-C4 alkyl, or R² and R³ are covalently bonded and, together with the intermediate atoms, comprise an optionally substituted fused six-membered aryl or heteroaryl ring.

The use of antiretroviral therapy in human immunodeficiency virus type 1 (HIV-1) infected patients does not lead to virus eradication. This is due, to a significant degree, to the fact that HIV-1 can establish a highly stable reservoir of latently infected cells. The principle reservoir of HIV-1 latency is thought to reside in resting, CD4+ memory T cells, which harbor integrated HIV-1 (Finzi et al. 1997). The low frequency of latently infected cells (1 in 10⁶ resting CD4+ T cells (Chun et al. 1997)), for which known phenotypic markers are not available, poses a great challenge to the study of latency in vivo, Previous studies on HIV-1 latency were based on the generation of chronically infected cell lines, such as the ACH2 (Folks et al. 1989), JΔK (Antoni et al. 1994), and J-Lat (Jordan et al. 2003) T-cell lines, and the U1 promonocytic cell line (Folks et al, 1987). In these systems, latency was defined as a state in which integrated proviruses failed to drive efficient gene expression. However, these systems do not necessarily reflect the latency state in vivo because the lack of viral gene expression is due to mutations in that (ACH2 and U1 (Folks et al. 1989, Folks et al. 1987)) or mutations in the LTR (JΔK T-cell line (Antoni et al. 1994)). While these latency models recapitulate a plethora of mechanisms that can underlie viral latency, the focus of this study was in developing a more general model that did not rely on clonal probiral integration sites, and which utilized non-transformed, primary human T-cells.

A model using human fetal liver tissue in SCID-hu mice has also generated a great deal of interest in the field of HIV-1 latency (Brooks et al. 2001). This model relies upon infection of thymocytes and the vast majority of latently infected cells in this system are mature, quiescent CD4+ single positive naïve T cells. This is in contrast with findings in HIV-1 patients, where the majority of latently infected cells are CD4+ memory T cells (Finzi et al. 1997). Although naïve and memory cells share the characteristic of being quiescent, a likely requirement for HIV-1 latency in T cells (Finzi et at 1997), there are important differences between these cell types that impact latency and reactivation.

More recently, a model using human, primary cells was disclosed in which relevant signaling pathways involved in viral reactivation are dissected from latently infected memory CD4+ cells (Planelles et al. 2010). Replacement of the nef gene with one encoding the green fluorescent protein (GFP) and using GFP as a readout allows for this primary cell model for the study of HIV-1 latency to be suitable for high throughput screening (HTS) of compounds that reactivate HIV-1 from its latency state. Disclosed herein are methods of activating a latent retrovirus, and more particularly latent HIV-1, using compounds identified in this screen.

In a further aspect, the invention relates to a method of activating a latent retrovirus in a subject, the method comprising the step of administering to the subject an effective amount of a compound represented by a formula:

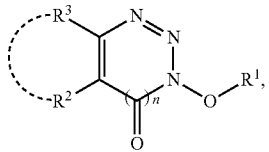

wherein n is 0 or 1; wherein R¹ is selected from H, N-((dimethylamino)methylene)-N-methylmethanaminium tetrafluoroborate, and N-((dimethylamino)methylene)-N-methylmethanaminium hexafluorophosphate (V); wherein R² is selected from H and C1-C4 alkyl; and wherein R³ is selected from H and C1-C4 alkyl, or R² and R³ are covalently bonded and, together with the intermediate atoms, comprise an optionally substituted fused six-membered aryl or heteroaryl ring.

In a further aspect, the invention relates to a method of activating a latent retrovirus in a subject, the method comprising the step of administering to the subject an effective amount of a compound represented by a structure depicted in Table 1.

TABLE 1

| Compound Name | Structure |
| --- | --- |
| 1-hydroxybenzotriazole | 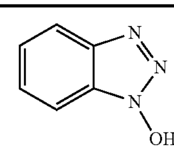 |

TABLE 1-continued

| Compound Name | Structure |
| --- | --- |
| 6-chloro-1H-benzo[d][1,2,3]triazol-1-ol | |
| 1-hydroxy-7-azabenzotriazole | 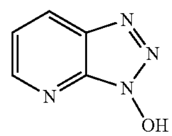 |
| 4,5-dichloro-1-(cyclopentyloxy)-1H-1,2,3-benzotriazole | 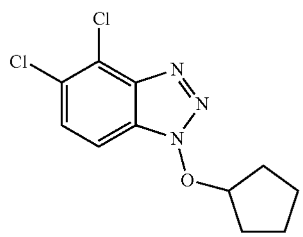 [SMILES: Clc1ccc2c(nnn2OC2CCCC2)c1Cl] |
| 1-(benzoyloxy)-1H-1,2,3-benzotriazole | 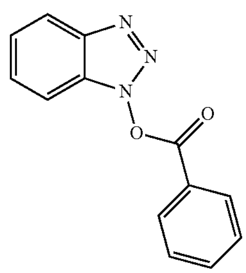 [SMILES: O=C(On1nnc2ccccc21)c1ccccc1] |
| 9-fluorenylmethyl 1-benzotriazolyl carbonate | 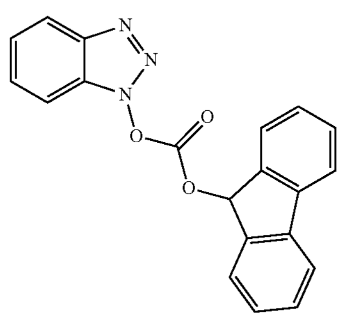 [SMILES: O=C(OC1c2ccccc2-c2ccccc21)On1nnc2ccccc21] |
| 1-{[(dimethylamino)carbonyl]oxy}-6-nitro-1H-1,2,3-benzotriazole | 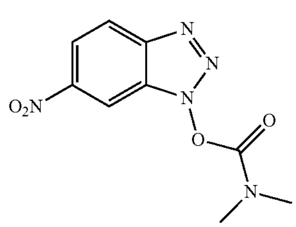 [SMILES: CN(C)C(=O)On1nnc2ccc([N+](=O)[O-])cc21] |
| 1-{[(dimethylamino)sulfonyl]oxy}-6-methyl-1H-1,2,3-benzotriazole | 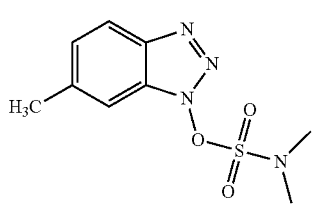 |

TABLE 1-continued

| Compound Name | Structure |
|---|---|
| 1-{[(dimethylamino)sulfonyl]oxy}-5-methyl-1H-1,2,3-benzotriazole | 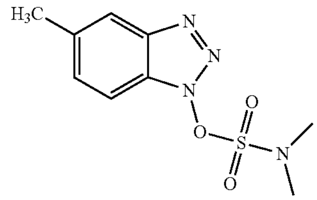 |
| O-(benzotriazole-1-yl)-N,N,N',N'-tetramethyluronium tetrafluoroborate | 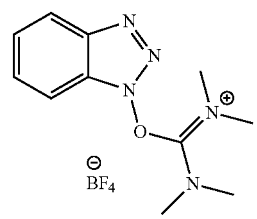 |
| O-(6-chlorobenzotriazol-1-yl)-N,N,N',N'-tetramethyluronium tetrafluoroborate | |
| (benzotriazole-1-yloxy)dipiperidineocarbenium hexafluorophosphate | 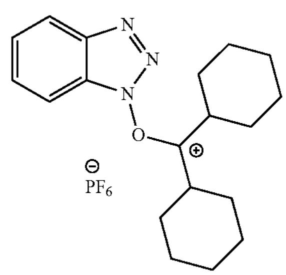 |
| O-(benzotriazole-1-yl)-N,N,N',N'-tetramethyluronium hexafluorophosphate | 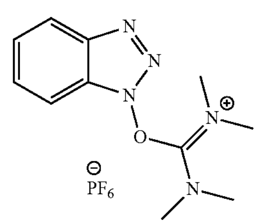 |
| O-(6-chlorobenzotriazol-1-yl)-N,N,N',N'-hexafluorophosphate | 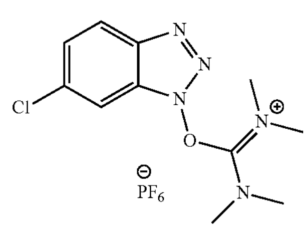 |

TABLE 1-continued

| Compound Name | Structure |
|---|---|
| (benzotriazol-1-yloxy)tripyrrolidinophosphonium hexafluorophosphate | 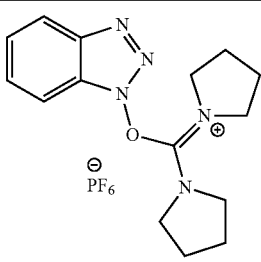 |
| O-(benzotriazole-1-yl-N,N,N',N'-bis(pentamethylene)uranium hexafluorophosphate | 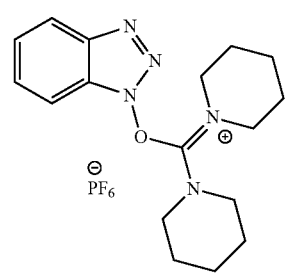 |
| (benzotriazole-1-yloxy)tris(dimethylamino)phosphonium hexafluorophosphate | 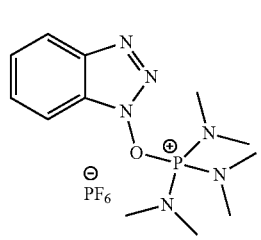 |
| (benzotriazole-1-yloxy)tripyrrolidinophosphonium hexafluorophosphate | 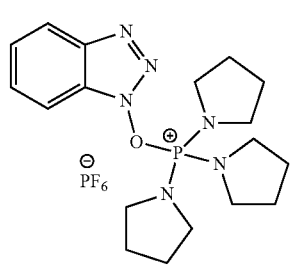 |
| (6-chlorobenzotriazol-1-yloxy)tripyrrolidiniophosphonium hexafluorophosphate | 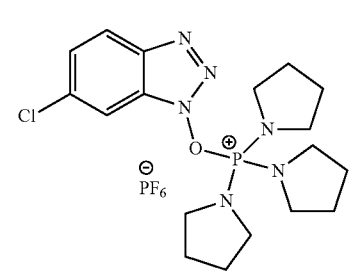 |
| (7-azabenzotriazol-1-yloxy)tripyrrolidinophosphonium hexafluorophosphate | 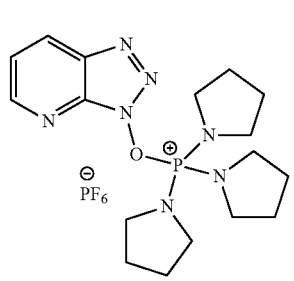 |

TABLE 1-continued

| Compound Name | Structure |
| --- | --- |
| 3-hydroxybenzo[d][1,2,3]triazin-4-(3H)-one | 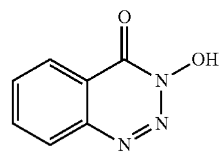 [SMILES: O=c1c2ccccc2nnn1O] |

In a further aspect, the invention relates to a method of activating a latent retrovirus in a subject, the method comprising the step of administering to the subject an effective amount of a compound represented by a formula:

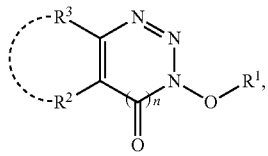

wherein n is 0 or 1; wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein $R^2$ and $R^3$ are covalently bonded and, together with the intermediate atoms, comprise an optionally substituted fused six-membered aryl or heteroaryl ring. In a still further aspect, $R^2$ and $R^3$ are covalently bonded and, together with the intermediate atoms, comprise an optionally substituted fused six-membered aryl ring. In yet a further aspect, $R^2$ and $R^3$ are covalently bonded and, together with the intermediate atoms, comprise an optionally substituted fused phenyl ring. In an even further aspect, $R^2$ and $R^3$ are covalently bonded and, together with the intermediate atoms, comprise an optionally substituted fused six-membered heteroaryl ring. In a still further aspect, $R^2$ and $R^3$ are covalently bonded and, together with the intermediate atoms, comprise an optionally substituted fused pyridine ring.

In a further aspect, the invention relates to a method of activating a latent retrovirus in a subject, the method comprising the step of administering to the subject an effective amount of a compound represented by a formula:

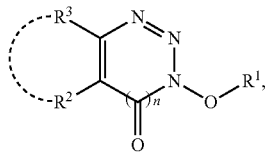

wherein n is 0, $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene) piperidin-1-ium hexafluorophosphate (V); wherein $R^2$ is selected from H and C1-C4 alkyl; and wherein $R^3$ is selected from H and C1-C4 alkyl, or $R^2$ and $R^3$ are covalently bonded and, together with the intermediate atoms, comprise an optionally substituted fused six-membered aryl or heteroaryl ring. In a still further aspect, n is 1.

In a further aspect, the invention relates to a method of activating a latent retrovirus in a subject, the method comprising the step of administering to the subject an effective amount of a compound represented by a formula:

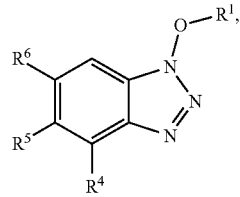

wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri (pyrrolidin-1-yl)phosphonium hexafluorophosphate (V), tris (dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); and wherein each of $R^4$, $R^5$, and $R^6$ is independently selected from H, Cl, CH$_3$, and NO$_2$.

In a still further aspect, the invention relates to a method of activating a latent retrovirus in a subject, the method comprising the step of administering to the subject an effective amount of a compound represented by a formula:

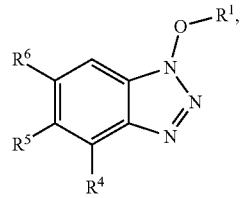

wherein $R^1$ is selected from H and N-((dimethylamino) methylene)-N-methylmethanaminium hexafluorophosphate (V); and wherein each of $R^4$, $R^5$, and $R^6$ is independently selected from H, Cl, CH$_3$, and NO$_2$.

In yet a further aspect, the invention relates to a method of activating a latent retrovirus in a subject, the method comprising the step of administering to the subject an effective amount of a compound represented by a formula:

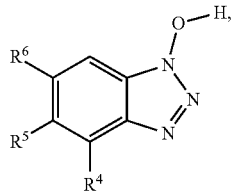

wherein each of $R^4$, $R^5$, and $R^6$ is independently selected from H, Cl, $CH_3$, and $NO_2$.

In an even further aspect, the invention relates to a method of activating a latent retrovirus in a subject, the method comprising the step of administering to the subject an effective amount of a compound represented by a formula:

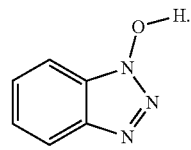

In a still further aspect, the invention relates to a method of activating a latent retrovirus in a subject, the method comprising the step of administering to the subject an effective amount of a compound represented by a formula:

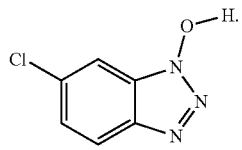

In a further aspect, the invention relates to a method of activating a latent retrovirus in a subject, the method comprising the step of administering to the subject an effective amount of a compound represented by a formula:

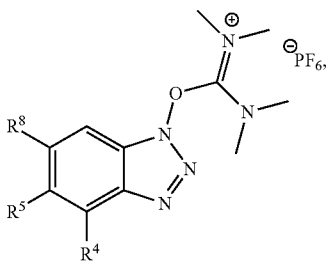

wherein each of $R^4$, $R^5$, and $R^6$ is independently selected from H, Cl, $CH_3$, or $NO_2$.

In a still further aspect, the invention relates to a method of activating a latent retrovirus in a subject, the method comprising the step of administering to the subject an effective amount of a compound represented by a formula:

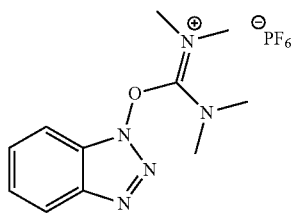

In a further aspect, the invention relates to a method of activating a latent retrovirus in a subject, the method comprising the step of administering to the subject an effective amount of a compound represented by a formula:

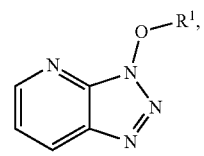

wherein $R^1$ is selected from H, C1-C4 alkyl, C1-C6 aryl, C(O)Ar, $C(O)N(CH_3)_2$, $SO_2N(CH_3)_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri (pyrrolidin-1-yl)phosphonium hexafluorophosphate (V), tris (dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V).

In a still further aspect, the invention relates to a method of activating a latent retrovirus in a subject, the method comprising the step of administering to the subject an effective amount of a compound represented by a formula:

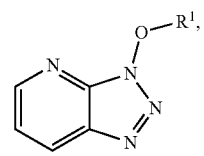

wherein $R^1$ is selected from H and N-((dimethylamino) methylene)-N-methylmethanaminium hexafluorophosphate (V).

In yet a further aspect, the invention relates to a method of activating a latent retrovirus in a subject, the method comprising the step of administering to the subject an effective amount of a compound represented by a formula:

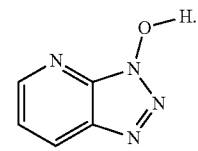

In a further aspect, the invention relates to a method of activating a latent retrovirus in a subject, the method comprising the step of administering to the subject an effective amount of a compound represented by a formula:

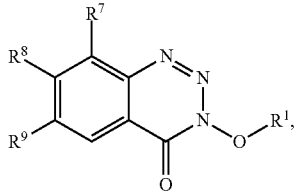

wherein R¹ is selected from H, C1-C4 alkyl, C1-C6 aryl, C(O)Ar, C(O)N(CH₃)₂, SO₂N(CH₃)₂, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); and wherein each of R⁷, R⁸, and R⁹ is independently selected from H, Cl, CH₃, and NO₂.

In a still further aspect, the invention relates to a method of activating a latent retrovirus in a subject, the method comprising the step of administering to the subject an effective amount of a compound represented by a formula:

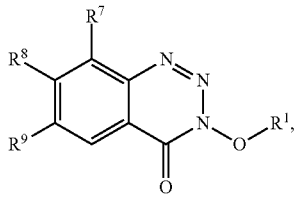

wherein R¹ is selected from H and N-((dimethylamino)methylene)-N-methylmethanaminium hexafluorophosphate (V); and wherein each of R⁷, R⁸, and R⁹ is independently selected from H, Cl, CH₃, and NO₂.

In yet a further aspect, the invention relates to a method of activating a latent retrovirus in a subject, the method comprising the step of administering to the subject an effective amount of a compound represented by a formula:

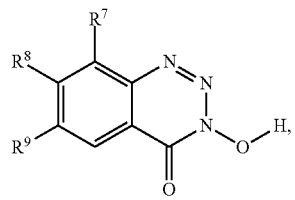

wherein each of R⁷, R⁸, and R⁹ is independently selected from H, Cl, CH₃, and NO₂.

In an even further aspect, the invention relates to a method of activating a latent retrovirus in a subject, the method comprising the step of administering to the subject an effective amount of a compound represented by a formula:

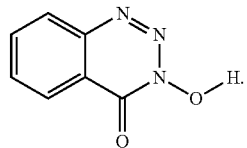

In a further aspect, the invention relates to a method of activating a latent retrovirus in a subject, the method comprising the step of administering to the subject an effective amount of a compound represented by a formula:

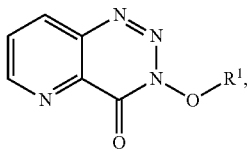

wherein R¹ is selected from H, C1-C4 alkyl, C1-C6 aryl, C(O)Ar, C(O)N(CH₃)₂, SO₂N(CH₃)₂, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V).

In a still further aspect, the invention relates to a method of activating a latent retrovirus in a subject, the method comprising the step of administering to the subject an effective amount of a compound represented by a formula:

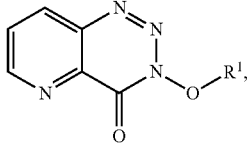

wherein R¹ is selected from H and N-((dimethylamino)methylene)-N-methylmethanaminium hexafluorophosphate (V).

In yet a further aspect, the invention relates to a method of activating a latent retrovirus in a subject, the method comprising the step of administering to the subject an effective amount of a compound represented by a formula:

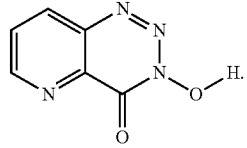

In a further aspect, the subject is a population of cells. In a still further aspect, the subject is a population of cells latently infected with a retrovirus. In yet a further aspect, the subject is a population of cells latently infected with HIV-1.

In a further aspect, the subject is a mammal. In a still further aspect, the subject is a human. In yet a further aspect, the subject is a patient. In an even further aspect, the subject is a patient who has been diagnosed with a need for treatment of a retrovirus prior to the administering step. In a still further aspect, the subject is a patient who has been diagnosed with a need for treatment of HIV prior to the administering step.

B. Agent Known to Treat a Retrovirus

In one aspect, the invention relates to methods of activating a latent retrovirus in a subject, the method further comprising treating the patient with at least one agent that can be used to treat a retrovirus.

In various aspects, the invention relates to methods of activating latent HIV-1 in a subject, the method further comprising treating the patient with at least one agent that can be used to treat HIV-1. In a further aspect, the at least one agent is selected from entry inhibitors, nucleoside reverse transcriptase inhibitors (NRTIs), nucleotide reverse transcriptase inhibitors (NtRTIs), non-nucleoside reverse transcriptase inhibitors (NNRTIs), protease inhibitors, integrase inhibitors, or maturation inhibitors, or a mixture thereof. In a further aspect, the at least one agent is selected from nucleoside reverse transcriptase inhibitors (NRTIs), nucleotide reverse transcriptase inhibitors (NtRTIs), non-nucleoside reverse transcriptase inhibitors (NNRTIs), protease inhibitors, or integrase inhibitors, a mixture thereof. In yet a further aspect, the at least one agent is selected from Maraviroc, Enfuvirtide, Zidovudine, Didanosine, Zalcitabine, Stavudine, Lamivudine, Abacavir, Emtricitabine, Entecavir, Tenofovir, Adefovir, Efavirenz, Nevirapine, Delavirdine, Rilpivirine, Raltegravir, Saquinavir, Ritonavir, Indinavir, Nelfinavir, or Amprenavir, or a mixture thereof. In an even further aspect, the at least one agent is HAART.

Typically, an agent is administered in an effective amount, per its normal dosing instructions. In one aspect, the effective amount is a therapeutically effective amount.

2. Manufacture of a Medicament

In one aspect, the invention relates to methods for the manufacture of a medicament for the treatment of a retrovirus in a subject, the method comprising the step of combining an effective amount of a compound represented by a formula:

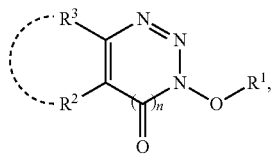

wherein n is 0 or 1, wherein $R^1$ is selected from H, C1-C4 alkyl, C1-C6 aryl, C(O)Ar, $SO_2N(CH_3)_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), or 1-(piperidin-1-ylmethylene)piperidin-1-ium hexafluorophosphate (V); wherein $R^2$ is selected from H and C1-C4 alkyl; wherein $R^3$ is selected from H and C1-C4 alkyl, or $R^2$ and $R^3$ are covalently bonded and, together with the intermediate atoms, comprise an optionally substituted fused six-membered aryl or heteroaryl ring, alone or in combination with another agent, with a pharmaceutically acceptable carrier or diluent.

In a further aspect, the subject is a population of cells. In a still further aspect, the subject is a population of cells latently infected with a retrovirus. In yet a further aspect, the subject is a population of cells latently infected with HIV-1.

In a further aspect, the subject is a mammal. In a still further aspect, the subject is a human. In yet a further aspect, the subject is a patient. In an even further aspect, the subject is a patient who has been diagnosed with a need for treatment of a retrovirus prior to the administering step. In a still further aspect, the subject is a patient who has been diagnosed with a need for treatment of HIV-1 prior to the administering step.

In a further aspect, the invention further comprises treating the subject with at least one agent that can be used to treat a retrovirus. In a still further aspect, the invention further comprises treating the subject with at least one agent that can be used to treat HIV-1. In yet a further aspect, the at least one agent is selected from entry inhibitors, nucleoside reverse transcriptase inhibitors (NRTIs), nucleotide reverse transcriptase inhibitors (NtRTIs), non nucleoside reverse transcriptase inhibitors (NNRTIs), protease inhibitors, integrase inhibitors, or maturation inhibitors, or a mixture thereof. In an even further aspect, the at least one agent is selected from nucleoside reverse transcriptase inhibitors (NRTIs), nucleotide reverse transcriptase inhibitors (NtRTIs), non-nucleoside reverse transcriptase inhibitors (NNRTIs), protease inhibitors, or integrase inhibitors, or a mixture thereof. In a still further aspect, the at least one agent is selected from Maraviroc, Enfuvirtide, Zidovudine, Didanosine, Zalcitabine, Stavudine, Lamivudine, Abacavir, Emtricitabine, Entecavir, Tenofovir, Adefovir, Efavirenz, Nevirapine, Delavirdine, Rilpivirine, Raltegravir, Saquinavir, Ritonavir, Indinavir, Nelfinavir, or Amprenavir, or a mixture thereof. In yet a further aspect, the at least one agent is HAART.

3. Use of Compounds and Compositions

Also provided are the uses of compounds represented by a formula:

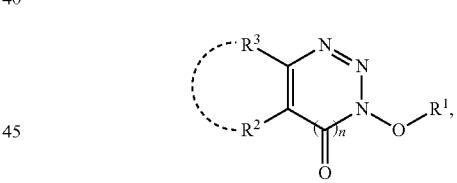

wherein n is 0 or 1, wherein $R^1$ is selected from H, C1-C4 alkyl, C1-C6 aryl, C(O)Ar, $SO_2N(CH_3)_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), or 1-(piperidin-1-ylmethylene)piperidin-1-ium hexafluorophosphate (V); wherein $R^2$ is selected from H and C1-C4 alkyl; wherein $R^3$ is selected from H and C1-C4 alkyl, or $R^2$ and $R^3$ are covalently bonded and, together with the intermediate atoms, comprise an optionally substituted fused six-membered aryl or heteroaryl ring, and compositions comprising the same.

In various aspects, the use relates to the activation of a latent retrovirus in a subject. In a further aspect, the use relates to the activation of latent HIV-1 in a subject. In a still further aspect, the subject is a population of cells. In yet a further aspect, the subject is a population of cells latently infected with a retrovirus. In an even further aspect, the subject is a population of cells latently infected with HIV-1. In a still further aspect, the subject is a mammal. In a still further aspect, the subject is a human. In yet a further aspect, the subject is a patient.

4. Kits

In one aspect, the invention relates to a kit comprising a compound represented by a formula:

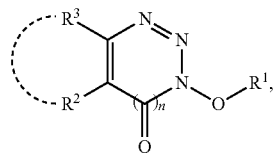

wherein n is 0 or 1; wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein $R^2$ is selected from H and C1-C4 alkyl; and wherein $R^3$ is selected from H and C1-C4 alkyl, or $R^2$ and $R^3$ are covalently bonded and, together with the intermediate atoms, comprise an optionally substituted fused six-membered aryl or heteroaryl ring and one or more of:

(a) at least one agent that can be used to treat a retrovirus;
(b) instructions for detecting a retrovirus; and
(c) instructions for treating a retrovirus.

In a further aspect, the at least one compound and the at least one agent are co-formulated. In a further aspect, the at least one compound and the at least one agent are co-packaged.

In a further aspect, the retrovirus is selected from a group comprising HIV-1, HIV-2, SIV, XMRV, HTLV-1, HTLV-2, HTLV-3, or HTLV-4. In a still further aspect, the retrovirus is HIV-1.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of compounds represented by a formula:

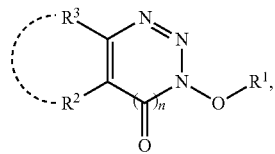

wherein n is 0 or 1; wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino)phosphonium hexafluorophosphate (V), 1-(pyrrolidin-1-ylmethylene)pyrrolidin-1-ium hexafluorophosphate (V), and 1-(piperidin-1-ylmethylene)piperidin-1-ium hexafluorophosphate (V); wherein $R^2$ is selected from H and C1-C4 alkyl; and wherein $R^3$ is selected from H and C1-C4 alkyl, or $R^2$ and $R^3$ are covalently bonded and, together with the intermediate atoms, comprise an optionally substituted fused six-membered aryl or heteroaryl ring as pharmacological tools in the development and standardization of in vitro and in vivo test systems for the evaluation of the effects of anti-retroviral latency drugs, and more particularly anti HIV-1 latency drugs, in laboratory animals such as cats, dogs, rabbits, monkeys, rats and mice, as part of the search for new therapeutic agents that activate latent retroviruses, and more specifically that activate latent HIV-1.

D. REFERENCES

Antoni B, Rabson A B, Kinter, A, Bodkin M, Poli G (1994) NF-kappa B-dependent and -independent pathways of HIV activation in a chronically infected T cell line. Virology 202:684-694.

Bosque A, Planelles V (2009) Induction of HIV-1 latency and reactivation in primary memory CD4+ T cells. Blood 113:58-65.

Bosque A, Planelles V (2010) "Studies of HIV-1 latency in an ex vivo model that uses primary central memory T cells". Methods.

Bosque A, Famiglietti M, Weyrich A S, Goulston C, Planelles V (2011) Homeostatic Proliferation Fails to Efficiently Reactivate HIV-1 Latently Infected Central Memory CD4+ T Cells. PLOS Pathog. 7(10).

Brooks D G, Kitchen S G, Kitchen C M, Scripture-Adams D D, Zack J A (2001) Generation of HIV latency during thymopoiesis. Nat Med 7:459-464.

Chun T W, Carruth L, Finzi D, et al. (1997) Quantification of latent tissue reservoirs and total body viral load in HIV-1 infection. Nature 387:183-188.

Finzi D, Hermankova M, Pierson T, et al. (1997) Identification of a reservoir for HIV-1 in patients on highly active antiretroviral therapy. Science 278:1295-1300.

Folks T M, Clouse K A, Justement J, et al. (1989) Tumor necrosis factor alpha induces expression of human immunodeficiency virus in a chronically infected T-cell clone. Proc Natl Acad Sci USA 86:2365-2368.

Folks T M, Justement J, Kinter A, Dinarello C A, Fauci A S (1987) Cytokine-induced expression of HIV-1 in a chronically infected promonocyte cell line. Science 238:800-802.

Jordan A, Bisgrove D, Verdin E (2003) HIV reproducibly establishes a latent infection after acute infection of T cells in vitro. Embo J 22:1868-1877.

Planelles V, Bosque A, Methods and compositions relating to viral latency, U.S. Patent Application 2010/0291067 A1, November 2010.

E. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Methods

A novel primary cell model for the study of HIV-1 latency was adapted so as to be suitable for high-throughput screening (HTS) of new compounds that may reactivate HIV-1 from its latency state (Bosque and Planelles, 2009; Bosque and Planelles, 2010; and patent application: Methods and compositions relating to viral latency, Planelles V, Basque A, U.S. Patent Application 2010/0291067 A1, November 2010).

To facilitate HTS, the nef gene was replaced with that encoding the green fluorescent protein (GFP). It was confirmed that deletion of nef has no effect in latency/reactivation (Bosque and Planelles, 2009) and that using GFP provides a faster, more economical, and equally sensitive, as compared to intracellular p24 detection, readout.

The reactivation experiments were modified to be performed in 96-well plates, utilizing 100,000 cells per well. After reactivation, flow cytometric analysis was performed with Becton Dickinson FACSCanto II with a High Throughput Sampler (HTS) for microtiter plates that is available through the Flow Cytometry Core Facility at the University of Utah. It takes about 30 minutes to analyze a plate, when acquiring 10,000 cells per well. Analysis for each well includes (a) green fluorescence as a direct indicator of viral reactivation; and (b) forward and side scatter as general measures of cell morphology, which is a gross indication of viability.

2. Activation of Latent HIV-1 in Latently Infected Cultured $T_{CM}$

Figure 1B:
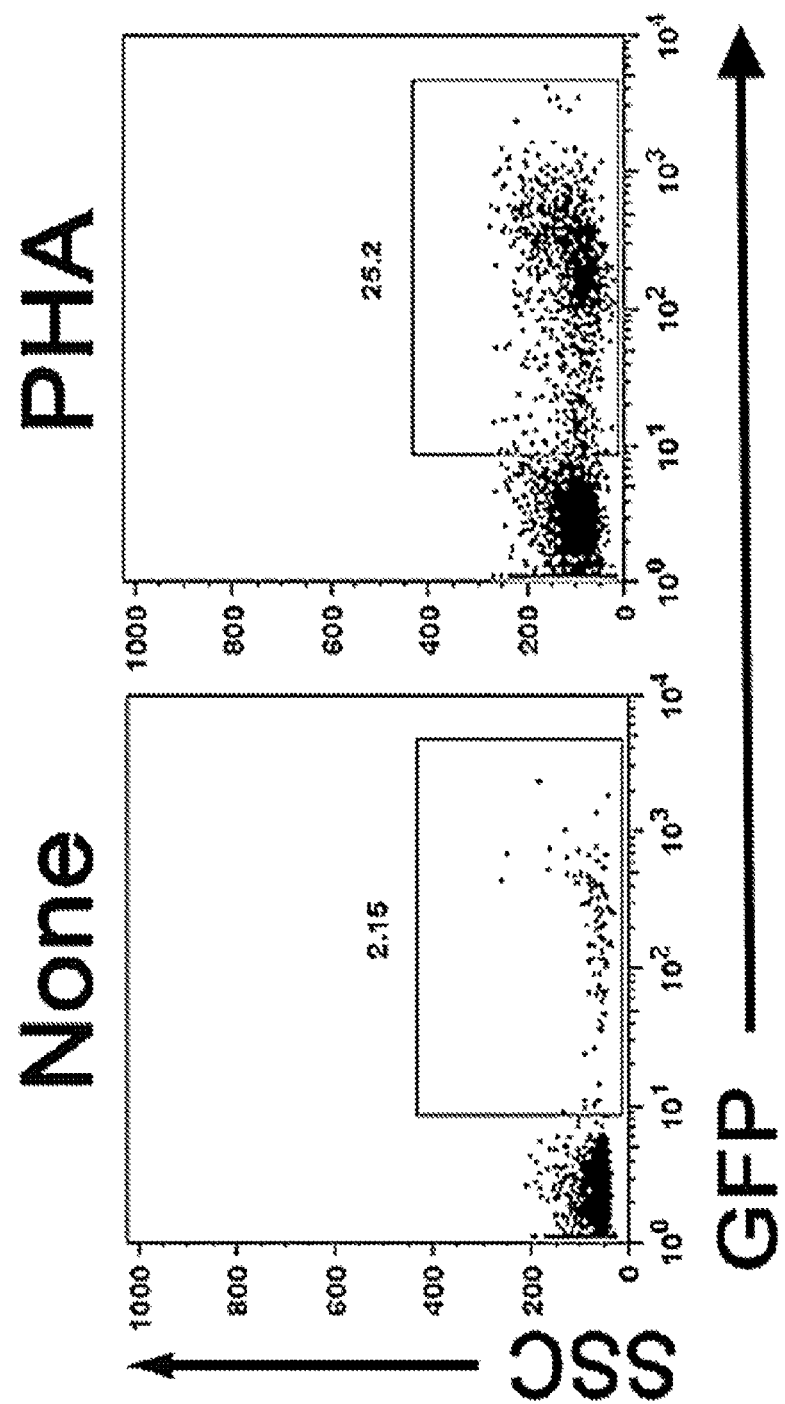
FIG. 1B shows that Plate II well C07 activates latent HIV-1 as indicated by an increase in fluorescence compared to the control.
Figure 1B:
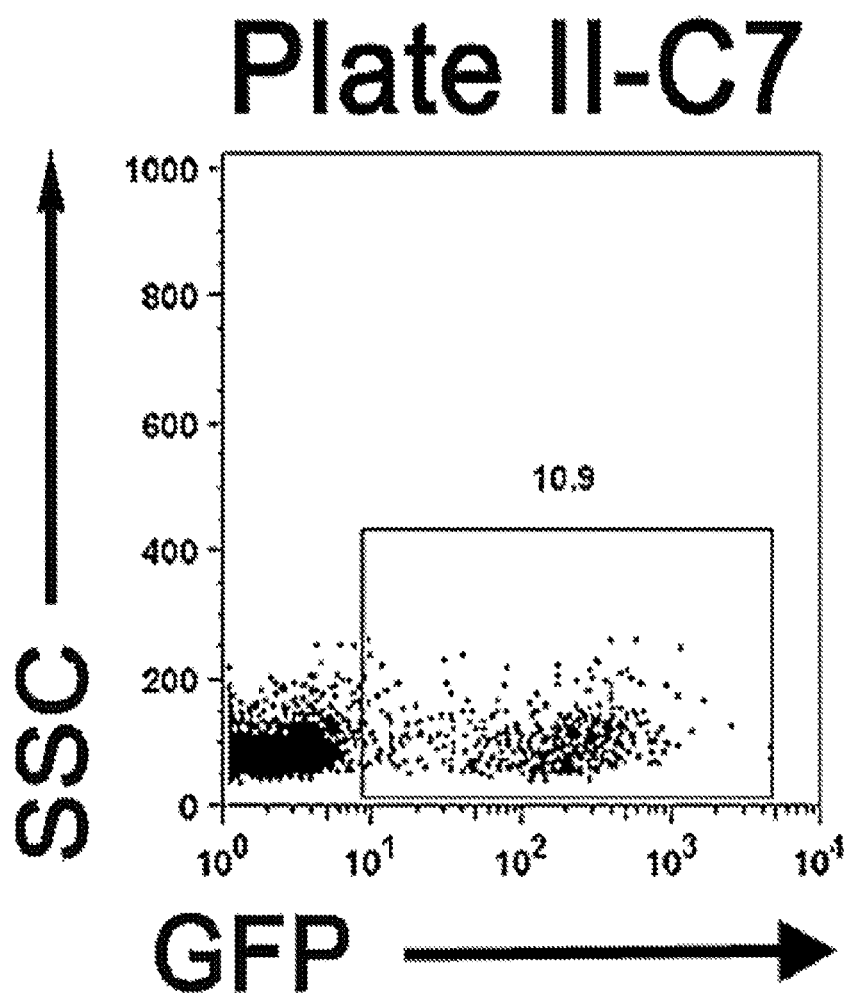

Latently infected cells were generated using healthy, uninfected DONOR 78 cells that were infected with DHIV virus. Reactivation was monitored by analysis of GFP by Flow Cytometry 72 hours after stimulation. Beads coated with anti-CD3/anti CD28 (CD3/CD28) were used as a positive reactivation stimulus. Reactivation was done in a 96-well plate round bottom. Screening of the Ireland Natural Product Collection, a set of natural products isolated from marine invertebrate animals and microorganisms, resulted in a positive hit in Plate 2 well C7 (FIGS. 1A and 1B). This compound is an intermediate en route to synthesis of a cyclic peptide isolated from a tunicate.

Figure 1C:
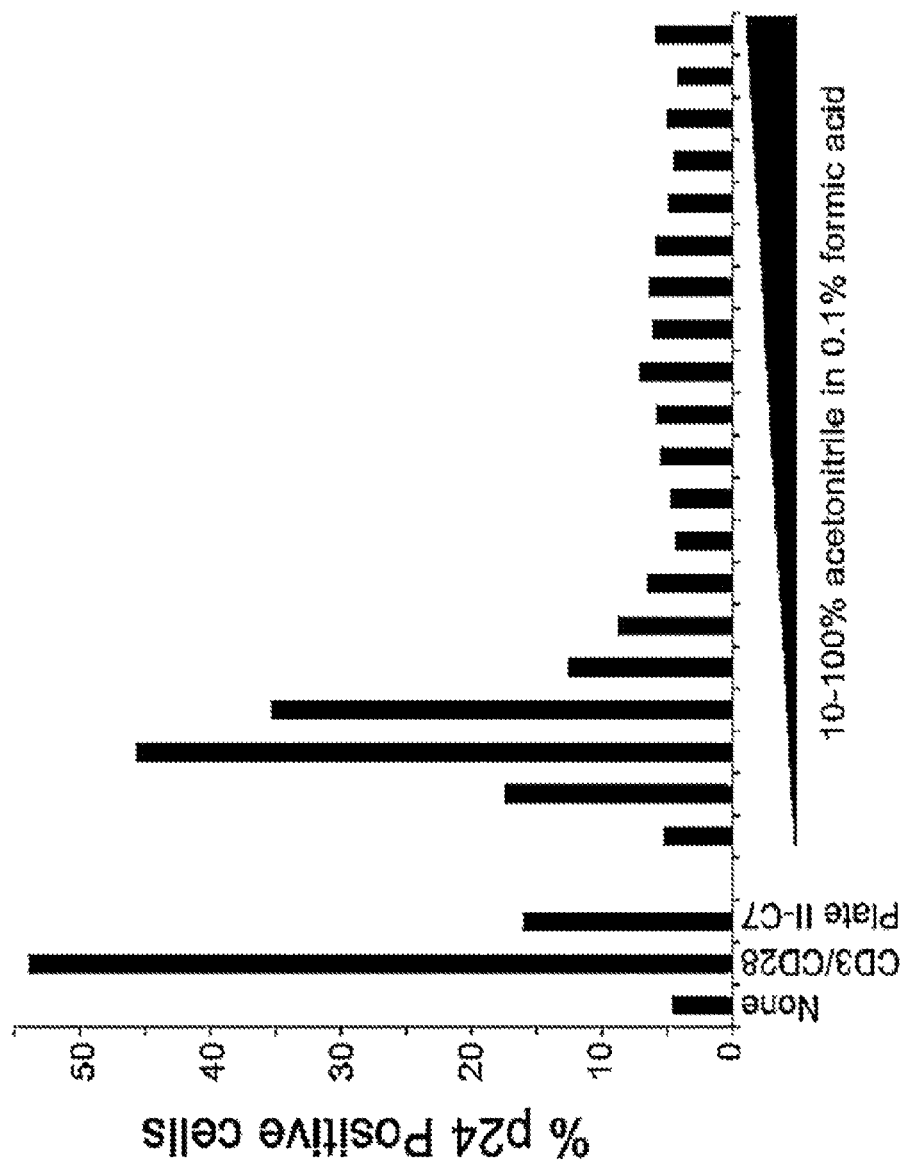
FIG. 1C shows the % of positive cells and the % of reactivation compared to the positive control for 20 fractions of C07. The fractions were separated using HPLC with a gradient of 10-100% in acetonitrile with 0.1% formic acid. The activity of CD3/CD28 is shown as a positive control. The ability of C07 (MNP-II C07) to activate latent HIV-1 is also displayed.
Figure 1D:
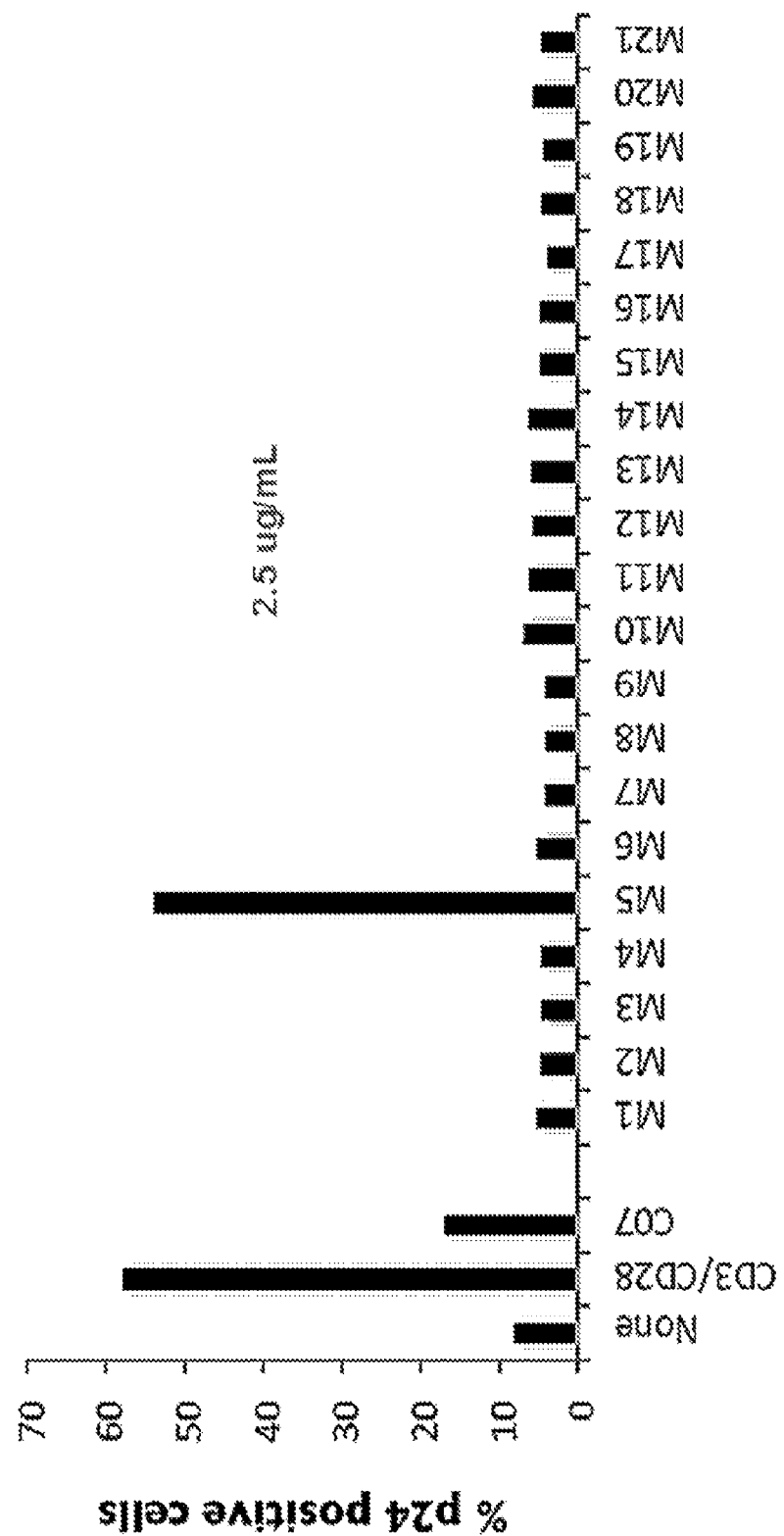
FIG. 1D shows that the compound responsible for the activity of C07 is located in fraction M5. The major component of this fraction is 1-hydroxybenzotriazole (HOBt).
Figure 1E:
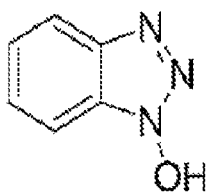
FIG. 1E shows the structure of HOBt.
Figure 1F:
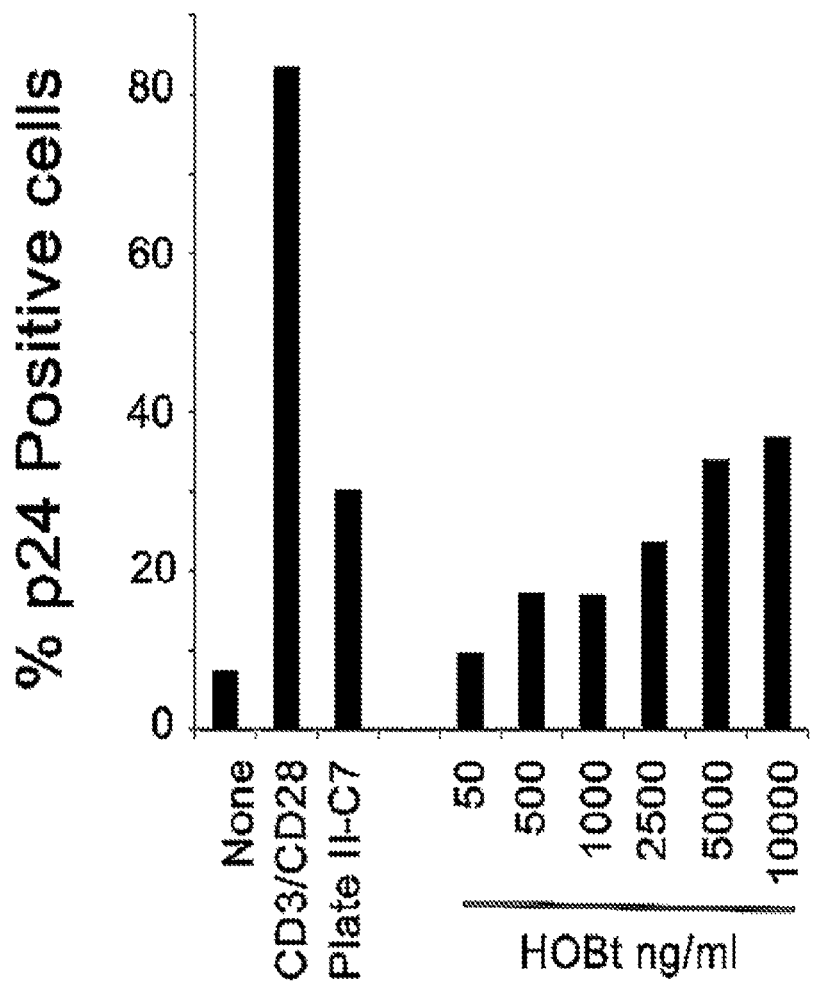
FIG. 1F shows that HOBt reactivates HIV-1 latency in a dose dependent manner.
Figure 1G:
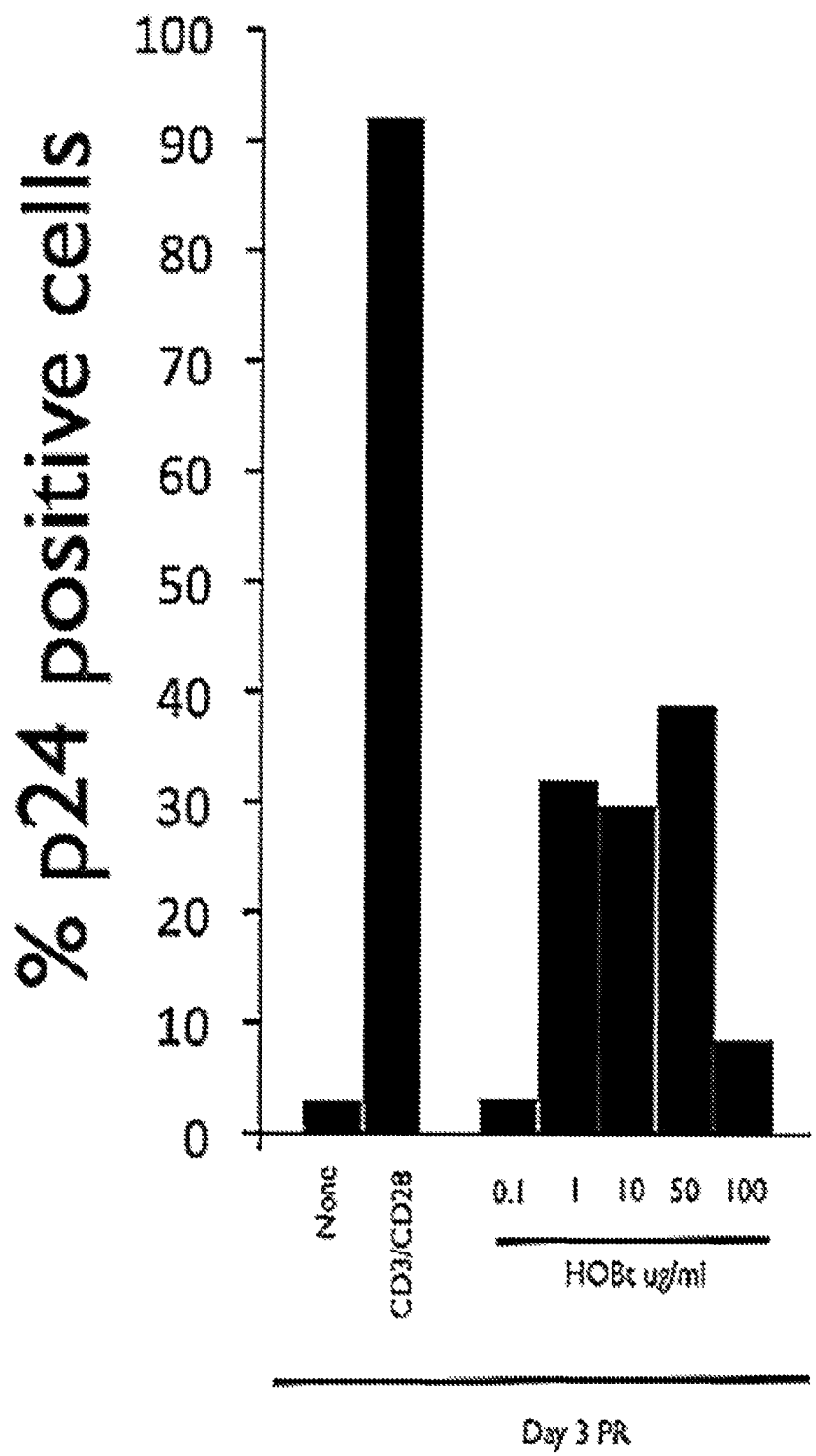
FIG. 1G shows that HOBt is able to reactive HIV-1 latency with slower kinetics compared to anti-CD3/CD28.
Figure 1G:
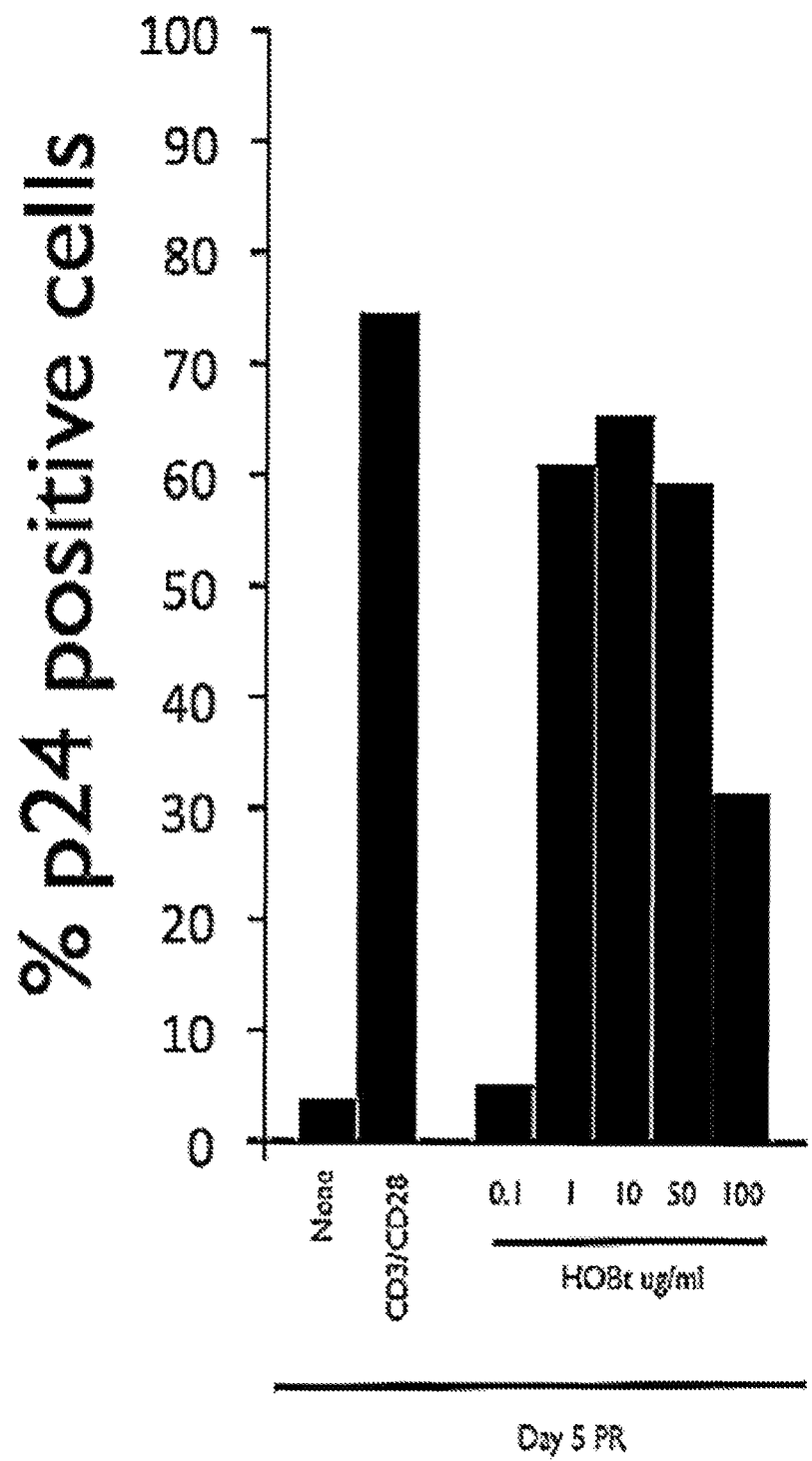
Figure 1G:
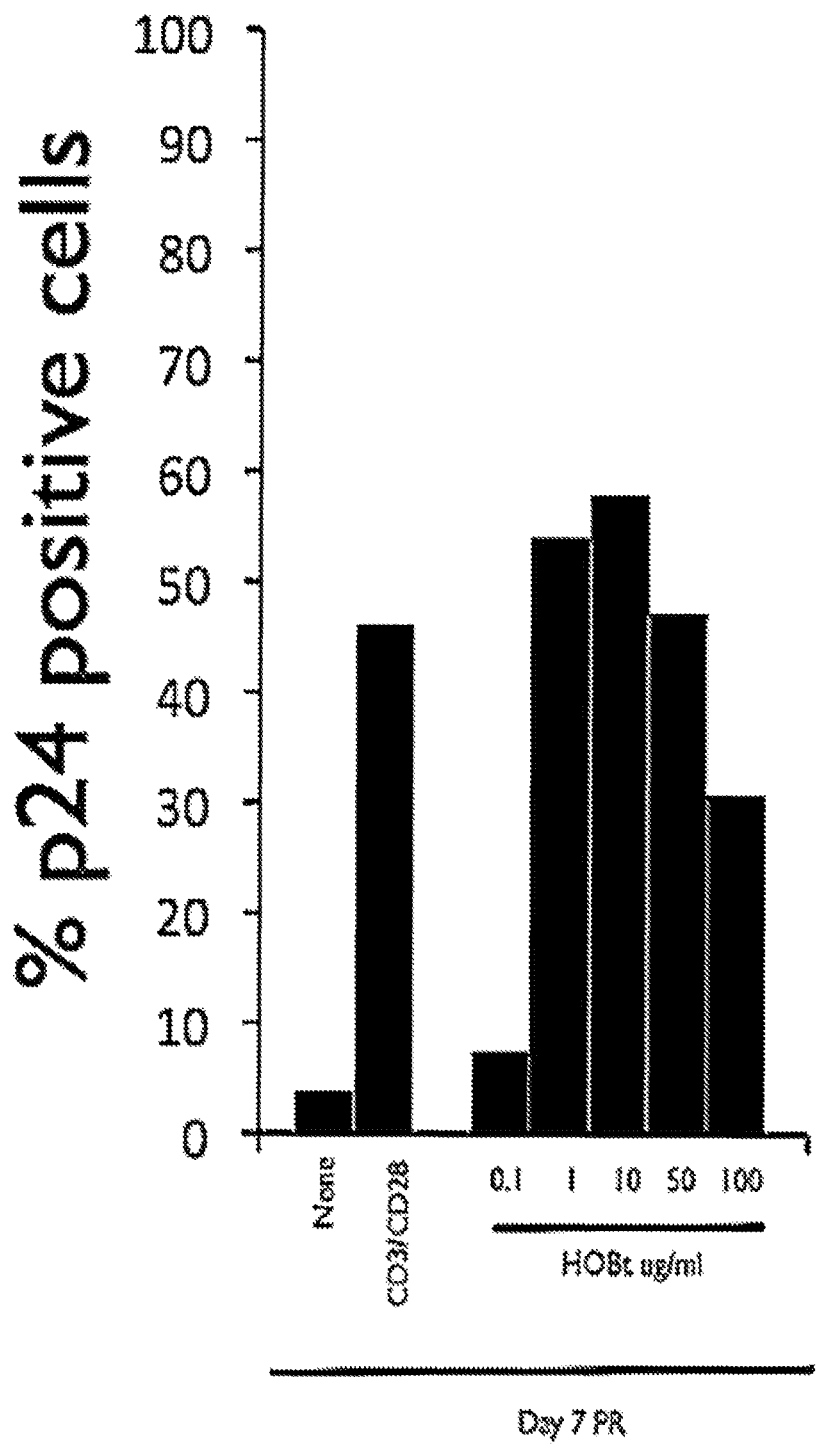

HPLC was used to generate 20 fractions based on elution time using a gradient from 10-100% acetonitrile in 0.1% formic acid using a Phenomenex Kinetic C18 50×2.10 mm column (2.6 µM, 100 A). The ability of these fractions to activate HIV-1 was tested and compared in parallel with the original hit. FIG. 1C shows the % of p24 positive cells in the Y-axis and the % of reactivation compared to the positive control (beads coated with anti-CD3/anti-CD28) at the top of each bar. This data reveals that the active compound is enriched in fractions 2 and 3. Further fractionation of C7 was performed and each fraction tested at the concentration indicated in the graph (FIG. 1D). The active component is found in fraction M5. This fraction was found to be enriched in 1-hydroxybenzotriazol (HOBt) (FIG. 1E). The ability of HOBt to activate latent HIV-1 in a dose-dependent manner compared to C7 was also established (FIG. 1F). Finally, HOBt was tested at different concentrations and analyzed on either Day 3, Day 5, or Day 7. When compared with anti-CD3/CD28, a non-druggable treatment due to its side effects, HOBt was found to reactive HIV-1 latency with slower kinetics (FIG. 1G).

3. Activation of Latent HIV-1 by Additional Analogs

Figure 2A:
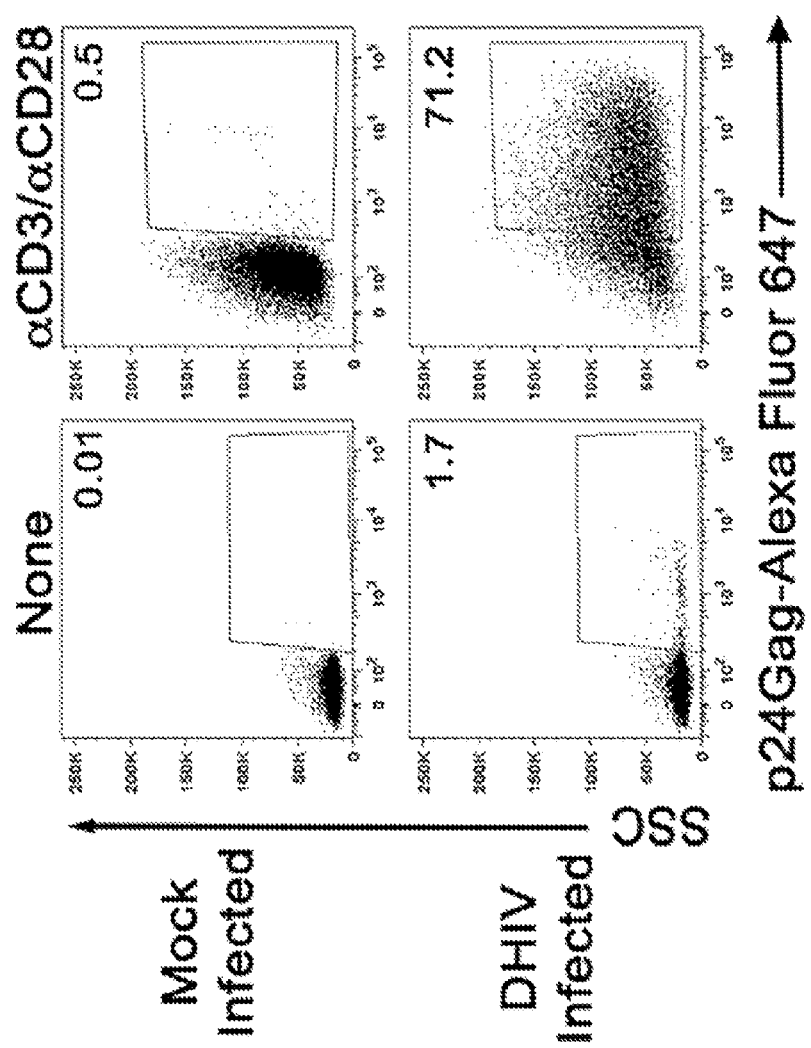
FIG. 2A shows the ability of HOBt and HOBt analogs to activate latent HIV-1. In addition to HOBt, HOAt also activates HIV-1 latent cells.
Figure 2A:
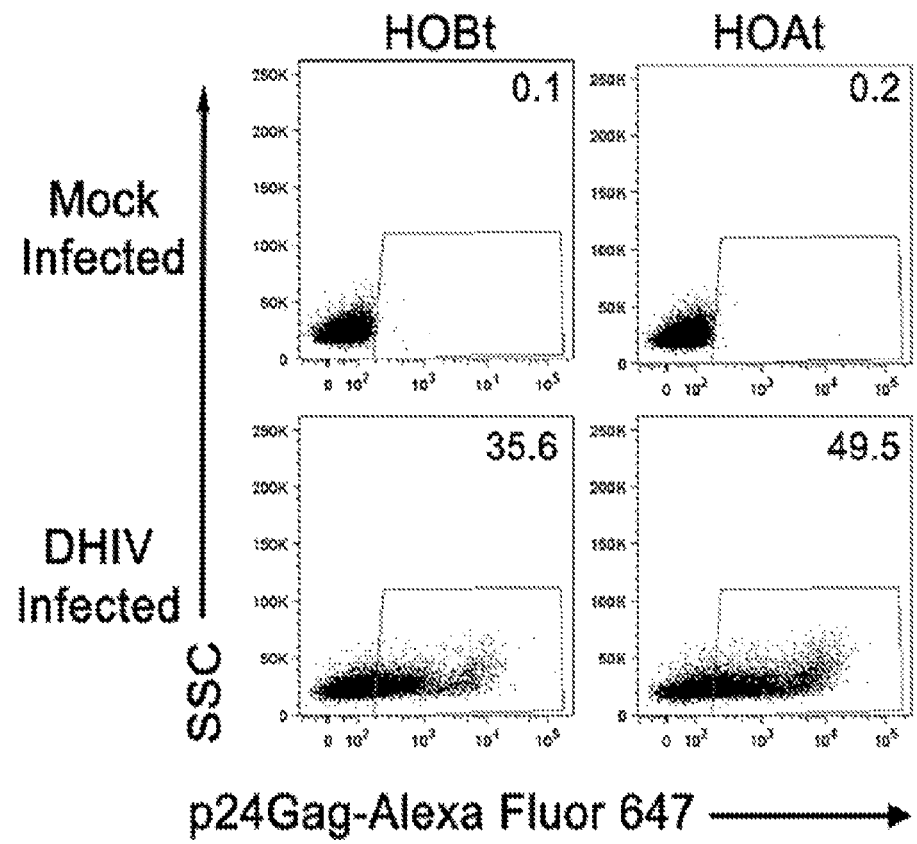
Figure 2A:
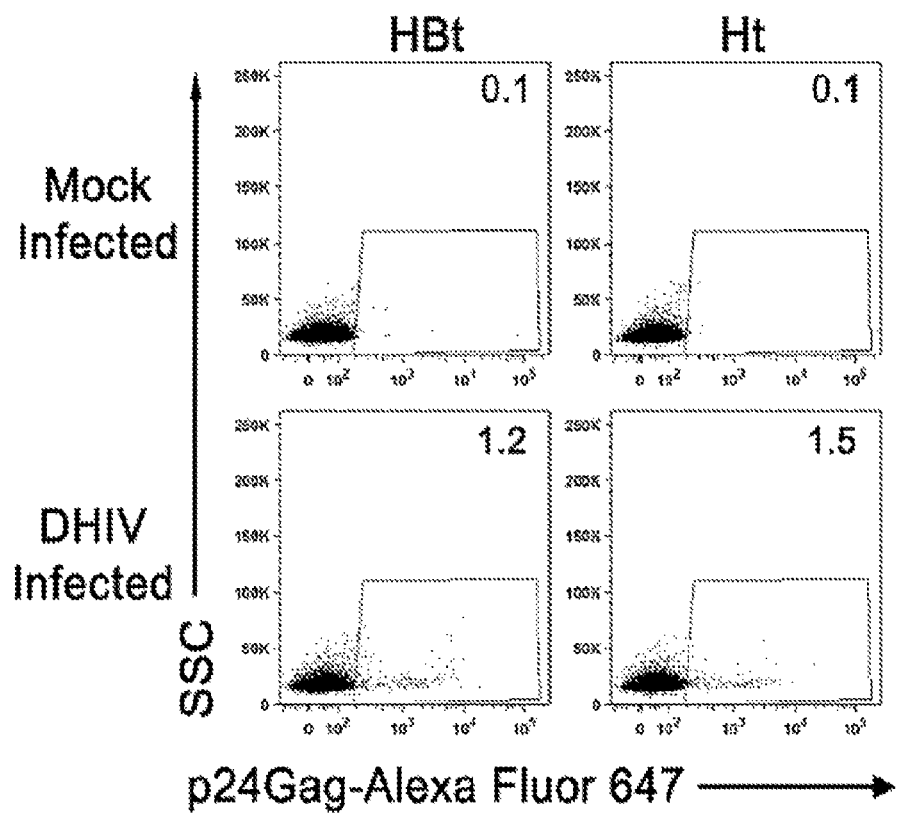
Figure 2A:
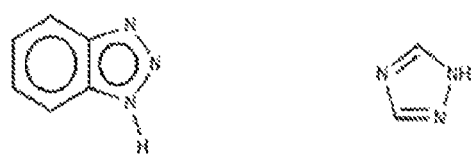
Figure 2A:
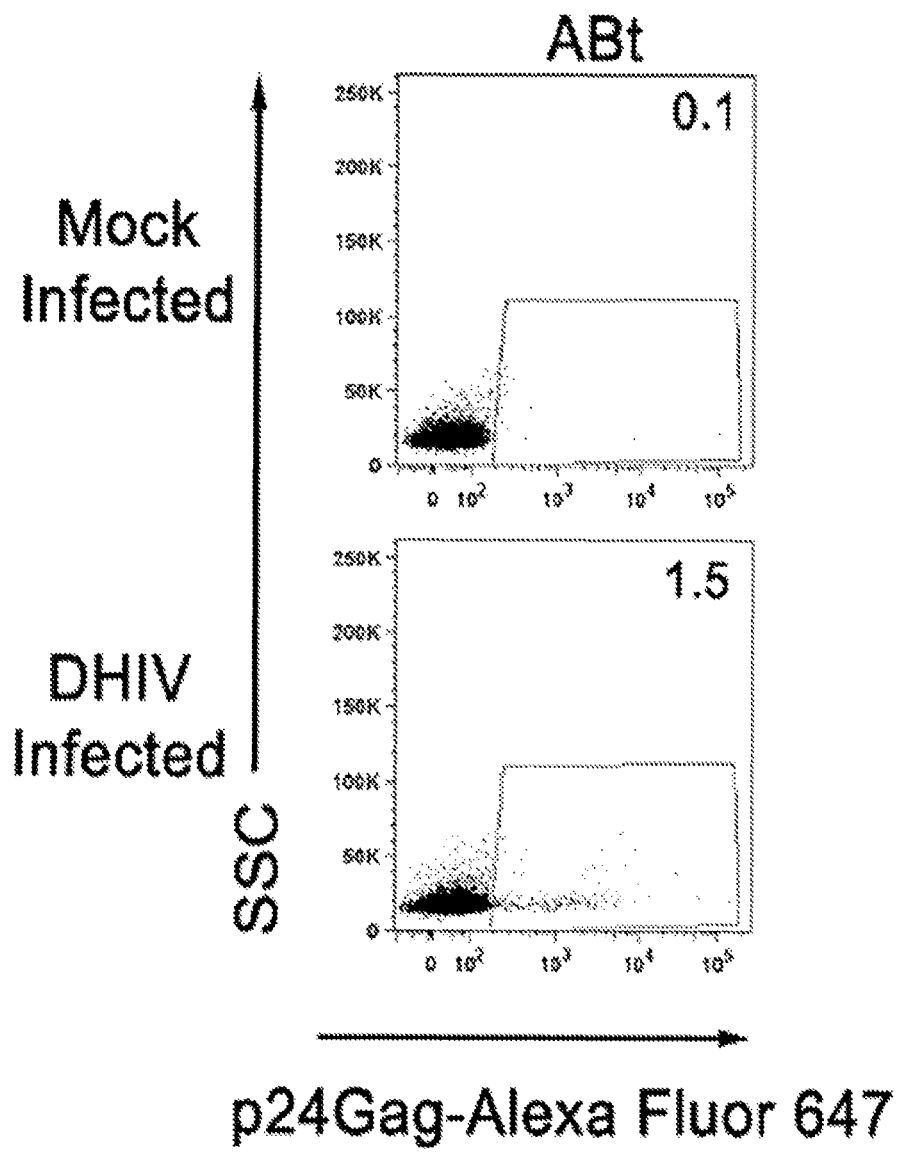
Figure 2B:
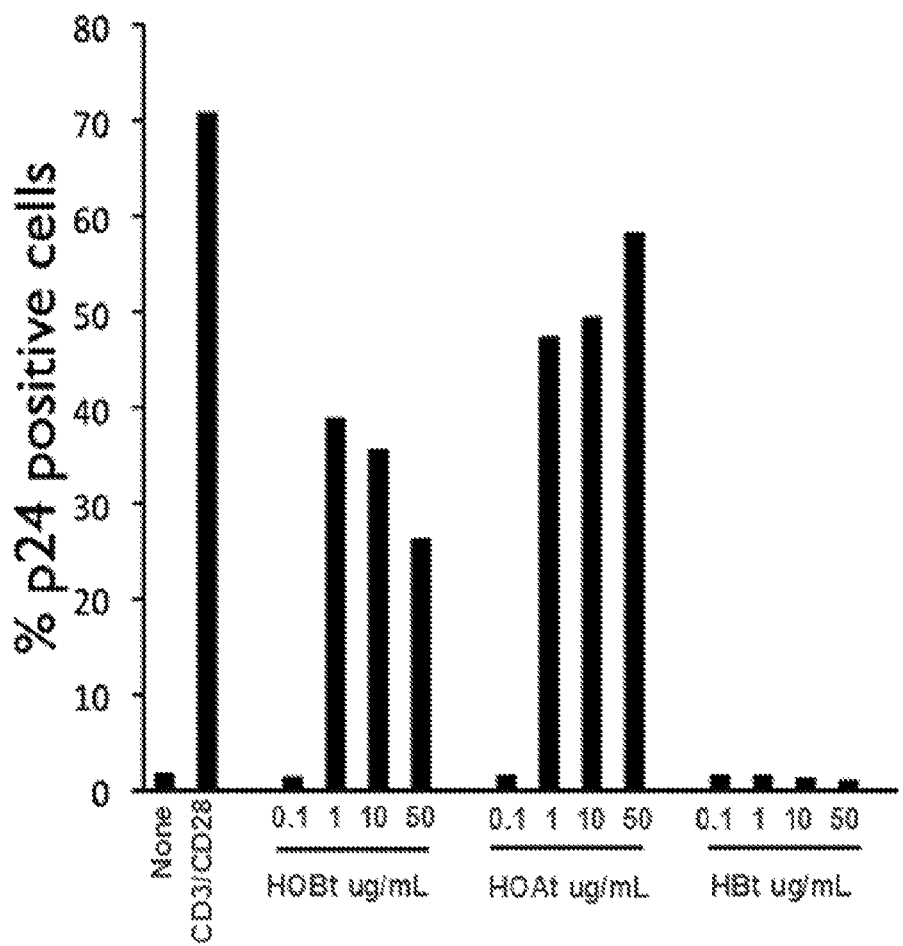
FIG. 2B shows that both HOBt and HOAt activate latent HIV-1.
Figure 2B:
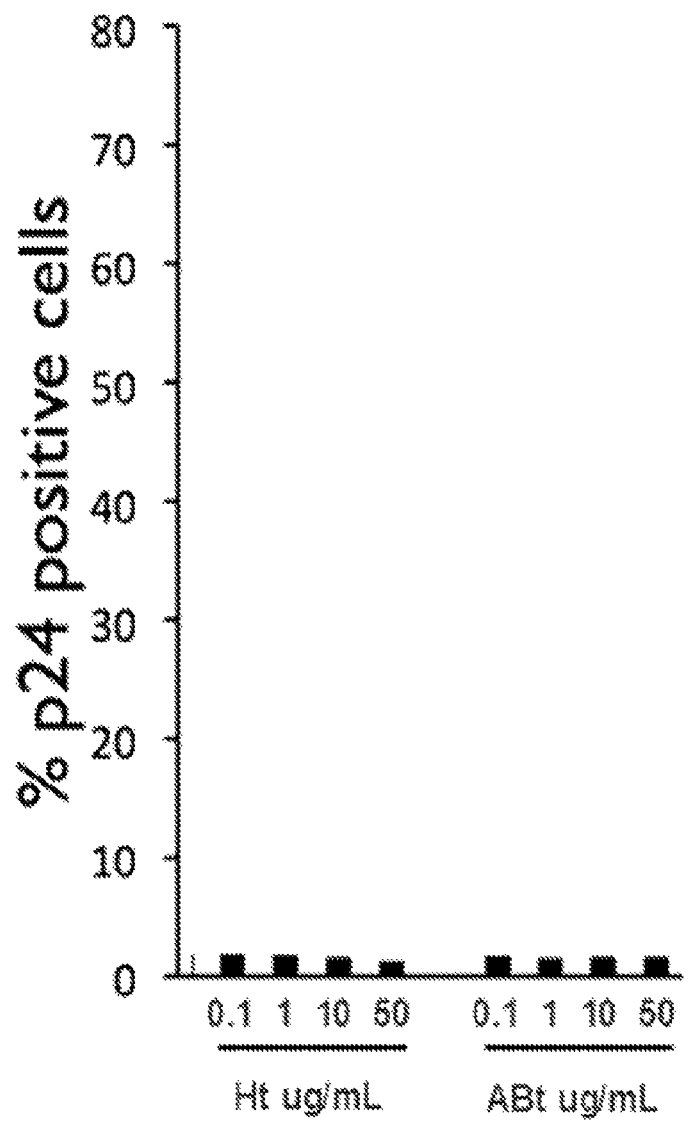
Figure 2B:
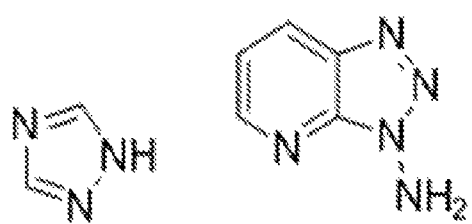
Figure 2C:
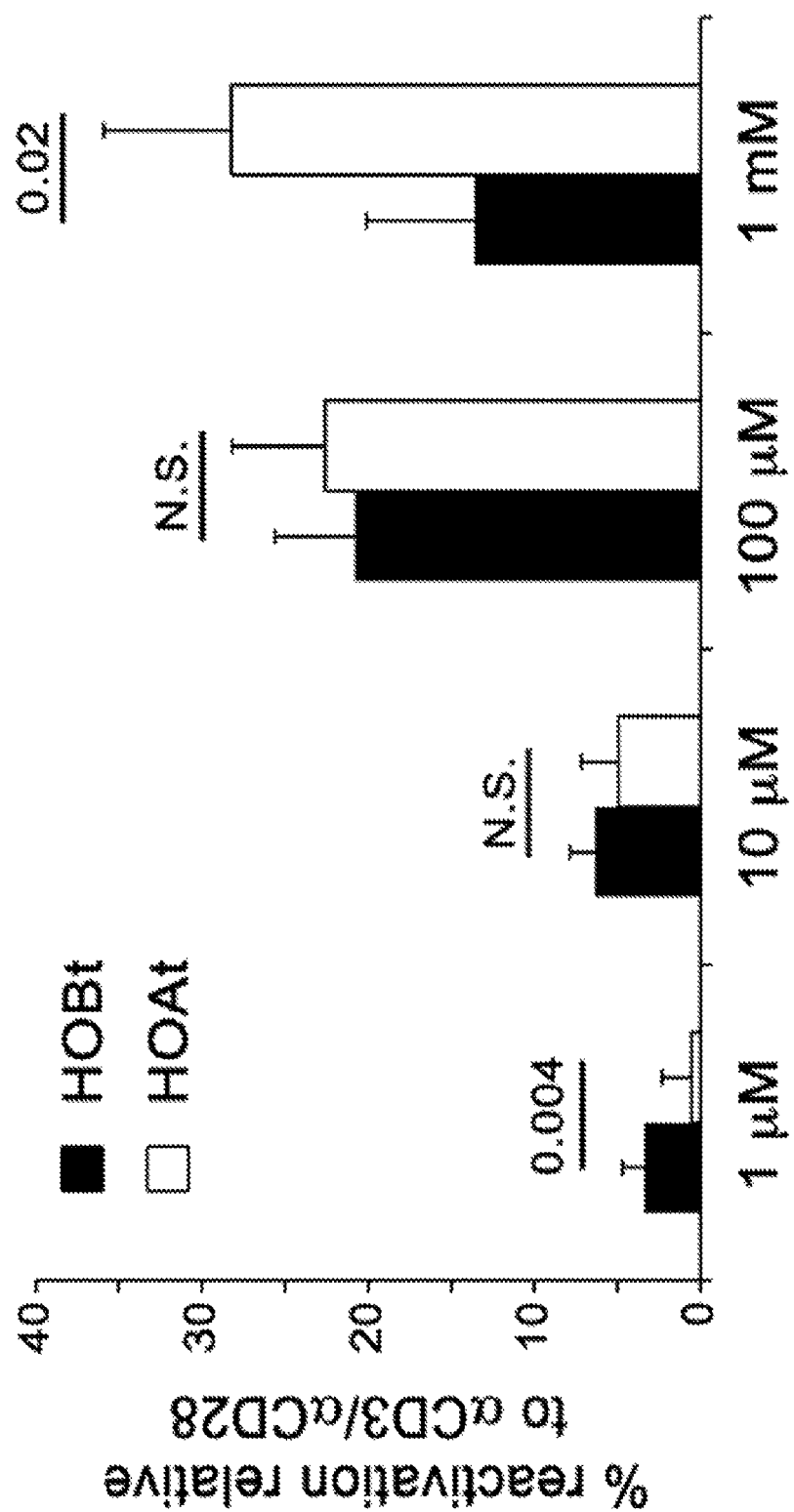
FIG. 2C shows that HOBt and HOAt reactivate HIV-1 latency in a dose dependent manner.

The ability of additional triazole analogs including benzotriazole (HBO, 1-hydroxy-7-amino benzotriazole (HOAt), triazole (Ht) and 1-aminobenzotriazole (ABt) to activate latent HIV-1 was also tested (Table 2). Latently infected cells were generated using healthy, uninfected DONOR 78 cells that were infected with DHIV virus. Reactivation was monitored by analysis of p24Gag by Flow Cytometry 72 hours after stimulation. It was demonstrated that both HOBt and HOAt were able to reactivate HIV-1 latency (FIGS. 2A and 2C). The activity of both analogs is dose dependent (FIG. 2C).

TABLE 2

| Compound | Structure |
|---|---|
| HOBt | [benzotriazole with N-OH] |
| HOAt | [7-aza-benzotriazole with N-OH] |
| 6Cl—HOBt | [6-chloro-benzotriazole with N-OH] |
| HBt | [benzotriazole with N-H] |
| ABt | [benzotriazole with N-NH₂] |
| Triazole | [1,2,3-triazole with NH] |
| HO-DhBt | [3-hydroxy-1,2,3-benzotriazin-4(3H)-one] |
| HATU | [HATU structure with PF₆⁻ counterion] |

TABLE 2-continued

| Compound | Structure |
|---|---|
| Pyridozine | (structure: methyl-substituted dihydropyridazinone linked to benzotriazole-N-OH) |

Figure 2D:
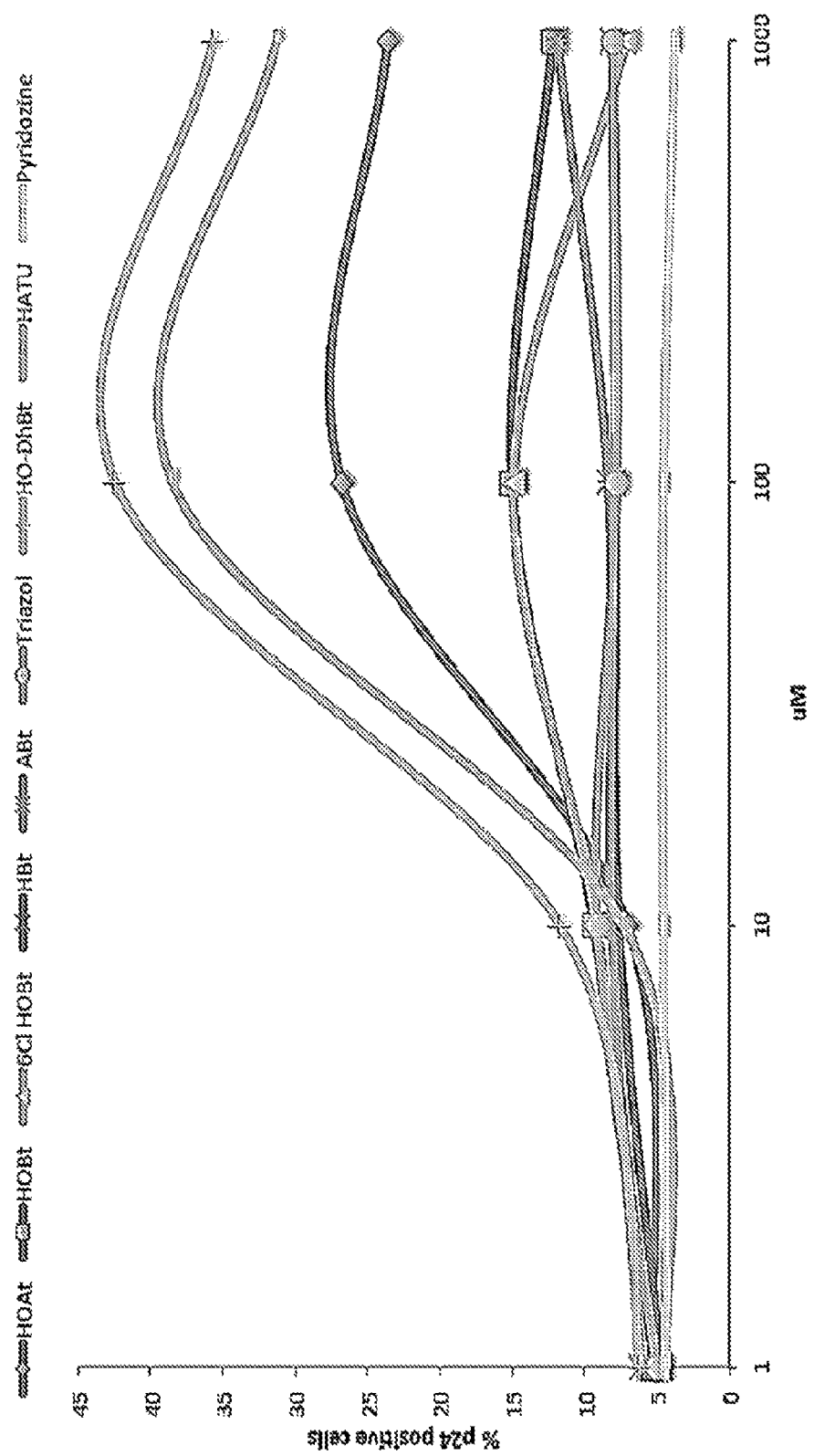
FIG. 2D shows the ability of a panel of 7 derivatives of HOBt to activate latent HIV-1. HOAt demonstrates increased activity compared to HOBt. Two additional analogs, HATU and HO-DhBt, also illustrate an increased ability to induce viral reactivation in a dose dependent manner.

A panel of 7 derivatives of the original hit, HOBt, were tested for their ability to activate latent HIV-1 (FIG. 2D). HOAt is a more potent analog than the original hit. Two additional compounds, HATU and HO-DhBt, were also able to induce viral reactivation in a dose dependent manner and with increased efficiency.

4. Synergistic Effect of Several Γ-Cytokines

Figure 3:
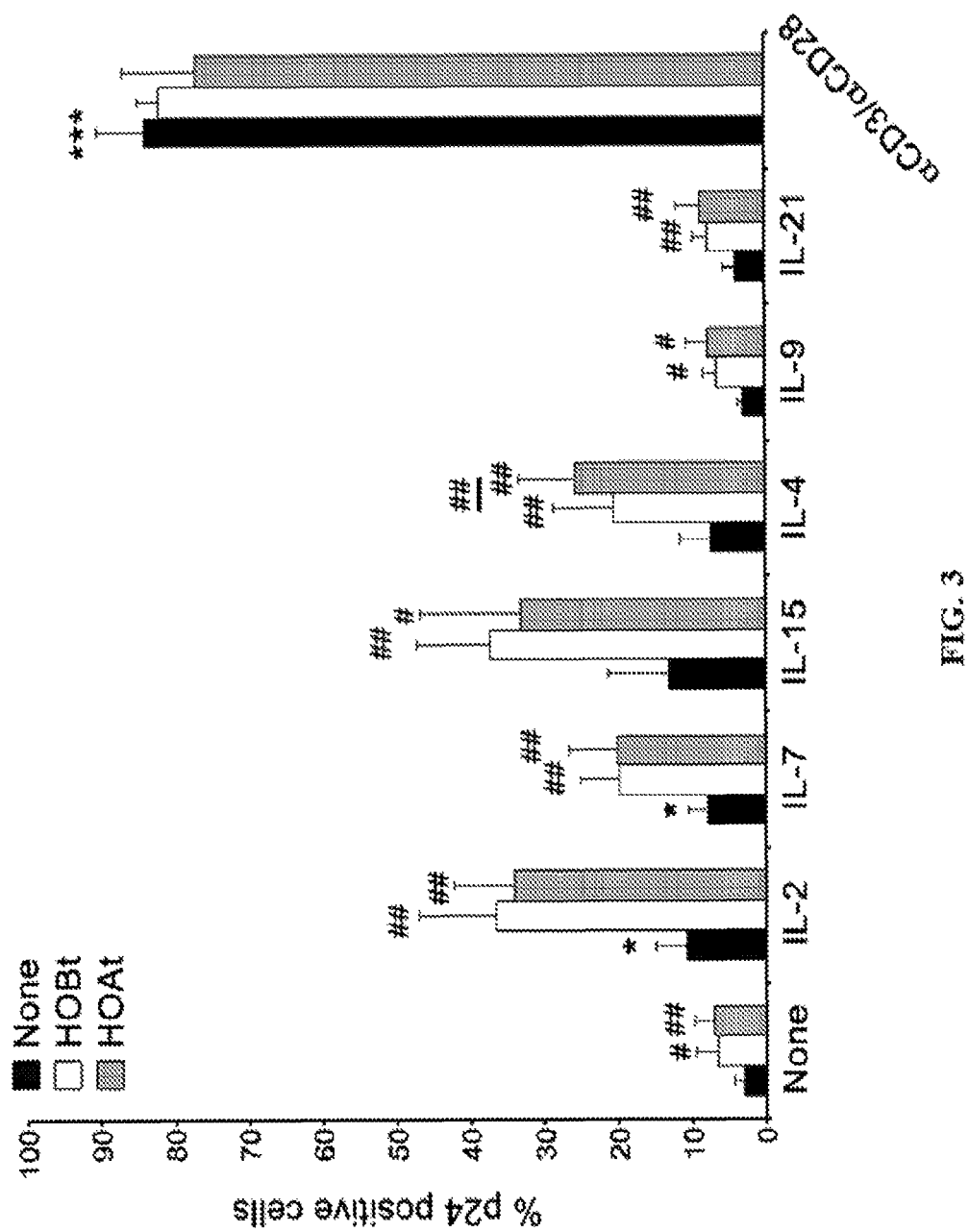
FIG. 3 shows that HOBt and HOAt synergize with several γc-cytokines to reactivate HIV-1 latency. HOBt and HOAt increase viral reactivation in the presence of IL-2, IL-7 and IL-5. IL-4 did not induce viral reactivation by itself; however, combining IL-4 with either HOBt or HOAt did induce significant viral reactivation. IL-9 and IL-21 show no effect.

Latently infected cells were generated using healthy, uninfected DONOR 78 cells that were infected with DHIV virus. Reactivation was monitored by analysis of p24Gag by Flow Cytometry 72 hours after stimulation. HOBt was tested in the presence or absence of IL-2, a γc-cytokine required for survival of the cells in vivo. The ability of HOBt and HOAt to activate latent HIV-1 in the absence of IL-2 or in the presence of different γc-cytokines, e.g. IL-4, IL-7, IL-15, IL-9, and IL-21, was tested (FIG. 3). In the absence of γc-cytokines both analogs have the ability to significantly reactivate HIV-1 latency. When compared with incubation of the cells in the absence of cytokines, IL-2 and IL-7 trend towards increasing viral reactivation. HOBt and HOAt dramatically increase viral reactivation in the presence of all, IL-2, IL-4, and IL-15. IL-4 was not able to induce significant viral reactivation by itself; however, combination of IL-4 with either HOBt or HOAt induced significant viral reactivation. Finally, IL-9 and IL-21 did not have an effect in viral reactivation wither alone or in combination with HOBt and HOAt.

5. Activation of Latent HIV-1 in a Stat5 Dependent Manner

Figure 4A:
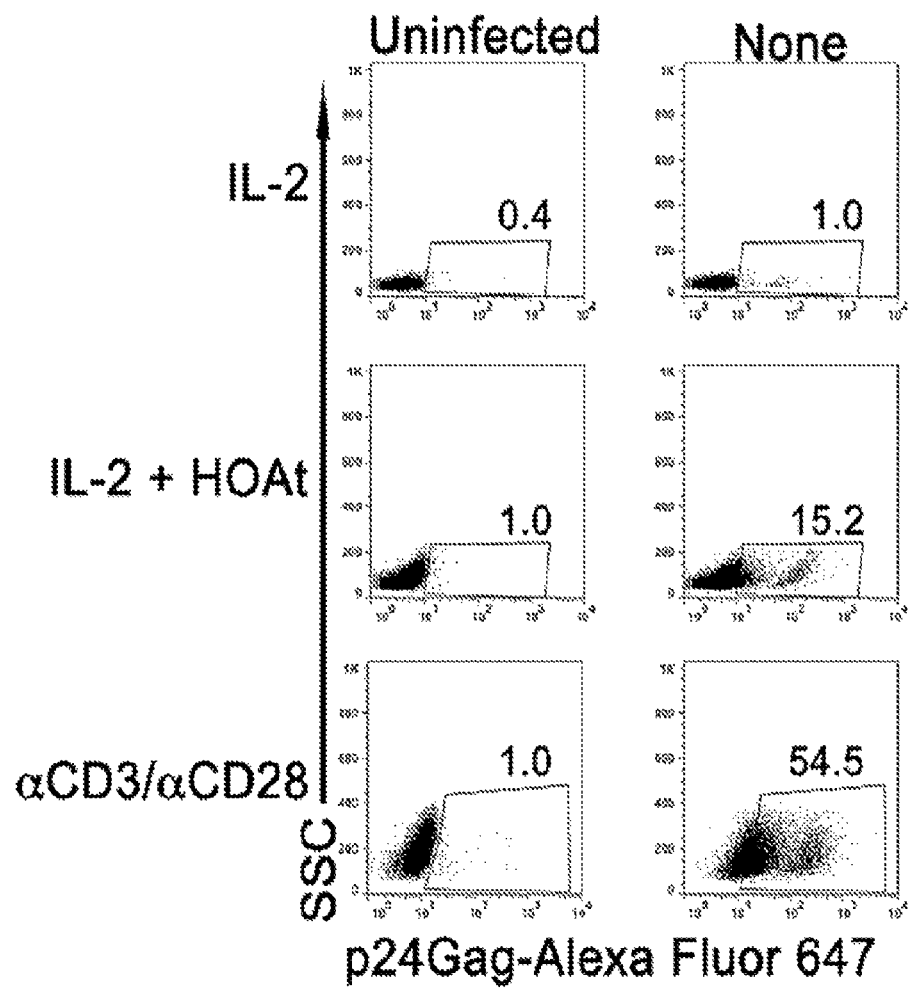
FIG. 4A shows that HOAt induces viral reactivation in a STAT5 dependent manner. Inhibition of either NFAT or NF-κB did not have an effect on viral reactivation by HOAt. Inhibition of JAK selectively blocked viral reactivation by HOAt but not by αCD3/αCD28. While the STAT3 inhibitor did not have a significant effect, the STAT5 inhibitor was able to completely prevent activation of latent HIV-1 by HOAt.
Figure 4A:
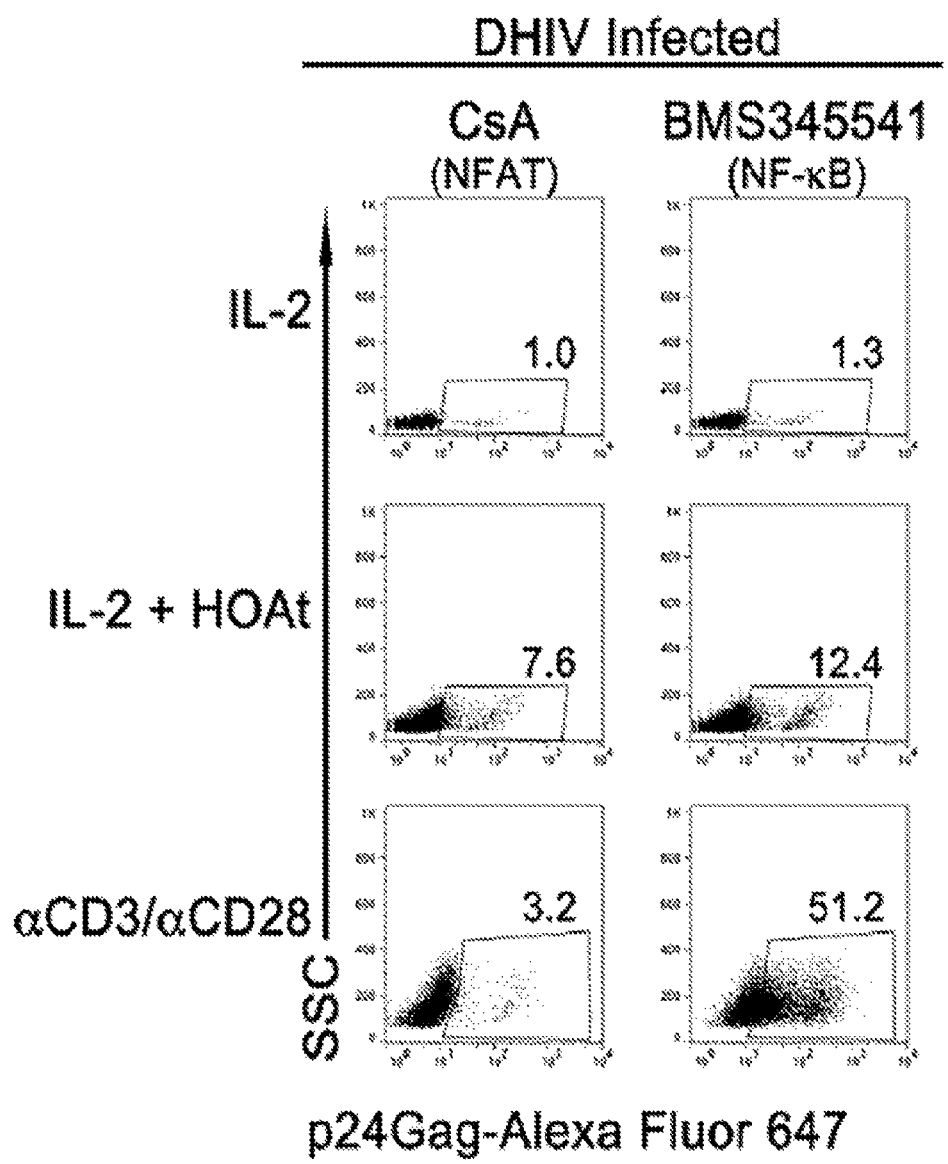
Figure 4A:
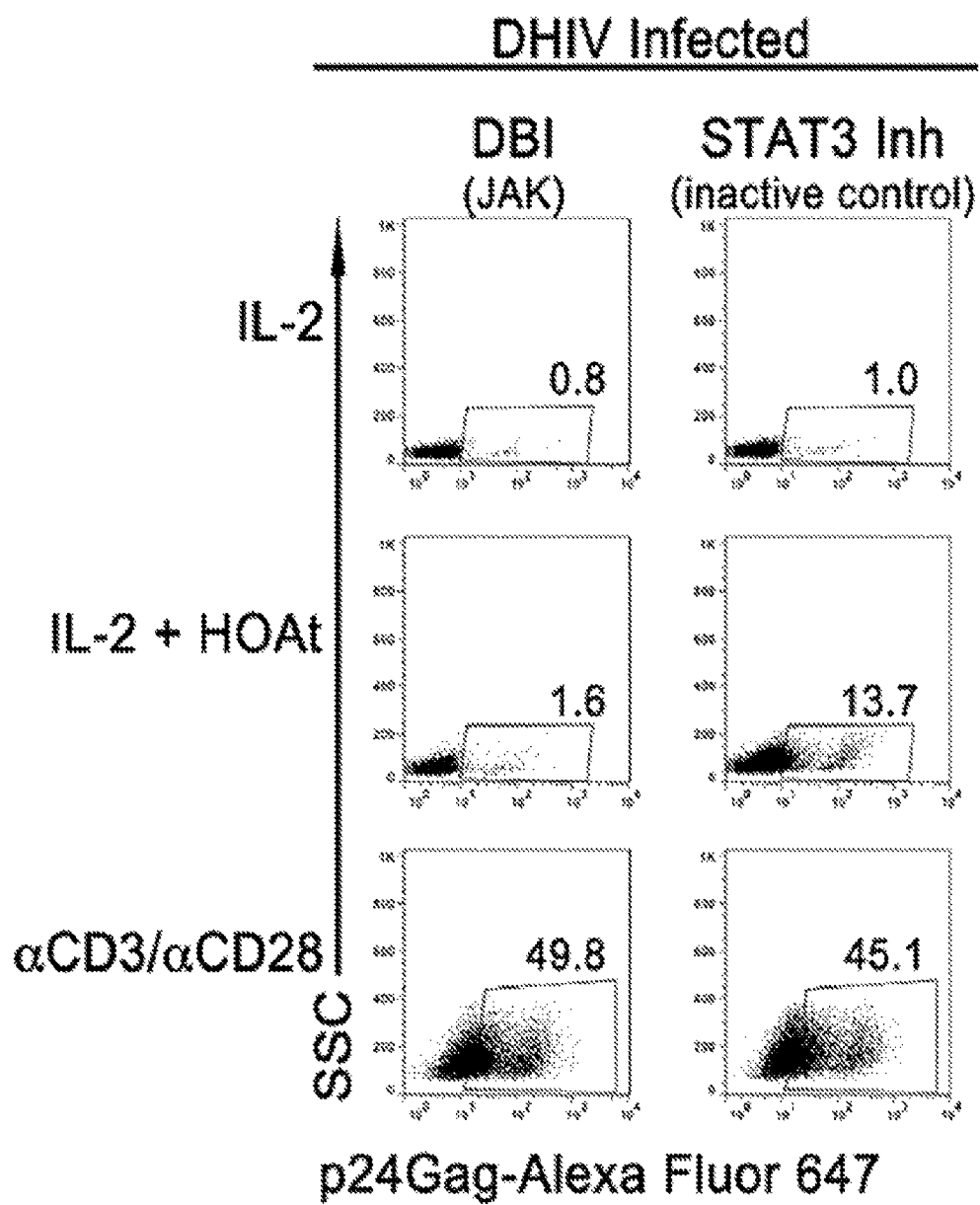
Figure 4A:
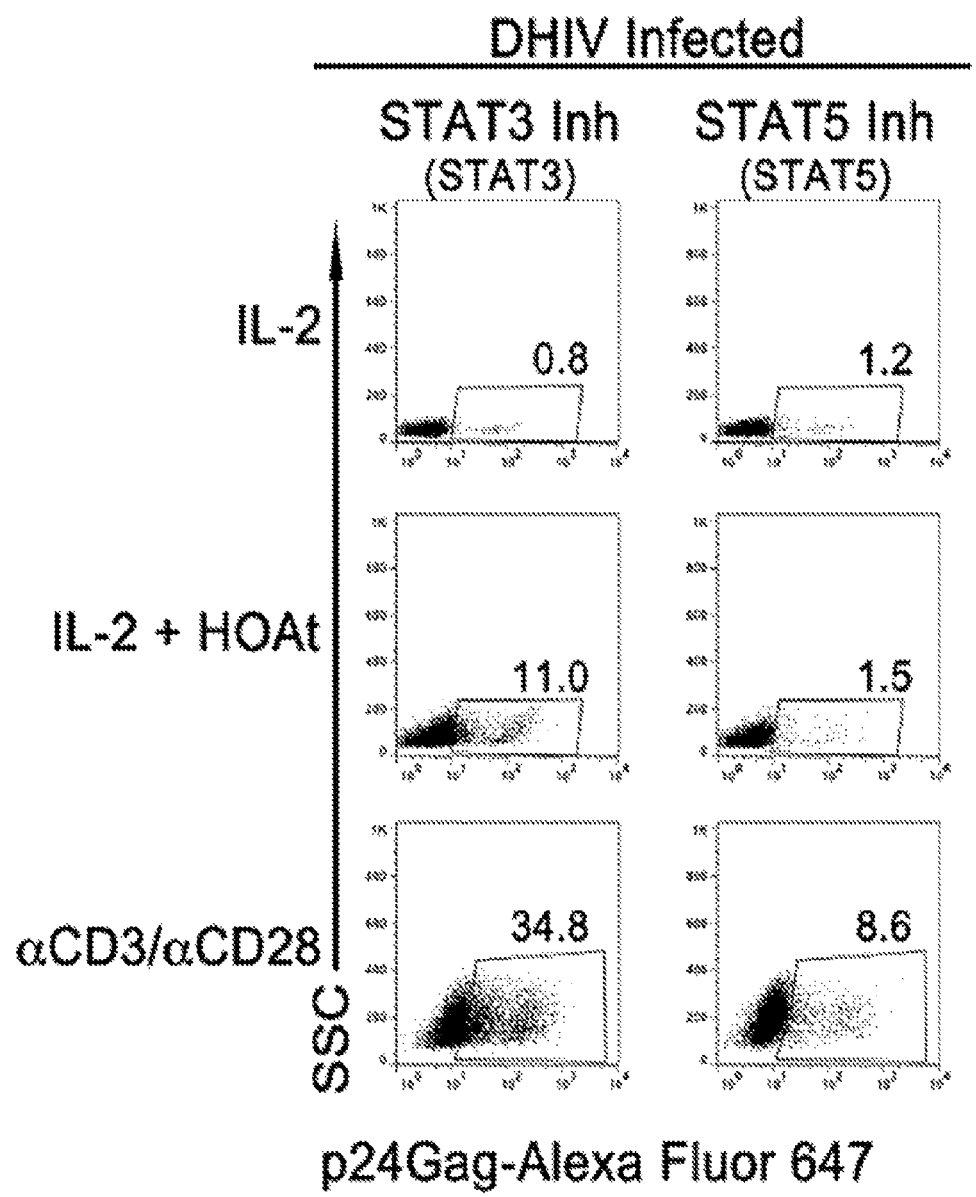

The ability of chemical inhibitors of known signaling pathways to block viral reactivation mediated by HOAt was examined (FIG. 4A). Blocking either NFAT or NF-κB with either Cyclosporine A (CsA) or BMS345541 did not have a significant effect on viral reactivation induced by HOAt. CsA is able to block viral reactivation induced by αCD3/αCD28. The JAK inhibitor DBI strongly blocks viral reactivation mediated by HOAt but not by αCD3/αCD28. Activation of JAK kinases lead to the activation of the transcription factors STATs. Specific inhibitors of STAT3 and STAT5 were thus also studied. The STAT3 inhibitor peptide used did not have a significant effect in viral reactivation compared with an inactive control peptide. In the other hand, the STAT5 inhibitor completely abrogates viral reactivation induced by HOAt.

Figure 4B:
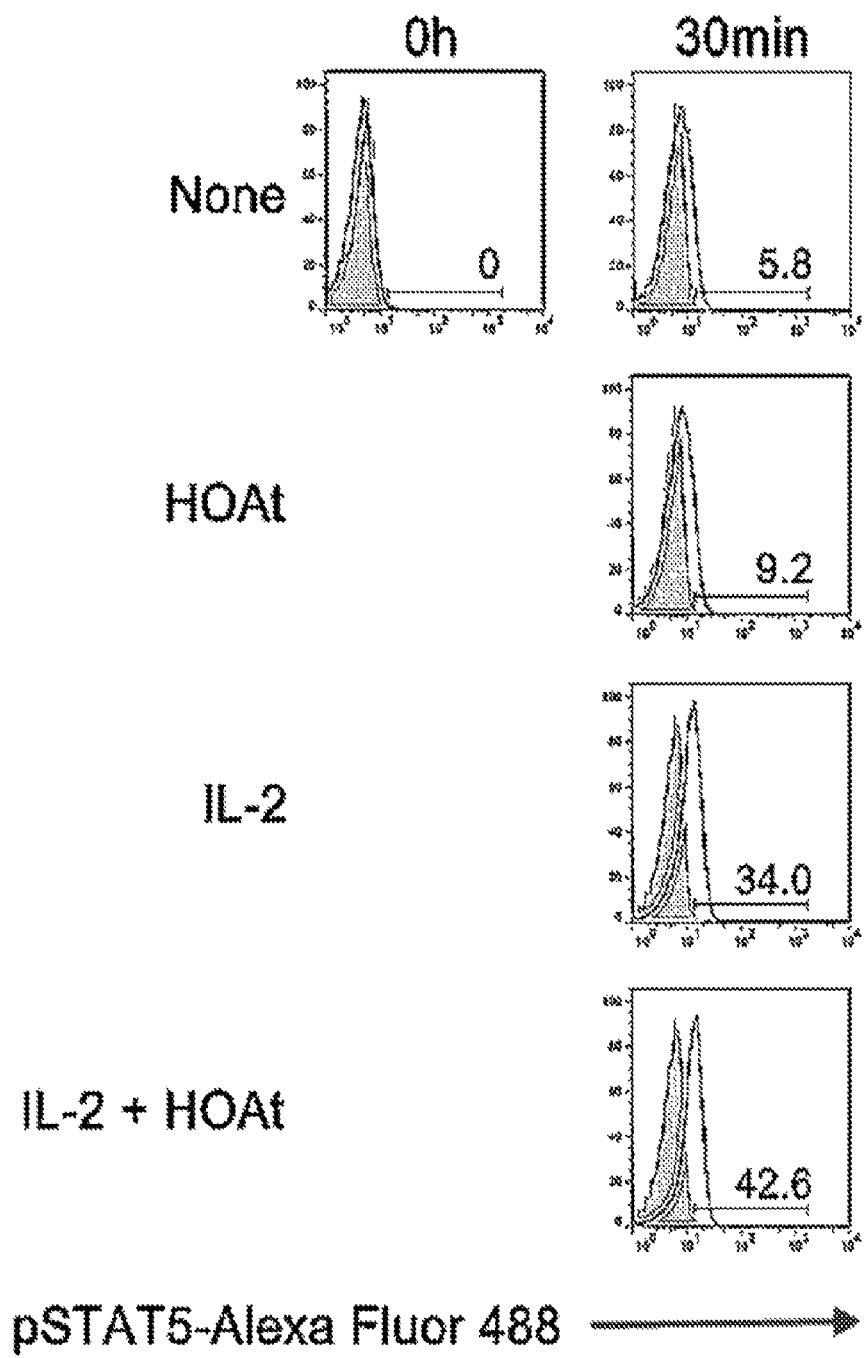
FIG. 4B shows that HOAt alone is able to induce an increase in STAT5 phosphorylation over untreated cells. While cells incubated with IL-2 alone increase the levels of STAT5 phosphorylation at 30 min, at 24 hrs the level has decreased to basal levels. Incubation of cultured $T_{CM}$ cells with a combination of IL-2 and HOAt lead to a drastic increase in STAT5 phosphorylation.
Figure 4B:
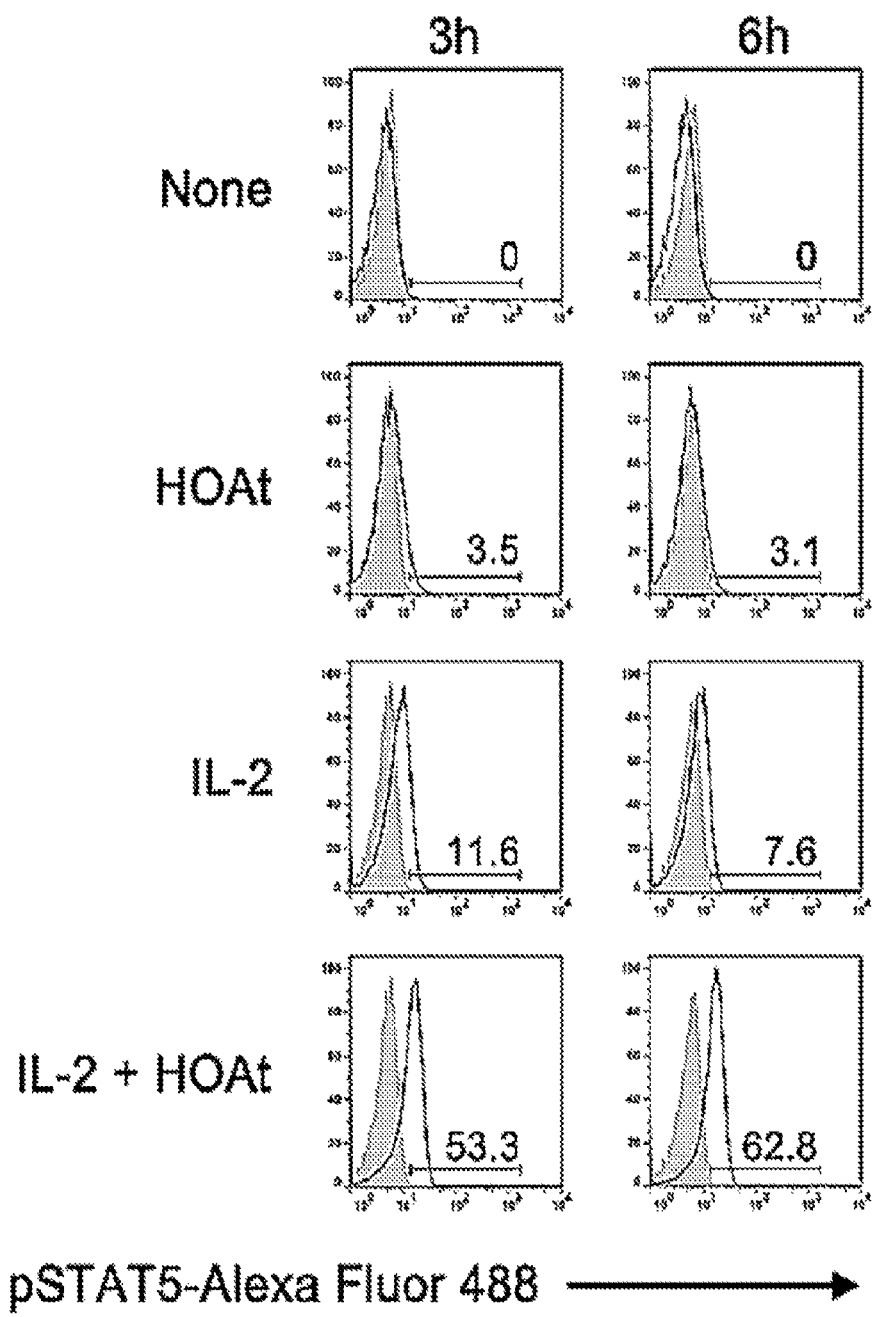
Figure 4B:
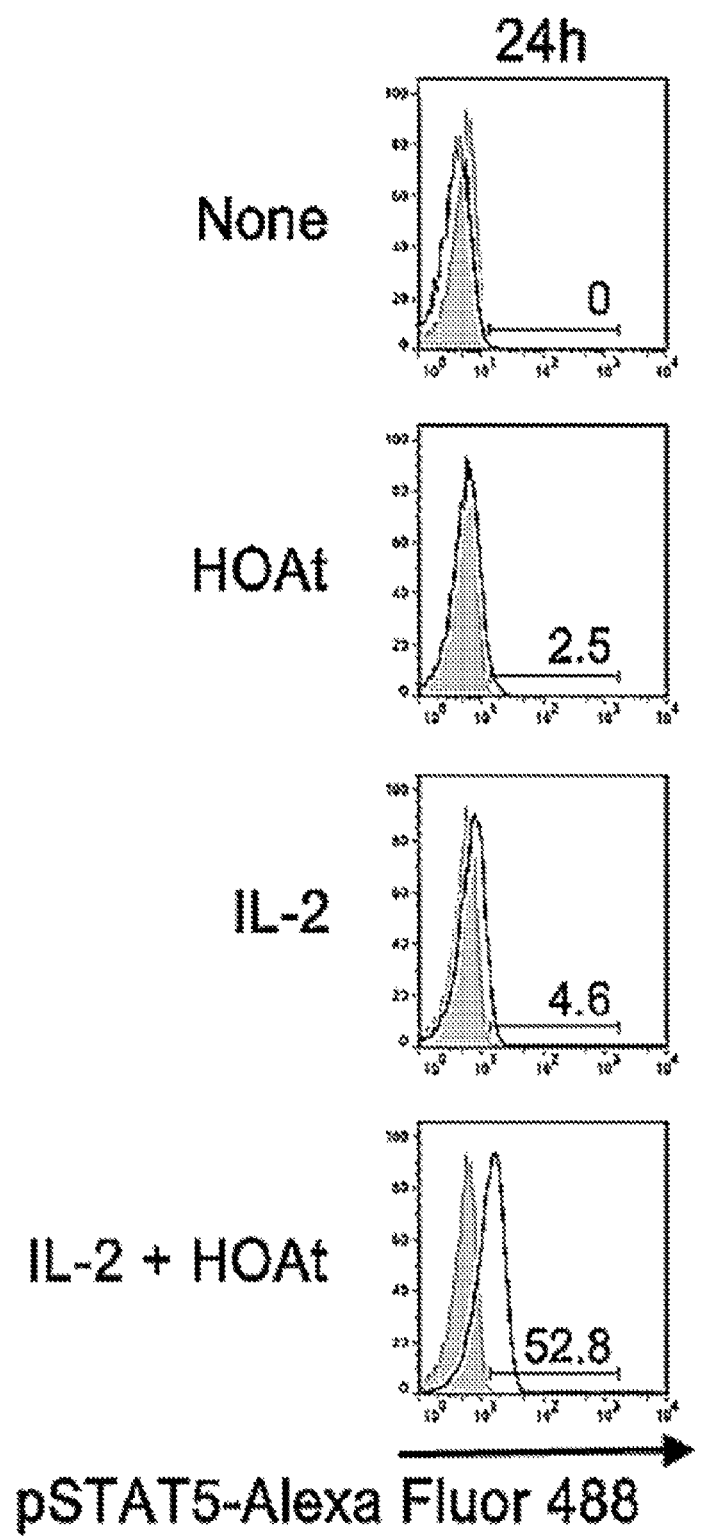

The levels of STAT5 phosphorylation were analyzed by flow cytometry after incubating cultured $T_{CM}$ with HOAt, IL-2, or a combination of both, during a 24 h period (FIG. 4B). STAT5 phosphorylation could be only slightly detected in the absence of either IL-2 or HOAt at 30 min. HOAt alone is able to induce an increase in STAT5 phosphorylation over untreated cells. Cells incubated with IL-2 alone dramatically increase the levels of STAT5 phosphorylation at 30 min, but these levels decrease to basal levels after 24 hrs of incubation. Incubation of cultured $T_{CM}$ with a combination of IL-2 and HOAt induce a drastic increase in STAT5 phosphorylation. Moreover, the levels of STAT5 phosphorylation do not significantly decrease after 24 hrs of incubation with IL-2 and HOAt.

6. Effect on the Nuclear Localization of Stat5

Figure 5A:
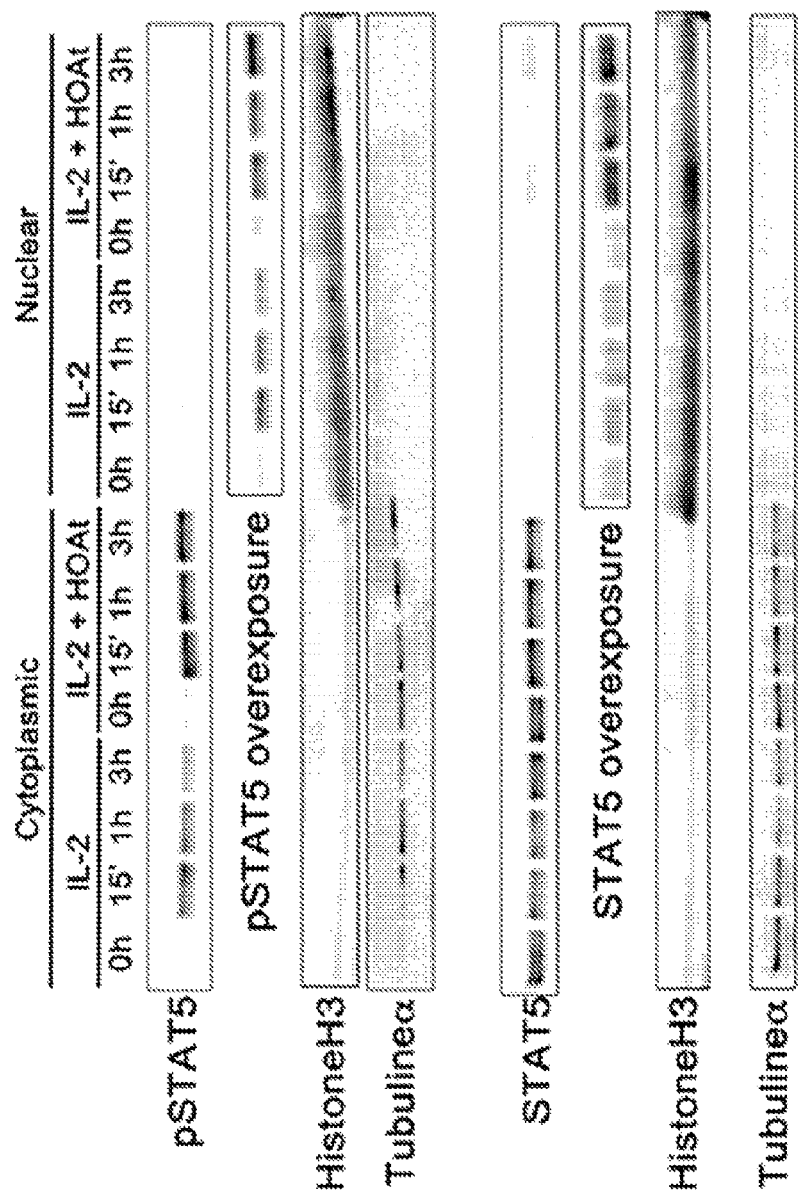
FIG. 5A shows that HOAt increases the nuclear localization of STAT5. pSTAT5 and STAT5 levels increased in the nucleus of the cells treated with HOAt at the time points indicated. Histone H3 and alpha Tubulin were used as controls for purity of the fractionation.

The levels of nuclear localization of STAT5 after incubation of the cells with IL-2 alone or in the presence of HOAt were analyzed. Nuclear translocation of STAT5 is required for its transcriptional activity. Both pSTAT5 and STAT5 levels increased in the nucleus of cells treated with HOAt at the time points indicated (FIG. 5A). Histone H3 and alpha Tubulin were used as controls for purity of the fractionation.

Figure 5B:
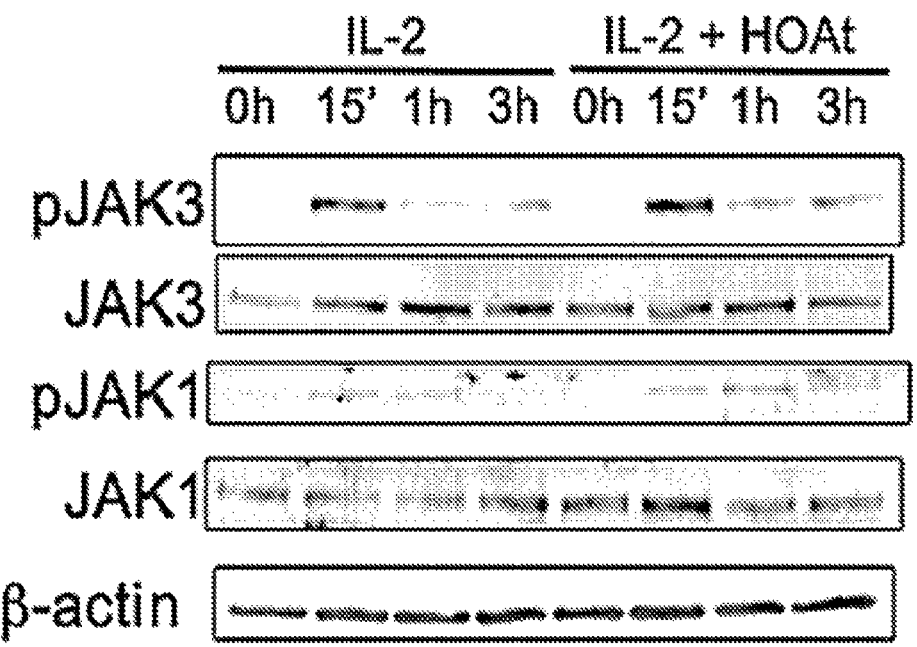
FIG. 5B shows that IL-2 alone or in the presence of HOAt increases phosphorylation of JAK1 and JAK3.

Engagement of γc-cytokines to its receptors leads to a signaling cascade initiated by the phosphorylation and activation of the janus kinases JAK1 and JAK3. These kinases then phosphorylate and activate the transcription factors STATs. EL-2 alone or in the presence of HOAt increases phosphorylation of JAK1 and JAK3 at similar levels (FIG. 5B). This indicates that HOAt alters STAT5 phosphorylation without altering the phosphorylation pattern of the JAK kinases.

Figure 5C:
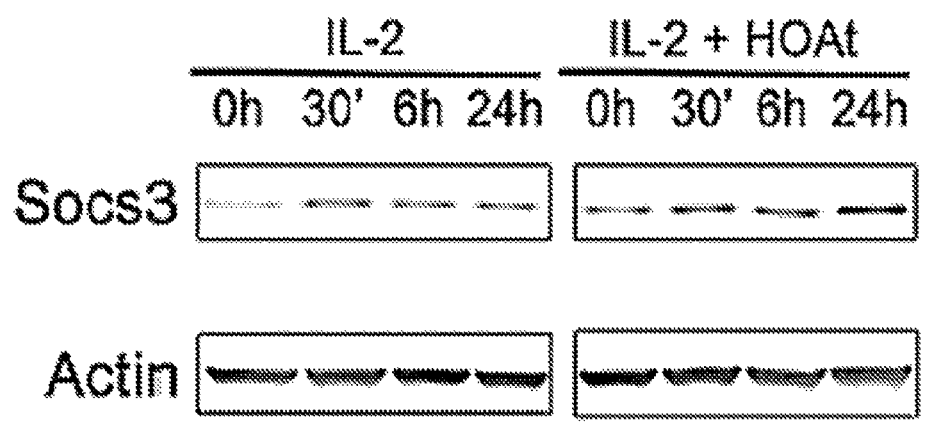
FIG. 5C shows that HOAt increases the transcription of SOC3S, a target gene for STAT5.

STAT5 is a transcriptional activator of multiple genes. To address whether HOAt will increase the transcription of any STAT5 target genes, the expression levels of SOCS3, a target gene for STAT5, were analyzed. Incubation of cells with IL-2 and HOAt was found to increase the levels of SOCS3 at 24 h post-treatment (FIG. 5C).

7. Analysis of T Cell Activation

Figure 6A:
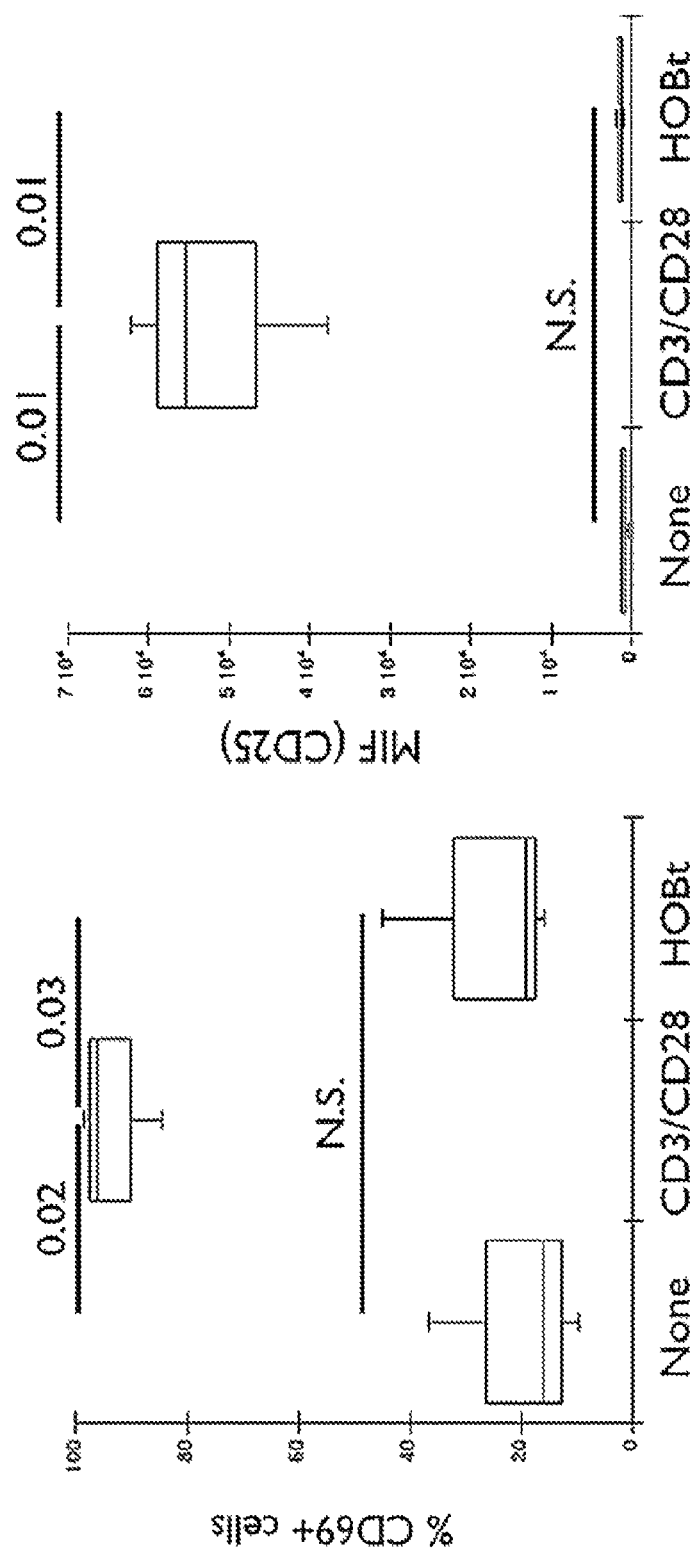
FIG. 6A shows that HOBt does not induce general T cell activation.
Figure 6B:
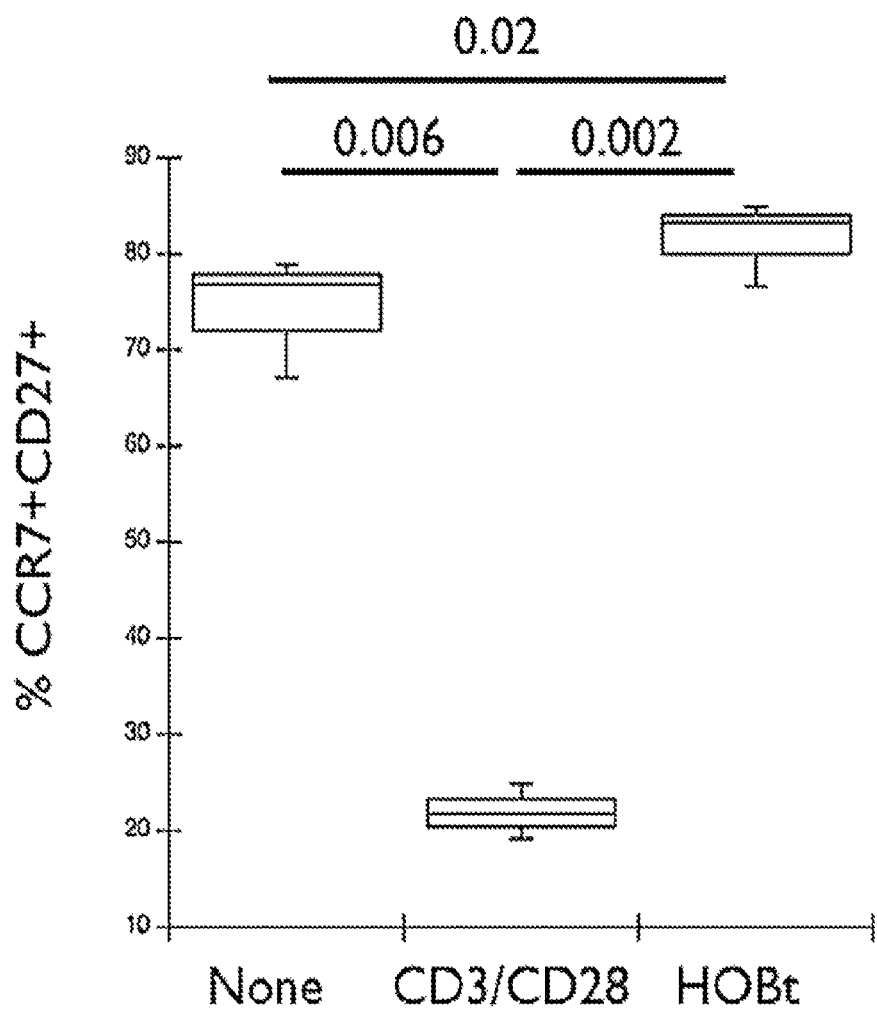
FIG. 6B shows that HOBt does not induce T cell differentiation measured as lost CCR7 and CD27 expression.

Memory cells were generated from 3 different donors and treated with either HOBt or anti-CD3/CD28 to analyze the effect of HOBt on T cell activation (FIG. 6A). Analysis of T cell activation was done by analyzing the upregulation of the activation markers CD25 and CD69 three days post activation. HOBt does not induce general T cell activation. Analysis of T cell differentiation was done by analyzing the levels of CCR7 and CD27 three days post activation (FIG. 6B). This revealed that HOBt does not induce T cell differentiation measured as loss of CCR7 and CD27 expression.

Figure 6C:
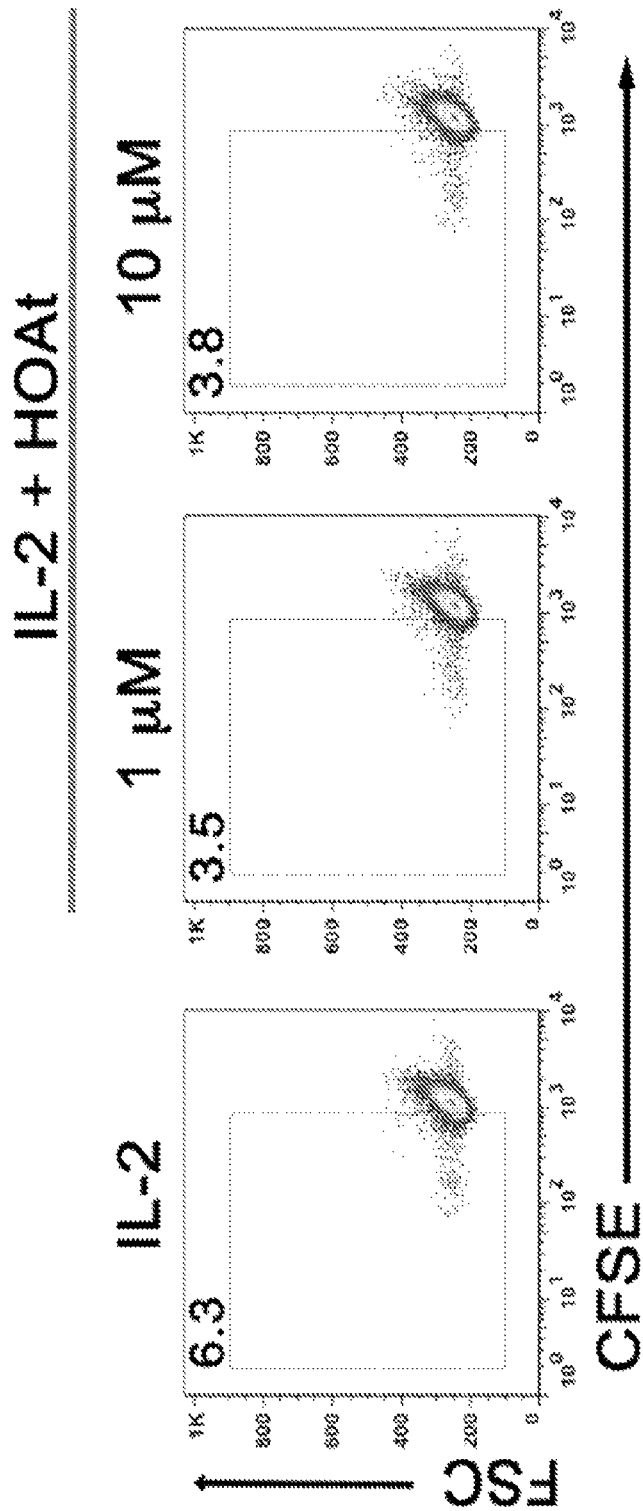
FIG. 6C shows that HOBt only induces some degree of T cell proliferation at the higher concentration tested.
Figure 6C:
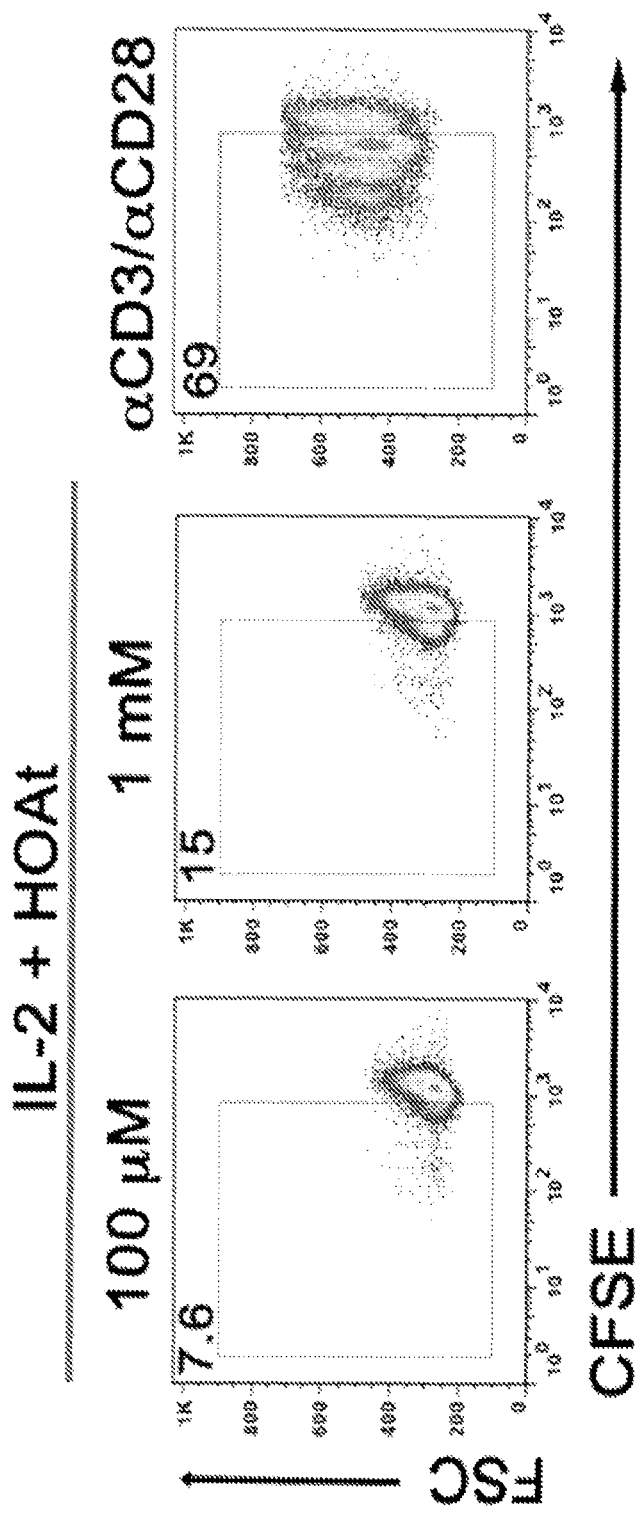
Figure 6D:
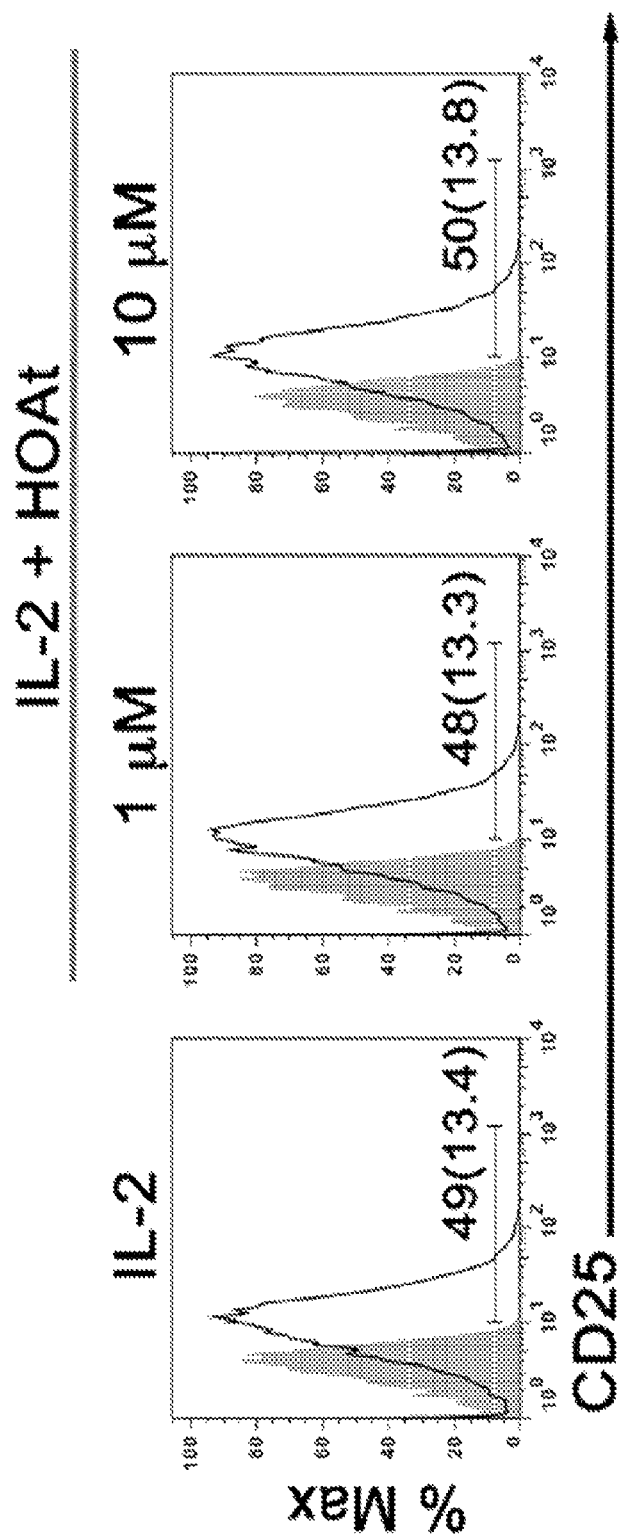
FIG. 6D shows that HOBt only induces an increase of 1.4 times of CD25 levels at the maximum concentration used. This level is increased by 37 times after TCR engagement with αCD3/αCD28.
Figure 6D:
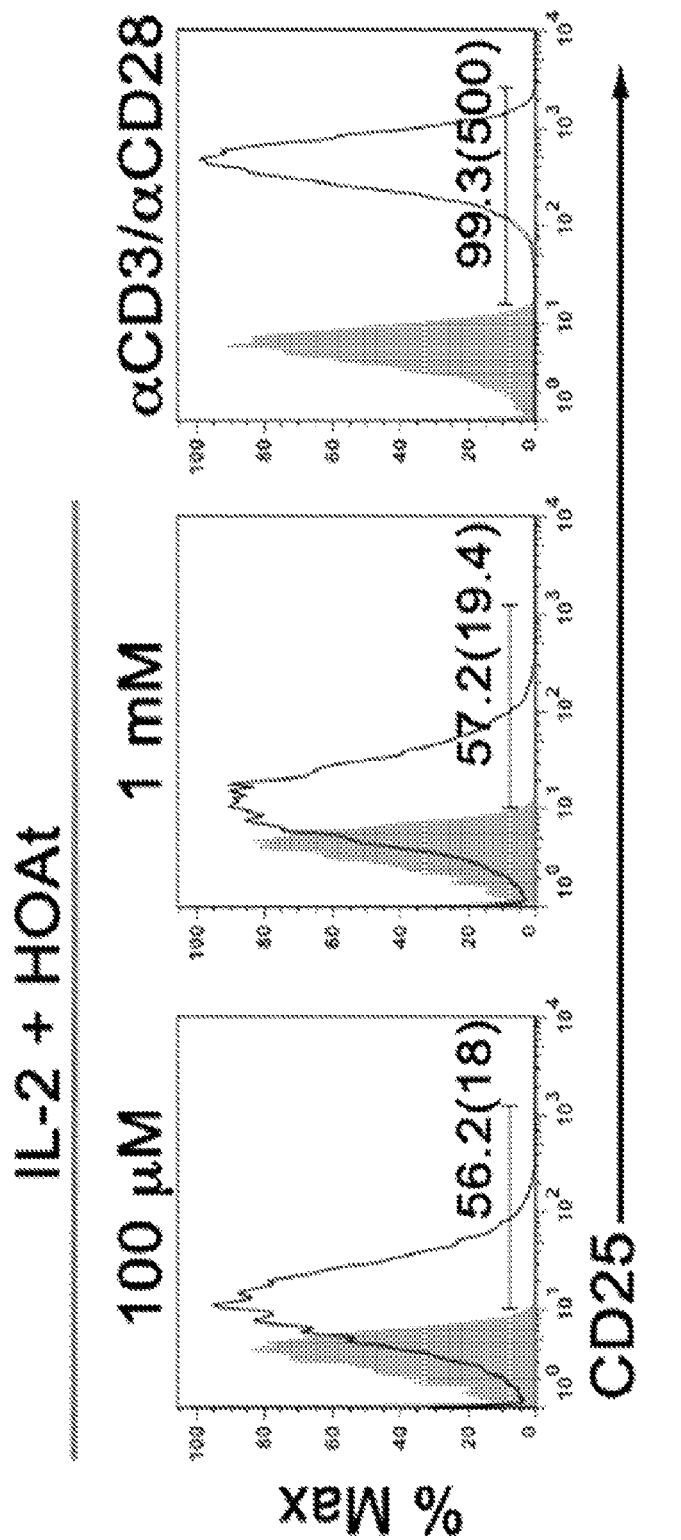

In order to determine whether HOAt is inducing T cell proliferation, culter $T_{CM}$ were incubated with HOAt in a dose dependent manner. HOAt only induces some degree of cell proliferation at the higher concentration tested (FIG. 6C). It has been shown previously that both cultured $T_{CM}$ and ex vivo $T_{CM}$ express low levels of CD25 (Bosque et al. 2011). This level is increased by 37 times after TCR engagement with αCD3/αCD28, measured as mean intensity of fluorescence (values between parenthesis, FIG. 6D). HOAt only induced an increase of 1.4 times at the maximum concentration used.

Figure 6E:
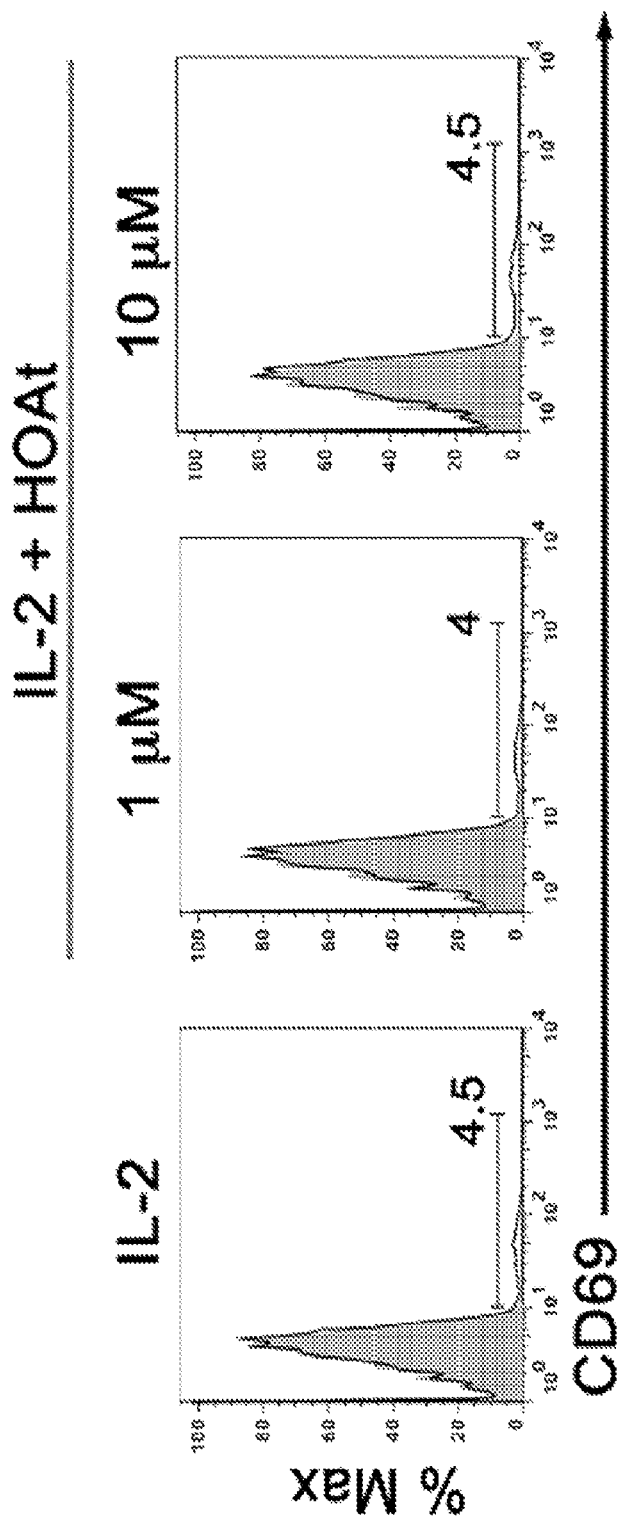
FIG. 6E shows that HOAt slightly increases the levels of T cell activation when compared with αCD3/αCD28.
Figure 6E:
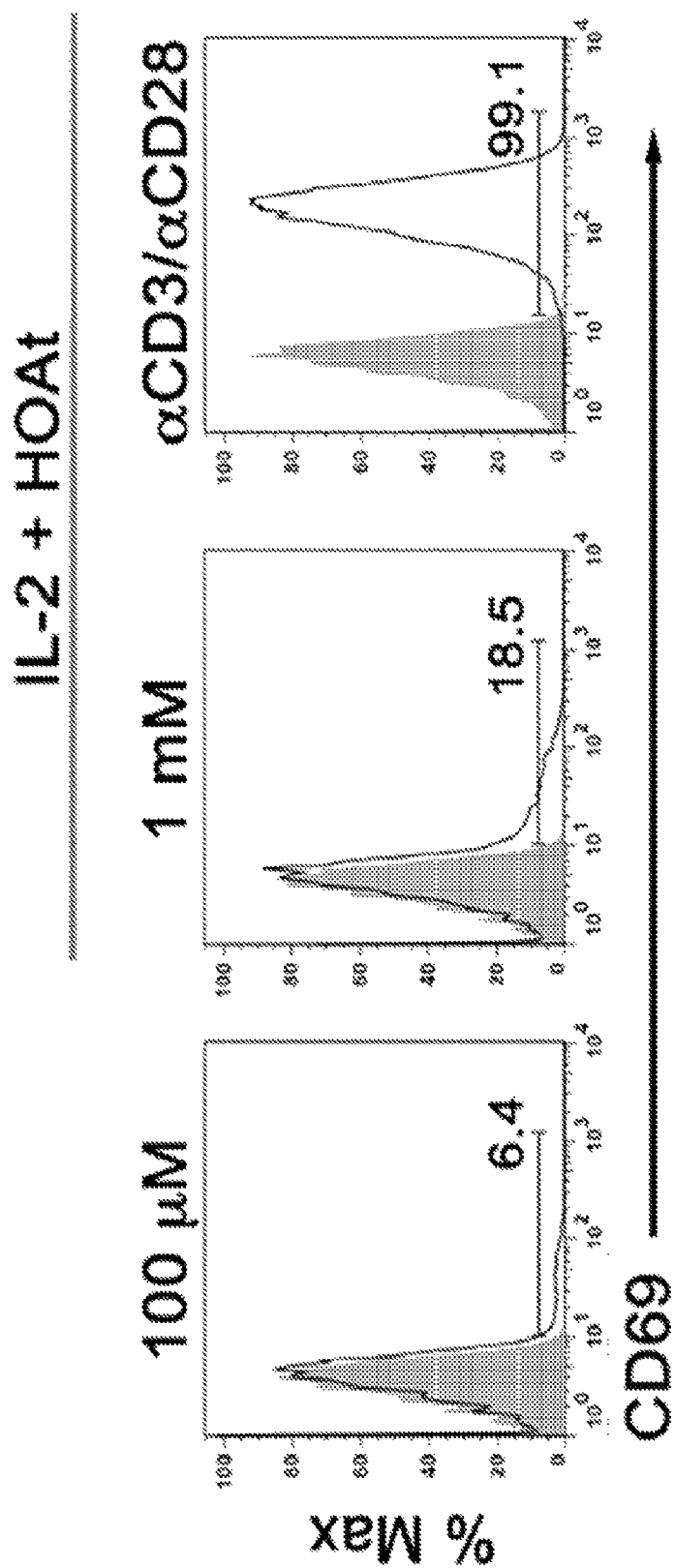

CD69 upregulation is concomitant with T cell activation. HOAt slightly increases the levels of T cell activation when compared with αCD3/αCD28 (FIG. 6E). These results indicate that HOAt can reactivate latent HIV-1 in the absence of cellular proliferation of cellular activation.

8. Viral Reactivation Mediated by Other Stimuli

Figure 7:
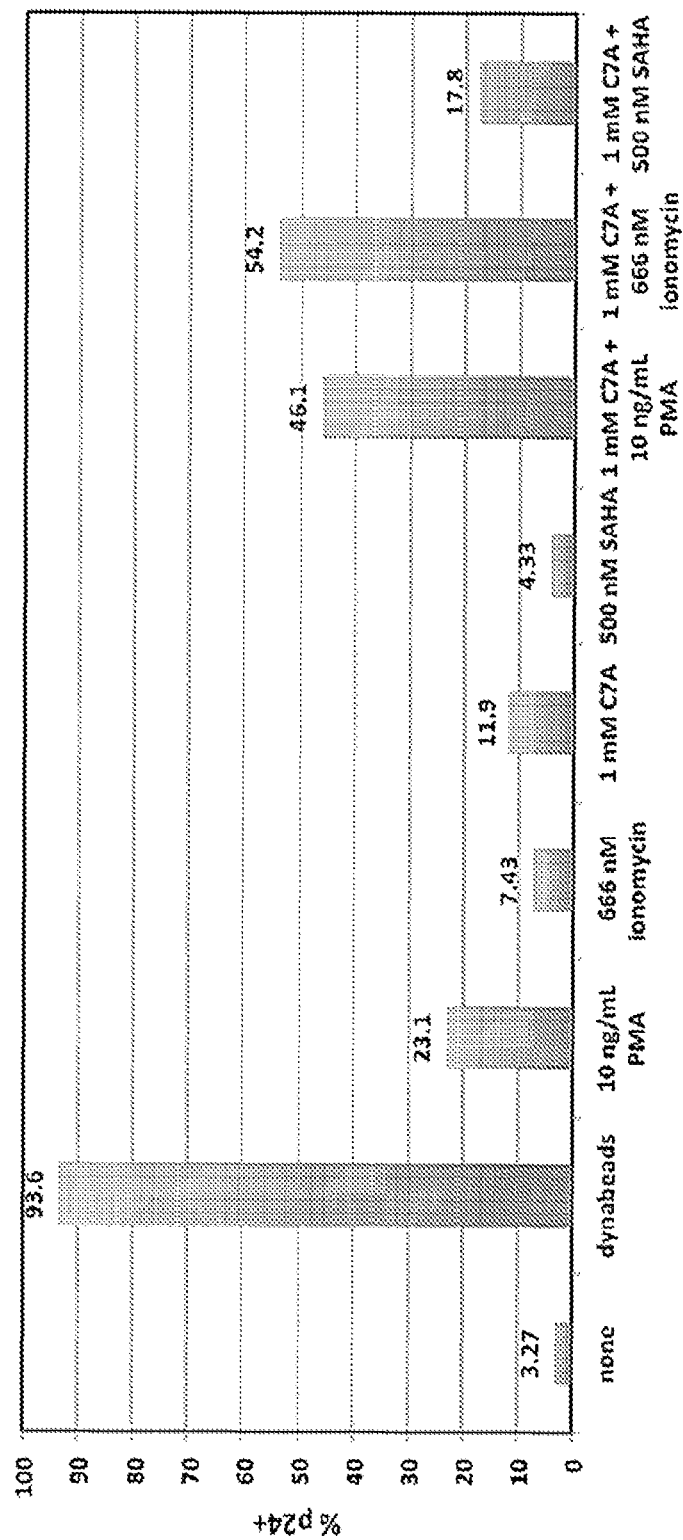
FIG. 7 shows that HOAt increases viral reactivation mediated by PMA, ionomycin and SAHA. This indicates that HOAt and additional analogs can be used to synergize the activity of other anti-latency drugs.
Figure 8:
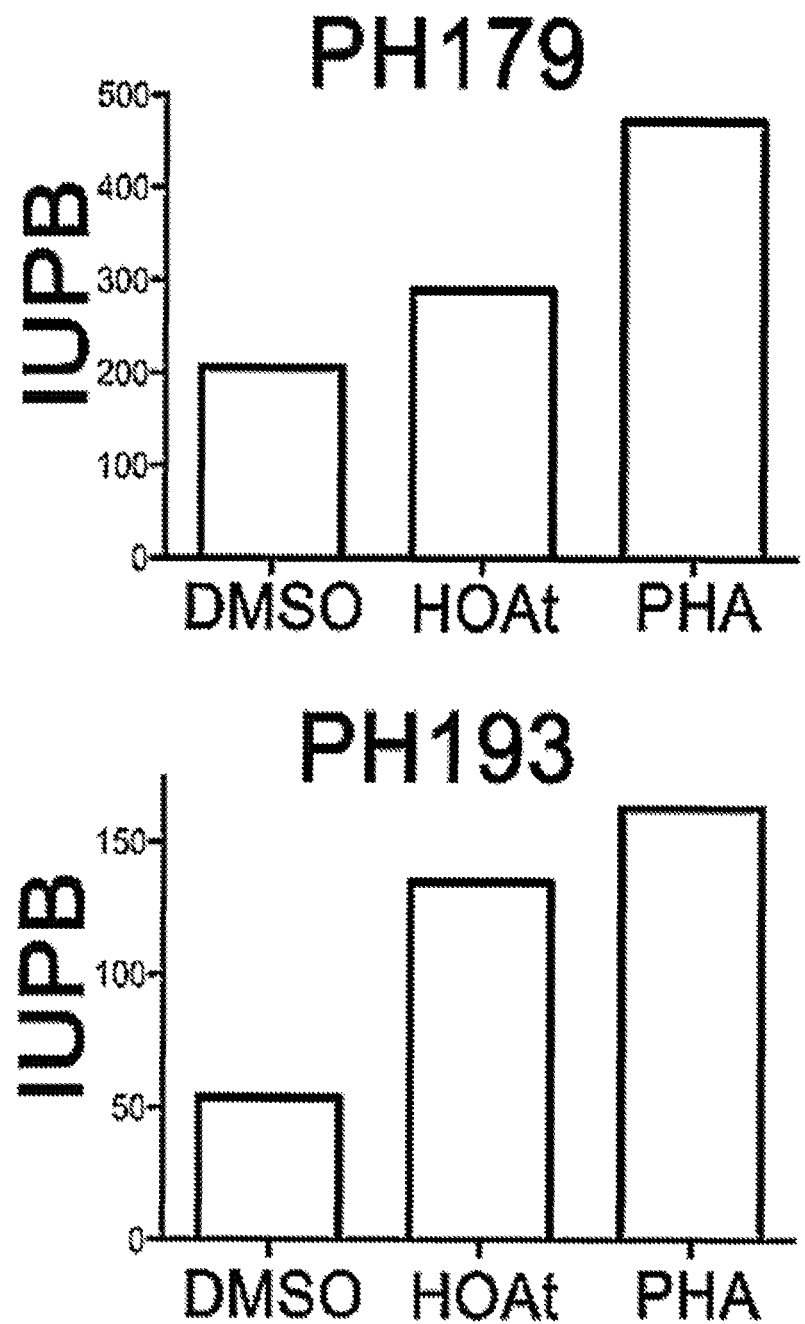
FIG. 8 shows representative data pertaining to the ability of HOAt to reactivate latent HIV-1 in cells isolated from aviremic HIV-1 patients. Briefly, cells for two patients suppressed with antiretroviral were isolated and treated with either DMSO (Control), HOAt or the mitogen PHA. As it is shown, HOAt can induce regrowth of latent viruses in both patients in vitro above the treatment control (DMSO).
Figure 9A:
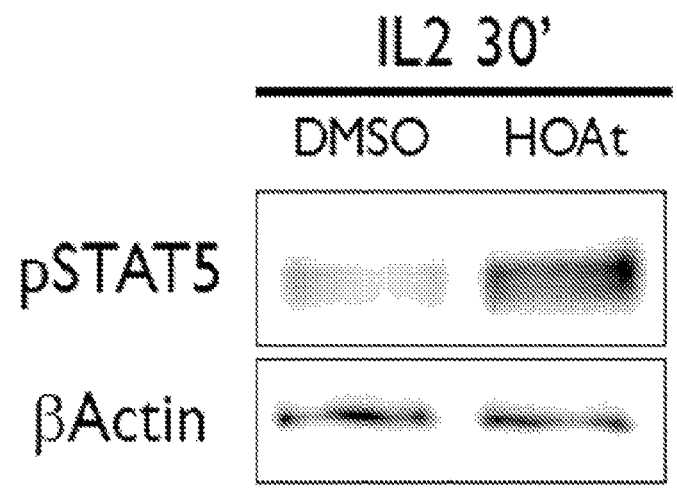
FIG. 9A shows representative data demonstrating that HOAt increases the levels of pSTAT5 in the inputs.
Figure 9B:
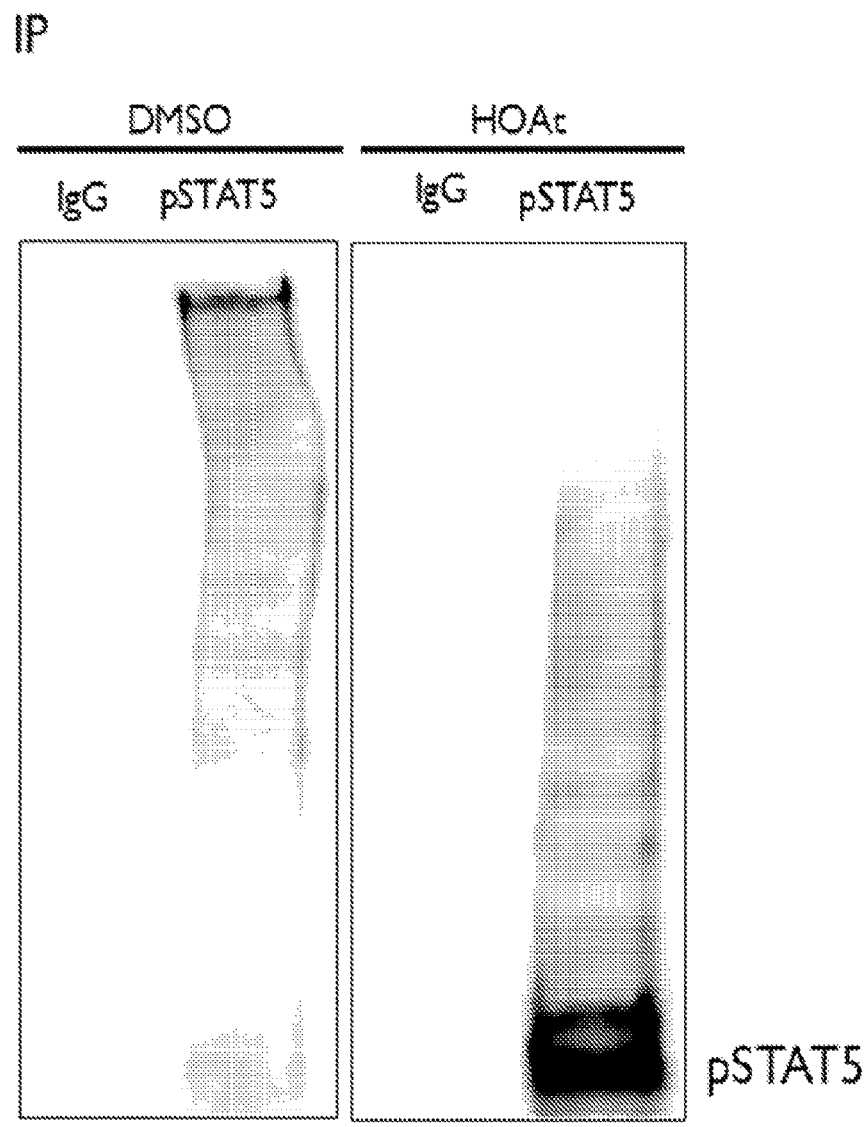
FIG. 9B shows representative data illustrating the ladder pattern normally observed in ubiquitinilated proteins. Without wishing to be bound by theory, this may suggest that HOAt and derivatives may block ubiquitation and subsequent degradation of pSTAT5. Briefly, cells were treated with DMSO or HOAt for 30 min, and subsequently treated with IL-2 for another 30 min. STAT5 was immunoprecipitated with antibodies specific for the phosphorylated protein and western blot was performed against pSTAT5.
Figure 10:
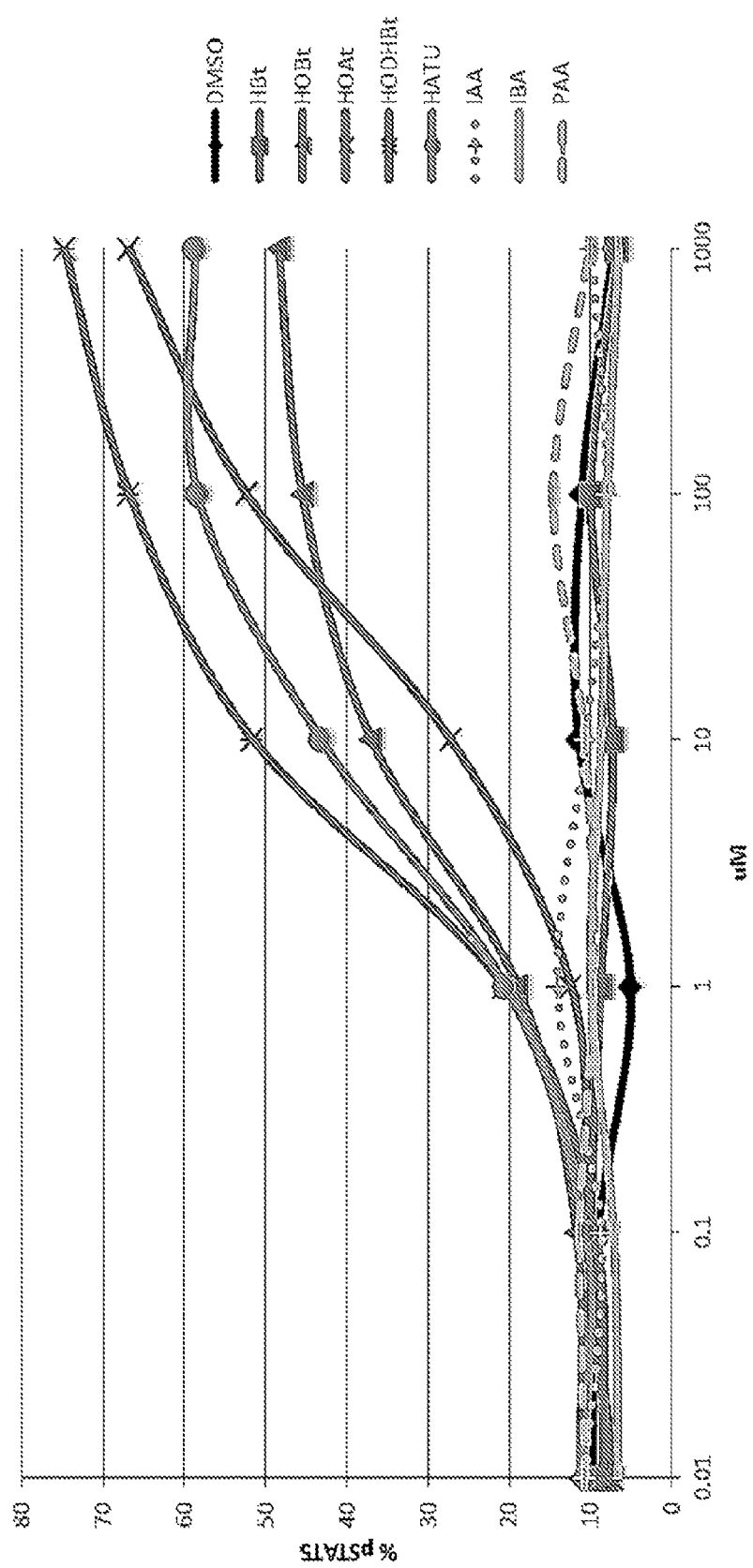
FIG. 10 shows representative data pertaining to the ability of HOBt, HOAt, HODHBt and HATU to maintain pSTAT5 levels in a dose dependent manner. Cells were treated with IL-2 and several derivatives of HOAt. Levels of pSTAT5 were measured 48 h later by flow cytometer.

To test whether HOAt can enhance viral reactivation mediated by other stimuli, cells were reactivated with three different agonists: PMA, a PKC agonist that has been shown to reactivate latent HIV in a NF-κB dependent manner; ionomycine, a ionophore that increases the intracellular levels of $Ca^{2+}$ and induces the activation of the transcription factor NFAT; and SAHA, a histone deacetylase inhibitor that has been shown to reactive latent HIV-1 in vitro and ex vivo (FIG. 7). HOAt is able to increase viral reactivation mediated by these three stimuli. These results indicate that HOAt and its derivatives can be used to synergize the activity of other anti-latency drugs.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of activating a latent retrovirus in a subject, the method comprising the step of administering to the subject an effective amount of a compound represented by a formula:

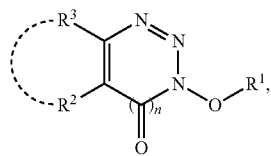

wherein n is 0 or 1;
wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino) phosphonium hexafluorophosphate (V), 1-(pyrrolidine-1-ylmethylene)pyrrolidin-1-ium hexafluorophosphate (V), and 1-(piperidin-1-ylmethylene)piperidin-1-ium hexafluorophosphate (V);
wherein $R^2$ is selected from H and C1-C4 alkyl; and
wherein $R^3$ is selected from H and C1-C4 alkyl;
or wherein $R^2$ and $R^3$ are covalently bonded and, together with the intermediate atoms, comprise phenyl substituted with 0, 1, 2, or 3 groups independently selected from Cl, CH$_3$, and NO$_2$ or unsubstituted pyridinyl.

2. The method of claim 1, wherein the retrovirus is selected from HIV-1, HIV-2, SIV, XMRV, HTLV-1, HTLV-2, HTLV-3, and HTLV-4.

3. The method of claim 1, wherein the retrovirus is HIV-1.

4. A method of activating a latent retrovirus in a subject, the method comprising the step of administering to the subject an effective amount of a compound represented by a formula selected from:

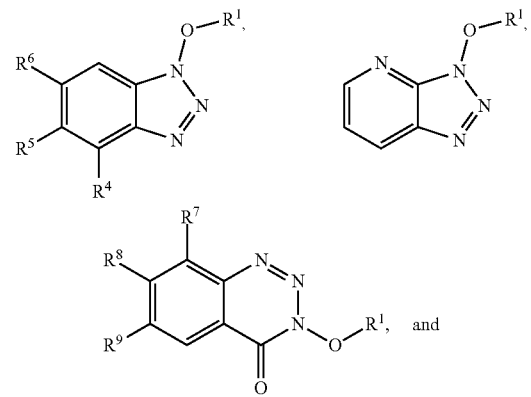

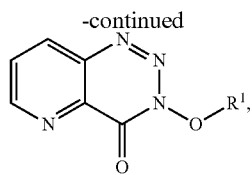

wherein $R^1$ is selected from H, C1-C4 alkyl, C1-C6 aryl, C(O)Ar, C(O)N(CH$_3$)$_2$, SO$_2$N(CH$_3$)$_2$, fluorenylmethyloxycarbonyl, N-((dimethylamino)methylene)-N-methylmethanaminium tetrafluoroborate, N-((dimethylamino)methylene)-N-methylmethanaminium hexafluorophosphate (V), tri(pyrrolidin-1-yl)phosphonium hexafluorophosphate (V), tris(dimethylamino) phosphonium hexafluorophosphate (V), 1-(pyrrolidine-1-ylmethylene)pyrrolidin-1-ium hexafluorophosphate (V), and 1-(piperidin-1-ylmethylene)piperidin-1-ium hexafluorophosphate (V);
wherein each of $R^4$, $R^5$, and $R^6$ is independently selected from H, Cl, CH$_3$, and NO$_2$,
wherein each of $R^7$, $R^8$, and $R^9$ is independently selected from H, Cl, CH$_3$, and NO$_2$.

5. The method of claim 4, wherein the retrovirus is selected from HIV-1, HIV-2, SIV, XMRV, HTLV-1, HTLV-2, HTLV-3, and HTLV-4.

6. The method of claim 4, wherein the retrovirus is HIV-1.

7. The method of claim 4, wherein $R^1$ is selected from H and N-((dimethylamino)methylene) -N-methylmethanaminium hexafluorophosphate (V).

8. The method of claim 4, wherein $R^1$ is H.

9. The method of claim 4, wherein the compound is represented by a formula:

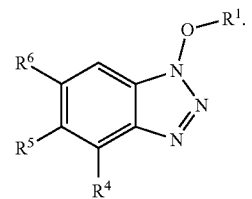

10. The method of claim 4, wherein the compound is represented by a formula:

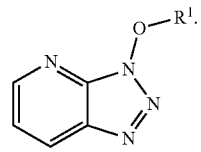

11. The method of claim 4, wherein the compound is represented by a formula:

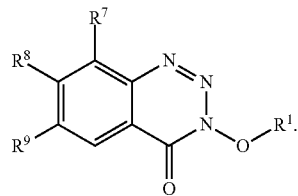

12. The method of claim 4, wherein the compound is represented by a formula:
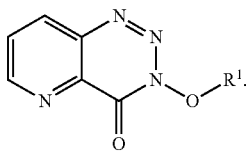
13. A method of activating a latent retrovirus in a subject, the method comprising the step of administering to the subject an effective amount of a compound selected from:
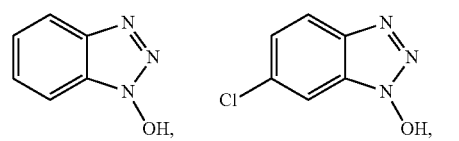
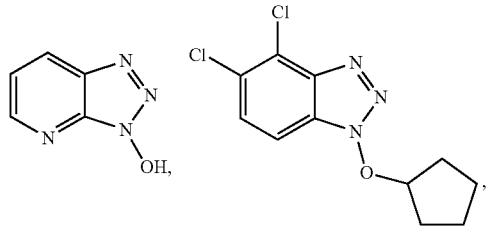
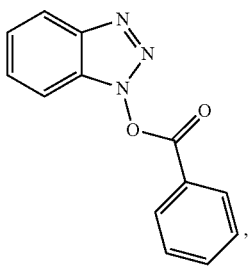
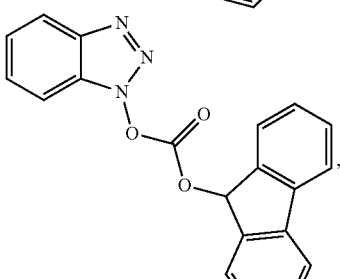
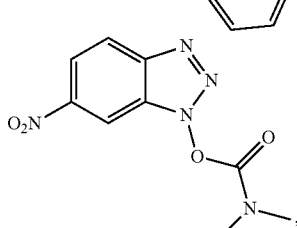
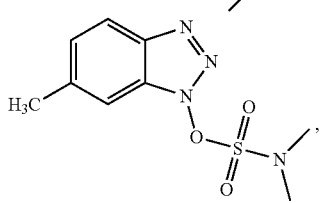
-continued
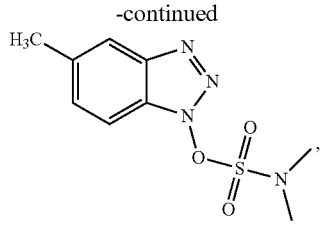
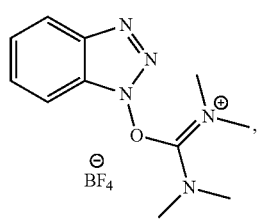
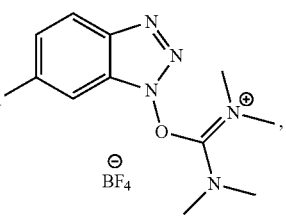
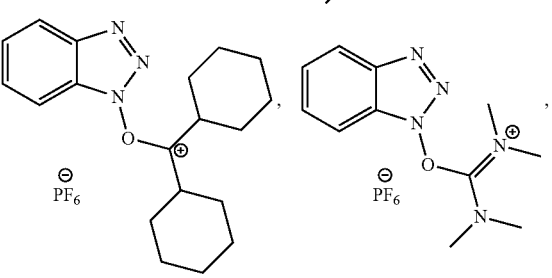
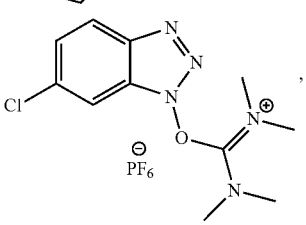
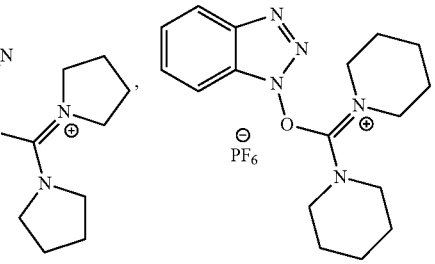
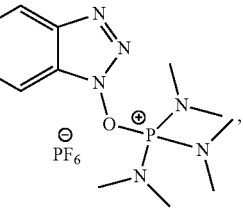

-continued

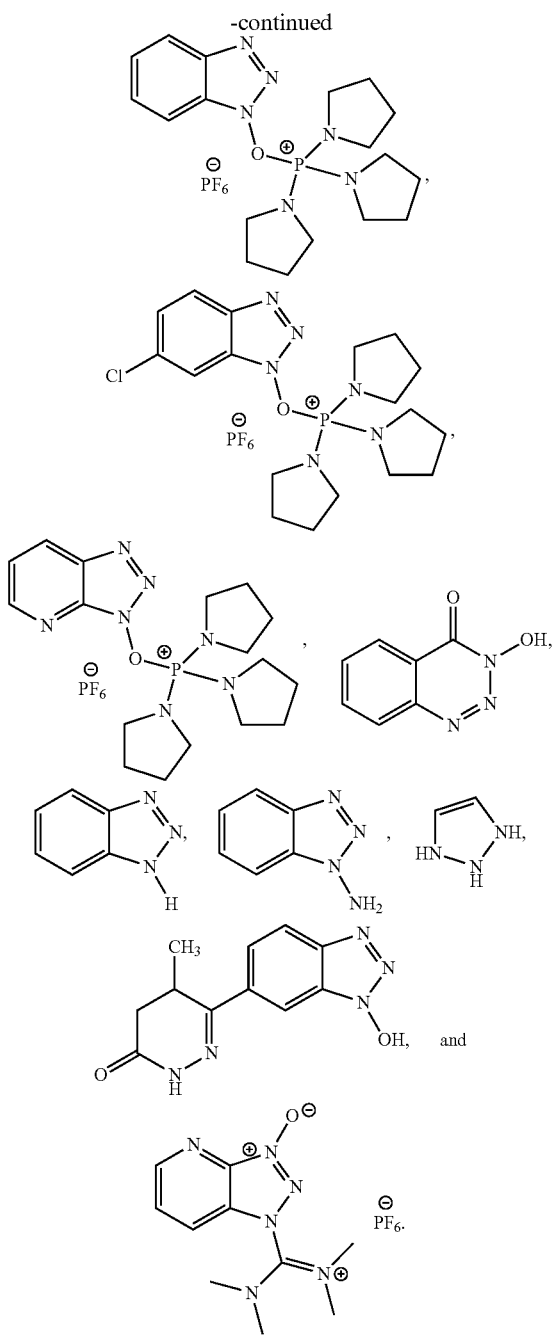

14. The method of claim 13, wherein the retrovirus is selected from HIV-1, HIV-2, SIV, XMRV, HTLV-1, HTLV-2, HTLV-3, and HTLV-4.

15. The method of claim 13, wherein the retrovirus is HIV-1.

16. The method of claim 13, wherein the compound is selected from:

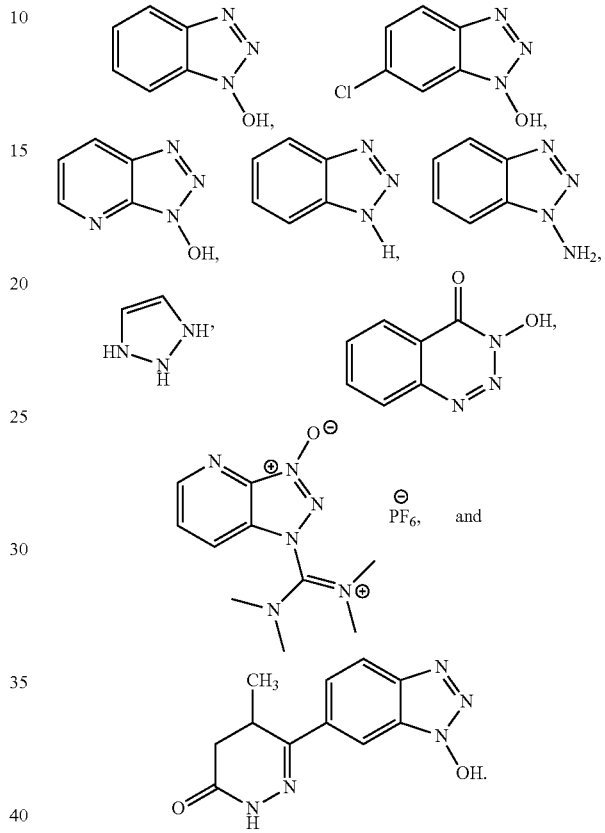

17. The method of claim 16, wherein the retrovirus is selected from HIV-1, HIV-2, SIV, XMRV, HTLV-1, HTLV-2, HTLV-3, and HTLV-4.

18. The method of claim 16, wherein the retrovirus is HIV-1.

19. The method of claim 13, wherein the subject is a population of cells.

20. The method of claim 13, wherein the subject is a mammal.

* * * * *